US010174316B2

(12) United States Patent
Laux et al.

(10) Patent No.: US 10,174,316 B2

(45) Date of Patent: Jan. 8, 2019

(54) ANTI-CONNEXIN COMPOUNDS TARGETED TO CONNEXINS AND METHODS OF USE THEREOF

(71) Applicant: CoDa Therapeutics, Inc., San Diego, CA (US)

(72) Inventors: Wilda Laux, Mangere (NZ); Colin Richard Green, Auckland (NZ)

(73) Assignee: OCUNEXUS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 14/467,978

(22) Filed: Aug. 25, 2014

(65) Prior Publication Data

US 2014/0371297 A1 Dec. 18, 2014

Related U.S. Application Data

(62) Division of application No. 13/230,744, filed on Sep. 12, 2011, now Pat. No. 8,815,819, which is a division of application No. 10/581,813, filed as application No. PCT/IB2004/004431 on Dec. 3, 2004, now Pat. No. 8,034,789.

(30) Foreign Application Priority Data

Dec. 3, 2003 (NZ) ........................................ 529936

(51) Int. Cl.

| | |
|---|---|
| ***C07H 21/02*** | (2006.01) |
| ***C07H 21/04*** | (2006.01) |
| ***A61K 31/70*** | (2006.01) |
| ***C12N 15/113*** | (2010.01) |
| ***C12N 15/11*** | (2006.01) |
| ***A61K 31/7105*** | (2006.01) |
| ***A61K 31/711*** | (2006.01) |
| *C12N 5/00* | (2006.01) |

(52) U.S. Cl.

CPC .......... *C12N 15/113* (2013.01); *A61K 31/711* (2013.01); *A61K 31/7105* (2013.01); *C12N 15/111* (2013.01); *C12N 15/1138* (2013.01); *C12N 2310/11* (2013.01); *C12N 2310/12* (2013.01); *C12N 2310/315* (2013.01); *C12N 2320/31* (2013.01); *Y02P 20/582* (2015.11)

(58) Field of Classification Search

None

See application file for complete search history.

(56) References Cited

U.S. PATENT DOCUMENTS

| | | | | |
|---|---|---|---|---|
| 7,098,190 | B1 | 8/2006 | Becker et al. | |
| 7,615,540 | B2 * | 11/2009 | Green | C12N 15/111 435/375 |
| 7,879,811 | B2 * | 2/2011 | Green | C12N 15/111 435/375 |
| 7,902,164 | B2 | 3/2011 | Green et al. | |
| 8,034,789 | B2 | 10/2011 | Laux et al. | |
| 2007/0060538 | A1 | 3/2007 | Becker et al. | |
| 2007/0072819 | A1 | 3/2007 | Becker et al. | |
| 2007/0072820 | A1 | 3/2007 | Becker et al. | |
| 2008/0221051 | A1 | 9/2008 | Becker et al. | |
| 2008/0249041 | A1 | 10/2008 | Becker et al. | |

FOREIGN PATENT DOCUMENTS

| | | |
|---|---|---|
| CN | 1347902 A | 5/2002 |
| KR | 10-2006-7013276 | 1/2014 |
| WO | WO-1996-19194 | 6/1996 |
| WO | WO-1998-24797 | 6/1998 |
| WO | WO-2000-044409 | 8/2000 |

OTHER PUBLICATIONS

O'Carroll et al Cell Communication & Adhesion, vol. 15:27-42, 2008.*

Agrawal, "Antisense oligonucleotides; towards clinical trials." *TIBTECH,* 1996, 14:376-387.

Baldwin et al., "Growth-factors in corneal wound healing following refractive surgery: A Review," *ACTA Ophthalmologica Scandinavica,* 2002, 80(3):238-247.

Becker et al., "Connexin α1 and cell proliferation in the developing chick retina," *Experimental Neurology,* Apr. 1999, 156(2):326-332.

Branch, "A good antisense molecule is hard to find," *TIBS,* Feb. 1998, 45-50.

Bregman et al., "Transplants and Neurotrophic Factors Prevent Atrophy of Mature CNS Neurons after Spinal Cord Injury," Experimental Neurology, 1998, 149(1):13-27.

Calabrese et al., "Connexin 36 controls synchronization of Ca2+ oscillations and insulin secretion in MIN6 cells," *Diabetes,* 2003, 52(2):417-424.

Davis et al., "Modulation of Connexin43 Expression: Effects on Cellular Coupling," *Journal of Cardiovascular Electrophysiology,* Feb. 1995, 6(2):103-114.

Franteseva et al., "Ischemia-Induced Brain Damage Depends on Specific Gap-Junctional coupling," *Journal of Cerebral Blood Flow and Metabolism,* Apr. 2002, 22(4):453-462.

Goliger et al., "Wounding Alters Epidermal Connexin Expression and Gap Junction-Mediated Intercellular Communication," *Molecular Biology of the Cell,* 1995, 6:1491-1501.

Grazul-Bilska et al., "Transfection of Bovine Luteal Cells With Gap Junctional Protein Connexin 43 (Cx43) Antisense Oligonucleotide Affects Progesterone Secretion," $34^{th}$ Annual Meeting of the Society for the Study of Reproduction, Aug. 8-11, 1998, College Station, TX, *Biology of Reproduction,* 1998, 58(1):78.

(Continued)

*Primary Examiner* — Sean McGarry

(74) *Attorney, Agent, or Firm* — Duane Morris LLP

(57) ABSTRACT

Methods and compositions for modulating the activities of connexins are provided, including, for example, for use in post-surgical, trauma, or tissue engineering applications. These compounds and methods can be used therapeutically, for example, to reduce the severity of adverse effects associated diseases and disorders where localized disruption in direct cell-cell communication is desirable.

13 Claims, 12 Drawing Sheets

Specification includes a Sequence Listing.

(56) References Cited

OTHER PUBLICATIONS

Green et al., "Spatiotemporal depletion of connexins using antisense oligonucleotides: Techniques in the study of gap junctions," *Methods in Molecular Biology: Connexin Methods and Protocols,* R. Bruzzone et al., eds., 2001, 154:175-185.

Haopeng et al., "Experimental study on spinal cord injury treated with the combination of fetal spinal cord transplantation and methylprednisolone," Journal of Xi'an Medical University, English Edition, 2001, 13(2):138-141 (abstract), 1 page.

Hodgins, "Connecting Wounds with Connexins," *The Journal of Investigative Dermatology,* 2004, 122(5):ix-x.

Jen et al., "Suppression of Gene Expression by Targeted Disruption of Messenger RNA: Available Options and Current Strategies," *Stem Cells,* 2000, 18:307-319.

Jin et al., "Combination of fetal tissue transplantation and gene therapy to promote spinal cord regeneration," Society for Neuroscience, 2003, Presented on Nov. 9, 2003 in New Orleans, LA (abstract), 2 pages.

Le Gurun et al., "Connexin-36 contributes to control function of insulin-producing cells," *Journal of Biological Chemistry,* 2003, 278(39):37690-37697.

Moore et al., "Selective block of gap junction channel expression with connexin-specific antisense oligodeoxynucleotides," *American Journal of Physiology,* Nov. 1994, 265(1):C1371-C1388.

Onifer et al., "Combining methylprednisolone, peripheral nerves, FGF1, fibrin, and vertebral wiring for spinal cord repair," Society for Neuroscience, 1999, 25(1-2):492 (abstract), 2 pages.

Qiu et al., "Targeting connexin43 expression accelerates the rate of wound repair," *Current Biology,* Sep. 30, 2003, 13(19):1967-1703.

Ratkay-Traub et al., "Regeneration of rabbit cornea following excimer laser photorefractive keratectomy; a study on gap junctions, epithelial junctions and epidermal growth factor receptor expression in correlation with cell proliferation," *Experimental Eye Research,* Sep. 2001, 73(3):291-302.

Rozental et al., "Stable Transfection With Connexin43 Inhibits Neuronal Differentiation of PC12 Cells," *Society for Neuroscience Abstracts,* Society for Neuroscience, Oct. 1997, 25:22.

Ruch et al., "Inhibition of Gap Junctional Intercellular Communication and Enhancement of Growth in BALBk 3T3 Cells Treated With Connexin43 Antisense Oligonucleotides," *Molecular Carcinogenesis,* 1995, 14:269-274.

Santoro et al., "A General Purpose RNA-Cleaving DNA Enzyme," *Proc. Natl. Acad. Sci. USA,* Apr. 1997, 94:4262-4266.

Sohl et al., "The murine gap junction gene connexin36 is highly expressed in mouse retina and regulated during brain development," *FEBS LETTERS,* May 1998, 428(1-2):27-31.

Willecke et al. "Structural and functional diversity of connexin genes in the mouse and human genome," *Biological Chemistry,* May 2002, 383(5):725-737.

International Search Report dated Jun. 19, 2000, from International Patent Application No. PCT/GB00/00238, 5 pages.

Extended Search Report dated Dec. 19, 2005, from corresponding European Patent Application No. 05016736.0, 11 pages.

International Search Report dated Jan. 3, 2006, from International Patent Application No. PCT/IB2004/004431, 7 pages.

Examination Report dated Aug. 30, 2006, from corresponding European Patent Application No. 05016736.0, 7 pages.

Office Action dated Dec. 12, 2011, from corresponding Indian Patent Application No. 1827/KOLNP/2006, 1 page.

Notice of Reasons for Rejection dated Apr. 20, 2012, from corresponding Japanese Patent Application No. 2006-542058, 12 total pages.

Partial Search Report dated Jul. 24, 2012, from corresponding European Patent Application No. 10015438.4, 7 pages.

Notice of Restriction Requirement dated Jul. 30, 2012, from corresponding Canadian Patent Application No. 2,547,780, 3 pages.

Office Action dated Aug. 6, 2012, from corresponding Chinese Patent Application No. 200480041251.9, 7 total pages.

Examination Report dated Aug. 17, 2012, from corresponding Singapore Patent Application No. 200603748-5, 10 pages.

Extended Search Report dated Oct. 24, 2012, from corresponding European Patent Application No. 10015438.4, 14 pages.

Corrected Partial Search Report dated Dec. 21, 2012, from corresponding European Patent Application No. 10015439.2, 13 pages.

Notice of Final Rejection dated May 24, 2013, from corresponding Japanese Patent Application No. 2006-542058, 4 pages.

Examiner's Report dated Oct. 3, 2013, from corresponding Canadian Patent Application No. 2,547,780, 2 pages.

Office Action dated Jan. 30, 2014, from corresponding Chinese Patent Application No. 201310098015.1, 14 total pages.

Office Action dated Dec. 29, 2014, from related Chinese Application No. 201310098015.1, 10 total pages.

* cited by examiner

C D

A B

A B

A B

SEQUENCE LISTING

<160> NUMBER OF SEQ ID NOS: 67

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gtaattgcgg caagaagaat tgtttctgtc 30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
gtaattgcgg caggaggaat tgtttctgtc 30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ggcaagagac accaaagaca ctaccagcat 30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
tcctgagcaa tacctaacga acaaata 27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
catctccttg gtgctcaacc 20

<210> SEQ ID NO 6
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 6
ctgaagtcga cttggcttgg 20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctcagatagt ggccagaatg c 21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgtccaggt gactccaagg 20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtccgagcc cagaaagatg aggtc 25

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaggcgcac gtgagacac 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgaagacaat gaagatgtt 19

<210> SEQ ID NO 12
<211> LENGTH: 3088
<212> TYPE: DNA
<213> ORGANISM: Homo sapiens

<400> SEQUENCE: 12

-continued

```
acaaaaaagc ttttacgagg tatcagcact tttctttcat tagggggaag gcgtgaggaa     60
agtaccaaac agcagcggag ttttaaactt taaatagaca ggtctgagtg cctgaacttg    120
ccttttcatt ttacttcatc ctccaaggag ttcaatcact tggcgtgact tcactacttt    180
taagcaaaag agtggtgccc aggcaacatg ggtgactgga gcgccttagg caaactcctt    240
gacaaggttc aagcctactc aactgctgga gggaaggtgt ggctgtcagt acttttcatt    300
ttccgaatcc tgctgctggg gacagcggtt gagtcagcct ggggagatga gcagtctgcc    360
tttcgttgta acactcagca acctggttgt gaaaatgtct gctatgacaa gtctttccca    420
atctctcatg tgcgcttctg ggtcctgcag atcatatttg tgtctgtacc cacactcttg    480
tacctggctc atgtgttcta tgtgatgcga aaggaagaga aactgaacaa gaaagaggaa    540
gaactcaagg ttgcccaaac tgatggtgtc aatgtggaca tgcacttgaa gcagattgag    600
ataaagaagt tcaagtacgg tattgaagag catggtaagg tgaaaatgcg aggggggttg    660
ctgcgaacct acatcatcag tatcctcttc aagtctatct ttgaggtggc cttcttgctg    720
atccagtggt acatctatgg attcagcttg agtgctgttt acacttgcaa aagagatccc    780
tgcccacatc aggtggactg tttcctctct cgccccacgg agaaaaccat cttcatcatc    840
ttcatgctgg tggtgtcctt ggtgtccctg gccttgaata tcattgaact cttctatgtt    900
ttcttcaagg gcgttaagga tcgggttaag ggaaagagcg acccttacca tgcgaccagt    960
ggtgcgctga gccctgccaa agactgtggg tctcaaaaat atgcttattt caatggctgc   1020
tcctcaccaa ccgctcccct ctcgcctatg tctcctcctg ggtacaagct ggttactggc   1080
gacagaaaca attcttcttg ccgcaattac aacaagcaag caagtgagca aaactgggct   1140
aattacagtg cagaacaaaa tcgaatgggg caggcgggaa gcaccatctc taactcccat   1200
gcacagcctt ttgatttccc cgatgataac cagaattcta aaaaactagc tgctggacat   1260
gaattacagc cactagccat tgtggaccag cgaccttcaa gcagagccag cagtcgtgcc   1320
agcagcagac ctcggcctga tgacctggag atctagatac aggcttgaaa gcatcaagat   1380
tccactcaat tgtggagaag aaaaaaggtg ctgtagaaag tgcaccaggt gttaattttg   1440
atccggtgga ggtggtactc aacagcctta ttcatgaggc ttagaaaaca caaagacatt   1500
agaataccta ggttcactgg gggtgtatgg ggtagatggg tggagaggga ggggataaga   1560
gaggtgcatg ttggtattta aagtagtgga ttcaaagaac ttagattata aataagagtt   1620
ccattaggtg atacatagat aagggctttt tctccccgca aacaccccta agaatggttc   1680
tgtgtatgtg aatgagcggg tggtaattgt ggctaaatat ttttgtttta ccaagaaact   1740
gaaataattc tggccaggaa taaatacttc ctgaacatct taggtctttt caacaagaaa   1800
aagacagagg attgtcctta agtccctgct aaaacattcc attgttaaaa tttgcacttt   1860
gaaggtaagc tttctaggcc tgaccctcca ggtgtcaatg gacttgtgct actatatttt   1920
tttattcttg gtatcagttt aaaattcaga caaggcccac agaataagat tttccatgca   1980
tttgcaaata cgtatattct ttttccatcc acttgcacaa tatcattacc atcacttttt   2040
catcattcct cagctactac tcacattcat ttaatggttt ctgtaaacat ttttaagaca   2100
gttgggatgt cacttaacat tttttttttt tgagctaaag tcagggaatc aagccatgct   2160
taatatttaa caatcactta tatgtgtgtc gaagagtttg ttttgtttgt catgtattgg   2220
tacaagcaga tacagtataa actcacaaac acagatttga aaataatgca catatggtgt   2280
tcaaatttga acctttctca tggatttttg tggtgtgggc caatatggtg tttacattat   2340
```

-continued

```
ataattcctg ctgtggcaag taaagcacac ttttttttc tcctaaaatg tttttccctg   2400

tgtatcctat tatggatact ggttttgtta attatgattc tttattttct ctcctttttt   2460

taggatatag cagtaatgct attactgaaa tgaatttcct ttttctgaaa tgtaatcatt   2520

gatgcttgaa tgatagaatt ttagtactgt aaacaggctt tagtcattaa tgtgagagac   2580

ttagaaaaaa tgcttagagt ggactattaa atgtgcctaa atgaattttg cagtaactgg   2640

tattcttggg ttttcctact taatacacag taattcagaa cttgtattct attatgagtt   2700

tagcagtctt ttggagtgac cagcaacttt gatgtttgca ctaagatttt atttggaatg   2760

caagagaggt tgaaagagga ttcagtagta cacatacaac taatttattt gaactatatg   2820

ttgaagacat ctaccagttt ctccaaatgc ctttttaaa actcatcaca gaagattggt   2880

gaaaatgctg agtatgacac ttttcttctt gcatgcatgt cagctacata aacagttttg   2940

tacaatgaaa attactaatt tgtttgacat tccatgttaa actacggtca tgttcagctt   3000

cattgcatgt aatgtagacc tagtccatca gatcatgtgt tctggagagt gttctttatt   3060

caataaagtt ttaatttagt ataaacat                                      3088
```

<210> SEQ ID NO 13
<211> LENGTH: 1308
<212> TYPE: DNA
<213> ORGANISM: Homo sapiens

<400> SEQUENCE: 13

```
atgggcgact ggagctttct gggaagactc ttagaaaatg cacaggagca ctccacggtc     60

atcggcaagg tttggctgac cgtgctgttc atcttccgca tcttggtgct gggggccgcg    120

gcggaggacg tgtggggcga tgagcagtca gacttcacct gcaacaccca gcagccgggc    180

tgcgagaacg tctgctacga cagggccttc cccatctccc acatccgctt ctgggcgctg    240

cagatcatct tcgtgtccac gcccaccctc atctacctgg gccacgtgct gcacatcgtg    300

cgcatggaag agaagaagaa agagagggag gaggaggagc agctgaagag agagagcccc    360

agccccaagg agccaccgca ggacaatccc tcgtcgcggg acgaccgcgg cagggtgcgc    420

atggccgggg cgctgctgcg gacctacgtc ttcaacatca tcttcaagac gctgttcgag    480

gtgggcttca tcgccggcca gtactttctg tacggcttcg agctgaagcc gctctaccgc    540

tgcgaccgct ggccctgccc caacacggtg gactgcttca tctccaggcc cacggagaag    600

accatcttca tcatcttcat gctggcggtg gcctgcgcgt ccctgctgct caacatgctg    660

gagatctacc acctgggctg gaagaagctc aagcagggcg tgaccagccg cctcggcccg    720

gacgcctccg aggccccgct ggggacagcc gatcccccgc ccctgccccc cagctcccgg    780

ccgcccgccg ttgccatcgg gttcccaccc tactatgcgc acaccgctgc gcccctggga    840

caggcccgcg ccgtgggcta ccccggggcc ccgccaccag ccgcggactt caaactgcta    900

gccctgaccg aggcgcgcgg aaagggccag tccgccaagc tctacaacgg ccaccaccac    960

ctgctgatga ctgagcagaa ctgggccaac caggcggccg agcggcagcc cccggcgctc   1020

aaggcttacc cggcagcgtc cacgcctgca gcccccagcc ccgtcggcag cagctccccg   1080

ccactcgcgc acgaggctga ggcgggcgcg gcgcccctgc tgctggatgg gagcggcagc   1140

agtctggagg ggagcgccct ggcagggacc cccgaggagg aggagcaggc cgtgaccacc   1200

gcggcccaga tgcaccagcc gcccttgccc ctcggagacc caggtcgggc cagcaaggcc   1260

agcagggcca gcagcgggcg ggccagaccg gaggacttgg ccatctag                1308
```

-continued

<210> SEQ ID NO 14
<211> LENGTH: 1601
<212> TYPE: DNA
<213> ORGANISM: Homo sapiens

<400> SEQUENCE: 14
ctccggccat cgtccccacc tccacctggg ccgcccgcga ggcagcggac ggaggccggg 60
agccatgggt gactggggct tcctggagaa gttgctggac caggtccgag agcactcgac 120
cgtggtgggt aagatctggc tgacggtgct cttcatcttc cgcatcctca tcctgggcct 180
ggccggcgag tcagtgtggg gtgacgagca gtcagatttc gagtgtaaca cggcccagcc 240
aggctgcacc aacgtctgct atgaccaggc cttccccatc tcccacatcc gctactgggt 300
gctgcagttc ctcttcgtca gcacacccac cctggtctac ctgggccatg tcatttacct 360
gtctcggcga gaagagcggc tggcgcagaa ggagggggag ctgcgggcac tgccggccaa 420
ggacccacag gtggagcggg cgctggccgg catagagctt cagatggcca agatctcggt 480
ggcagaagat ggtcgcctgc gcattccgcg agcactgatg ggcacctatg tcgccagtgt 540
gctctgcaag agtgtgctag aggcaggctt cctctatggc cagtggcgcc tgtacggctg 600
gaccatggag cccgtgtttg tgtgccagcg agcaccctgc ccctacctcg tggactgctt 660
tgtctctcgc cccacggaga agaccatctt catcatcttc atgttggtgg ttggactcat 720
ctccctggtg cttaacctgc tggagttggt gcacctgctg tgtcgctgcc tcagccgggg 780
gatgagggca cggcaaggcc aagacgcacc cccgacccag ggcacctcct cagaccctta 840
cacggaccag ggtcttcttc tacctccccg tggccagggg ccctcatccc caccatgccc 900
cacctacaat gggctctcat ccagtgagca gaactgggcc aacctgacca cagaggagag 960
gctggcgtct tccaggcccc ctctcttcct ggacccaccc cctcagaatg gccaaaaacc 1020
cccaagtcgt cccagcagct ctgcttctaa gaagcagtat gtatagaggc ctgtggctta 1080
tgtcacccaa cagaggggtc ctgagaagtc tggctgcctg ggatgccccc tgccccctcc 1140
tggaaggctc tgcagagatg actgggctgg ggaagcagat gcttgctggc catggagcct 1200
cattgcaagt tgttcttgaa cacctgaggc cttcctgtgg cccaccaggc actacggctt 1260
cctctccaga tgtgctttgc ctgagcacag acagtcagca tggaatgctc ttggccaagg 1320
gtactggggc cctctggcct tttgcagctg atccagagga acccagagcc aacttacccc 1380
aacctcaccc tatggaacag tcacctgtgc gcaggttgtc ctcaaaccct ctcctcacag 1440
gaaaaggcgg attgaggctg ctgggtcagc cttgatcgca cagacagagc ttgtgccgga 1500
tttggccctg tcaaggggac tggtgccttg ttttcatcac tccttcctag ttctactgtt 1560
caagcttctg aaataaacag gacttgatca caaaaaaaaa a 1601

<210> SEQ ID NO 15
<211> LENGTH: 2574
<212> TYPE: DNA
<213> ORGANISM: Homo sapiens

<400> SEQUENCE: 15
gcaaaaagcg tgggcagttg gagaagaagc agccagagtg tgaagaagcc cacggaagga 60
aagtccaggg aggaggaaaa gaagcagaag ttttggcatc tgttccctgg ctgtgccaag 120
atgggcgatt ggagcttcct gggaaatttc ctggaggaag tacacaagca ctcgaccgtg 180
gtaggcaagg tctggctcac tgtcctcttc atattccgta tgctcgtgct gggcacagct 240
gctgagtctt cctgggggga tgagcaggct gatttccggt gtgatacgat tcagcctggc 300

-continued

```
tgccagaatg tctgctacga ccaggctttc cccatctccc acattcgcta ctgggtgctg    360
cagatcatct tcgtctccac gccctctctg gtgtacatgg gccacgccat gcacactgtg    420
cgcatgcagg agaagcgcaa gctacgggag gccgagaggg ccaaagaggt ccggggctct    480
ggctcttacg agtacccggt ggcagagaag gcagaactgt cctgctggga ggaagggaat    540
ggaaggattg ccctccaggg cactctgctc aacacctatg tgtgcagcat cctgatccgc    600
accaccatgg aggtgggctt cattgtgggc cagtacttca tctacggaat cttcctgacc    660
accctgcatg tctgccgcag gagtccctgt ccccacccgg tcaactgtta cgtatcccgg    720
cccacagaga agaatgtctt cattgtcttt atgctggctg tggctgcact gtccctcctc    780
cttagcctgg ctgaactcta ccacctgggc tggaagaaga tcagacagcg atttgtcaaa    840
ccgcggcagc acatggctaa gtgccagctt tctggcccct ctgtgggcat agtccagagc    900
tgcacaccac cccccgactt taatcagtgc ctggagaatg gccctggggg aaaattcttc    960
aatcccttca gcaataatat ggcctcccaa caaaacacag acaacctggt caccgagcaa   1020
gtacgaggtc aggagcagac tcctggggaa ggtttcatcc aggttcgtta tggccagaag   1080
cctgaggtgc ccaatggagt ctcaccaggt caccgccttc cccatggcta tcatagtgac   1140
aagcgacgtc ttagtaaggc cagcagcaag gcaaggtcag atgacctatc agtgtgaccc   1200
tcctttatgg gaggatcagg accaggtggg aacaaaggag gctcagagaa gaaagacgtg   1260
tcccttctga actgatgctt tctcactgtc atcactgctt ggctcctttg agccccgggt   1320
ctcaatgacg ttgctcatta attctagaaa ctataaccag ggctctggga tagtaagaga   1380
ggtgacaacc cacccagact gcagttccct ccccaccctc tacccagtat acgaagcctt   1440
tcagattact catgaaacag ggtagaggga aagaagggaa gcatggcaaa agctggcctg   1500
gaagggatag ccagagggat agaatgactc tctctctaca taccagcagc ataccaaatg   1560
cgttctctaa gttcctacct ccttgacctg atcaccctcc ctcctccaag gaagagctca   1620
aagttcccag ccaatagaca gcatgaatca aggaacttgc attatatgtg ctcttgaatc   1680
tgttgtctcc atggaccatt cctcggagta gtggtgagat ggccttgggt tgcccttggc   1740
ttctcctccc tctactcagc cttaaaaagg gcttcttgga actttaccag cagcctcagc   1800
tttacaaatg ccttggtatg tacctctggc aaatgcccca ccttggtgat gttgcaacct   1860
ttccttctgc tagggtgtac acctagcctg tgcaggtgtc agccctgcta gggagtcact   1920
gtacacacaa actctactgg aattcctgcc aacatctgtc accctgcagc tcctttacag   1980
ttcaatccaa tgatagaaac catcccttcc ctttctccct tggctgttca cccagccatt   2040
ccctgaaggc cttaccaaca ggaatatcca agaagctgtt gtcccctctc gaaccctgac   2100
cagatcatca gccactgagg ccagtggaat ttccccaggc cttgttaaaa caaagaaagc   2160
attgtacctc tcagattccc cttgtggaaa aaaaaattct gctgtgaaga tgaaaataaa   2220
aatggagaga aaacactgga aaactatttt cccctcctat ttacttcctt tgctgactgc   2280
caacttagtg ccaagaggag gtgtgatgac agctatggag gcccccagat ctctctctcc   2340
tggaggcttt agcaggggca aggaaatagt aggggaatct ccagctctct tggcagggcc   2400
tttatttaaa gagcgcagag attcctatgt ctccctagtg cccctaatga gactgccaag   2460
tgggggctgt agaaaagcct tgccttcccc agggattggc ctggtctctg tattcactgg   2520
atccataatg ggttgctgtt gttttggatg aaggtaaacg atgcttggaa ttgg          2574
```

<210> SEQ ID NO 16
<211> LENGTH: 1191

<212> TYPE: DNA
<213> ORGANISM: Homo sapiens

<400> SEQUENCE: 16
atgagttgga gctttctgac tcgcctgcta gaggagattc acaaccattc cacatttgtg 60
gggaagatct ggctcactgt tctgattgtc ttccggatcg tccttacagc tgtaggagga 120
gaatccatct attacgatga gcaaagcaaa tttgtgtgca acacagaaca gccgggctgt 180
gagaatgtct gttatgatgc gtttgcacct ctctcccatg tacgcttctg ggtgttccag 240
atcatcctgg tggcaactcc ctctgtgatg tacctgggct atgctatcca caagattgcc 300
aaaatggagc acggtgaagc agacaagaag gcagctcgga gcaagcccta tgcaatgcgc 360
tggaaacaac accgggctct ggaagaaacg gaggaggaca acgaagagga tcctatgatg 420
tatccagaga tggagttaga aagtgataag gaaaataaag agcagagcca acccaaacct 480
aagcatgatg gccgacgacg gattcgggaa gatgggctca tgaaaatcta tgtgctgcag 540
ttgctggcaa ggaccgtgtt tgaggtgggt tttctgatag ggcagtattt tctgtatggc 600
ttccaagtcc acccgtttta tgtgtgcagc agacttcctt gtcctcataa gatagactgc 660
tttatttcta gacccactga aaagaccatc ttccttctga taatgtatgg tgttacaggc 720
ctttgcctct tgcttaacat ttgggagatg cttcatttag ggtttgggac cattcgagac 780
tcactaaaca gtaaaaggag ggaacttgag gatccgggtg cttataatta tcctttcact 840
tggaatacac catctgctcc ccctggctat aacattgctg tcaaaccaga tcaaatccag 900
tacaccgaac tgtccaatgc taagatcgcc tacaagcaaa acaaggccaa cacagcccag 960
gaacagcagt atggcagcca tgaggagaac ctcccagctg acctggaggc tctgcagcgg 1020
gagatcagga tggctcagga acgcttggat ctggcagttc aggcctacag tcaccaaaac 1080
aaccctcatg gtccccggga gaagaaggcc aaagtggggt ccaaagctgg gtccaacaaa 1140
agcactgcca gtagcaaatc aggggatggg aagaactctg tctggattta a 1191

<210> SEQ ID NO 17
<211> LENGTH: 1362
<212> TYPE: DNA
<213> ORGANISM: Homo sapiens

<400> SEQUENCE: 17
agcgccaaga gagaaagagc acatatttct ccgtgggaca ctccttgtat tggtgggtga 60
gaaatgggcg actggagttt cctggggaac atcttggagg aggtgaatga gcactccacc 120
gtcatcggca gagtctggct caccgtgctt ttcatcttcc ggatcctcat ccttggcacg 180
gccgcagagt tcgtgtgggg ggatgagcaa tccgacttcg tgtgcaacac ccagcagcct 240
ggctgcgaga acgtctgcta cgacgaggcc tttcccatct cccacattcg cctctgggtg 300
ctgcagatca tcttcgtctc caccccgtcc ctgatgtacg tggggcacgc ggtgcactac 360
gtccgcatgg aggagaagcg caaaagccgc gacgaggagc tgggccagca ggcggggact 420
aacggcggcc cggaccaggg cagcgtcaag aagagcagcg gcagcaaagg cactaagaag 480
ttccggctgg aggggaccct gctgaggacc tacatctgcc acatcatctt caagaccctc 540
tttgaagtgg gcttcatcgt gggccactac ttcctgtacg ggttccggat cctgcctctg 600
taccgctgca gccggtggcc ctgccccaat gtggtggact gcttcgtgtc ccggcccacg 660
gagaaaacca tcttcatcct gttcatgttg tctgtggcct ctgtgtccct attcctcaac 720
gtgatggagt tgagccacct gggcctgaag gggatccggt ctgccttgaa gaggcctgta 780
gagcagcccc tgggggagat tcctgagaaa tccctccact ccattgctgt ctcctccatc 840
cagaaagcca agggctatca gcttctagaa gaagagaaaa tcgtttccca ctatttcccc 900
ttgaccgagg ttgggatggt ggagaccagc ccactgcctg ccaagccttt caatcagttc 960
gaggagaaga tcagcacagg acccctgggg gacttgtccc ggggctacca agagacactg 1020
ccttcctacg ctcaggtggg ggcacaagaa gtggagggcg aggggccgcc tgcagaggag 1080
ggagccgaac ccgaggtggg agagaagaag gaggaagcag agaggctgac cacggaggag 1140
caggagaagg tggccgtgcc agagggggag aaagtagaga cccccggagt ggataaggag 1200
ggtgaaaaag aagagccgca gtcggagaag gtgtcaaagc aagggctgcc agctgagaag 1260
acaccttcac tctgtccaga gctgacaaca gatgatgcca gacccctgag caggctaagc 1320
aaagccagca gccgagccag gtcagacgat ctaaccgtat ga 1362

<210> SEQ ID NO 18
<211> LENGTH: 966
<212> TYPE: DNA
<213> ORGANISM: Homo sapiens

<400> SEQUENCE: 18
atgggggaat ggaccatctt ggagaggctg ctagaagccg cggtgcagca gcactccact 60
atgatcggaa ggatcctgtt gactgtggtg gtgatcttcc ggatcctcat tgtggccatt 120
gtgggggaga cggtgtacga tgatgagcag accatgtttg tgtgcaacac cctgcagccc 180
ggctgtaacc aggcctgcta tgaccgggcc ttccccatct cccacatacg ttactgggtc 240
ttccagatca taatggtgtg tacccccagt ctttgcttca tcacctactc tgtgcaccag 300
tccgccaagc agcgagaacg ccgctactct acagtcttcc tagccctgga cagagacccc 360
cctgagtcca taggaggtcc tggaggaact gggggtgggg gcagtggtgg gggcaaacga 420
gaagataaga agttgcaaaa tgctattgtg aatggggtgc tgcagaacac agagaacacc 480
agtaaggaga cagagccaga ttgtttagag gttaaggagc tgactccaca cccatcaggt 540
ctacgcactg catcaaaatc caagctcaga aggcaggaag gcatctcccg cttctacatt 600
atccaagtgg tgttccgaaa tgccctggaa attgggttcc tggttggcca atattttctc 660
tatggcttta gtgtcccagg gttgtatgag tgtaaccgct accccctgcat caaggaggtg 720 gaatgttatg tgtcccggcc aactgagaag actgtctttc tagtgttcat gtttgctgta 780
agtggcatct gtgttgtgct caacctggct gaactcaacc acctgggatg gcgcaagatc 840
aagctggctg tgcgaggggc tcaggccaag agaaagtcaa tctatgagat tcgtaacaag 900
gacctgccaa gggtcagtgt tcccaatttt ggcaggactc agtccagtga ctctgcctat 960
gtgtga 966

<210> SEQ ID NO 19
<211> LENGTH: 1901
<212> TYPE: DNA
<213> ORGANISM: Homo sapiens

<400> SEQUENCE: 19
cagggagttg tggttgcaac actgtactcc agcctgggca acagagggag actctgtctc 60
aacaaacaaa caaacaaaga aaaaacccca cagctatcta gggaaaaagt aaagcaacca 120
gcatatagaa gtgacatatt gttatatttt caccataggt ttgctttaag aaatagtgct 180
cccttcagaa tggaagaatt tatctgcctc ttatttgatg tggatcagag ctaagatggc 240
tgactaaata aacatggggg actggaatct ccttggagat actctggagg aagttcacat 300

-continued

```
ccactccacc atgattggaa agatctggct caccatcctg ttcatatttc gaatgcttgt    360
tctgggtgta gcagctgaag atgtctggaa tgatgagcag tctggcttca tctgcaatac    420
agaacaacca ggctgcagaa atgtatgcta cgaccaggcc tttcctatct ccctcattag    480
atactgggtt ctgcaggtga tatttgtgtc ttcaccatcc ctggtctaca tgggccatgc    540
attgtaccga ctgagagttc ttgaggaaga gaggcaaagg atgaaagctc agttaagagt    600
agaactggag gaggtagagt ttgaaatgcc tagggatcgg aggagattgg agcaagagct    660
ttgtcagctg gagaaaagga aactaaataa agctccactc agaggaacct tgctttgcac    720
ttatgtgata cacattttca ctcgctctgt ggttgaagtt ggattcatga ttggacagta    780
ccttttatat ggatttcact tagagccgct atttaagtgc catggccacc cgtgtccaaa    840
tataatcgac tgttttgtct caagaccaac agaaaagaca atattcctat tatttatgca    900
atctatagcc actatttcac ttttcttaaa cattcttgaa attttccacc taggttttaa    960
aaagattaaa agagggcttt ggggaaaata caagttgaag aaggaacata atgaattcca   1020
tgcaaacaag gcaaaacaaa atgtagccaa ataccagagc acatctgcaa attcactgaa   1080
gcgactccct tctgcccctg attataatct gttagtggaa aagcaaacac acactgcagt   1140
gtaccctagt ttaaattcat cttctgtatt ccagccaaat cctgacaatc atagtgtaaa   1200
tgatgagaaa tgcattttgg atgaacagga aactgtactt tctaatgaga tttccacact   1260
tagtactagt tgtagtcatt ttcaacacat cagttcaaac aataacaaag acactcataa   1320
aatatttgga aaagaactta atggtaacca gttaatggaa aaaagagaaa ctgaaggcaa   1380
agacagcaaa aggaactact actctagagg tcaccgttct attccaggtg ttgctataga   1440
tggagagaac aacatgaggc agtcacccca aacagttttc tccttgccag ctaactgcga   1500
ttggaaaccg cggtggctta gagctacatg ggttcctct acagaacatg aaaaccgggg   1560
gtcacctcct aaaggtaacc tcaagggcca gttcagaaag ggcacagtca gaacccttcc   1620
tccttcacaa ggagattctc aatcacttga cattccaaac actgctgatt ctttgggagg   1680
gctgtccttt gagccagggt tggtcagaac ctgtaataat cctgtttgtc ctccaaatca   1740
cgtagtgtcc ctaacgaaca atctcattgg taggcgggtt cccacagatc ttcagatcta   1800
aacagcggtt ggcttttaga cattatatat attatcagag aagtagccta gtggtcgtgg   1860
ggcacagaaa aaatagatag gggcagctct aaagaccagc t                        1901
```

<210> SEQ ID NO 20
<211> LENGTH: 1311
<212> TYPE: DNA
<213> ORGANISM: Homo sapiens

<400> SEQUENCE: 20

```
atgagctgga gcttcctgac gcggctgctg gaggagatcc acaaccactc caccttcgtg     60
ggcaaggtgt ggctcacggt gctggtggtc ttccgcatcg tgctgacggc tgtgggcggc    120
gaggccatct actcggacga gcaggccaag ttcacttgca acacgcggca gccaggctgc    180
gacaacgtct gctatgacgc cttcgcgccc ctgtcgcacg tgcgcttctg ggtcttccag    240
attgtggtca tctccacgcc ctcggtcatg tacctgggct acgccgtgca ccgcctggcc    300
cgtgcgtctg agcaggagcg gcgccgcgcc ctccgccgcc gcccggggcc acgccgcgcg    360
ccccgagcgc acctgccgcc cccgcacgcc ggctggcctg agcccgccga cctgggcgag    420
gaggagccca tgctgggcct gggcgaggag gaggaggagg aggagacggg ggcagccgag    480
```

-continued

```
ggcgccggcg aggaagcgga ggaggcaggc gcggaggagg cgtgcactaa ggcggtcggc    540

gctgacggca aggcggcagg gaccccgggc ccgaccgggc aacacgatgg gcggaggcgc    600

atccagcggg agggcctgat gcgcgtgtac gtggcccagc tggtggccag ggcagctttc    660

gaggtggcct tcctggtggg ccagtacctg ctgtacggct tcgaggtgcg accgttcttt    720

ccctgcagcc gccagccctg cccgcacgtg gtggactgct tcgtgtcgcg ccctactgaa    780

aagacggtct tcctgctggt tatgtacgtg gtcagctgcc tgtgcctgct gctcaacctc    840

tgtgagatgg cccacctggg cttgggcagc gcgcaggacg cggtgcgcgg ccgccgcggc    900

cccccggcct ccgcccccgc ccccgcgccg cggcccccgc cctgcgcctt ccctgcggcg    960

gccgctggct tggcctgccc gcccgactac agcctggtgg tgcgggcggc cgagcgcgct   1020

cgggcgcatg accagaacct ggcaaacctg gccctgcagg cgctgcgcga cggggcagcg   1080

gctggggacc gcgaccggga cagttcgccg tgcgtcggcc tccctgcggc ctcccggggg   1140

ccccccagag caggcgcccc cgcgtcccgg acgggcagtg ctacctctgc gggcactgtc   1200

ggggagcagg gccggcccgg cacccacgag cggccaggag ccaagcccag ggctggctcc   1260

gagaagggca gtgccagcag cagggacggg aagaccaccg tgtggatctg a            1311
```

<210> SEQ ID NO 21
<211> LENGTH: 1588
<212> TYPE: DNA
<213> ORGANISM: Homo sapiens

<400> SEQUENCE: 21

```
agacattctc tgggaaaggg cagcagcagc caggtgtggc agtgacaggg aggtgtgaat     60

gaggcaggat gaactggaca ggtttgtaca ccttgctcag tggcgtgaac cggcattcta    120

ctgccattgg ccgagtatgg ctctcggtca tcttcatctt cagaatcatg gtgctggtgg    180

tggctgcaga gagtgtgtgg ggtgatgaga aatcttcctt catctgcaac acactccagc    240

ctggctgcaa cagcgtttgc tatgaccaat tcttccccat ctcccatgtg cggctgtggt    300

ccctgcagct catcctagtt tccaccccag ctctcctcgt ggccatgcac gtggctcacc    360

agcaacacat agagaagaaa atgctacggc ttgagggcca tggggacccc ctacacctgg    420

aggaggtgaa gaggcacaag gtccacatct cagggacact gtggtggacc tatgtcatca    480

gcgtggtgtt ccggctgttg tttgaggccg tcttcatgta tgtcttttat ctgctctacc    540

ctggctatgc catggtgcgg ctggtcaagt gcgacgtcta cccctgcccc aacacagtgg    600

actgcttcgt gtcccgcccc accgagaaaa ccgtcttcac cgtcttcatg ctagctgcct    660

ctggcatctg catcatcctc aatgtggccg aggtggtgta cctcatcatc cgggcctgtg    720

cccgccgagc ccagcgccgc tccaatccac cttcccgcaa gggctcgggc ttcggccacc    780

gcctctcacc tgaatacaag cagaatgaga tcaacaagct gctgagtgag caggatggct    840

ccctgaaaga catactgcgc cgcagccctg gcaccggggc tgggctggct gaaaagagcg    900

accgctgctc ggcctgctga tgccacatac caggcaacct cccatcccac cccccgaccct    960

gccctgggcg agcccctcct tctcccctgc cggtgcacag gcctctgcct gctggggatt   1020

actcgatcaa aaccttcctt ccctggctac ttcccttcct cccggggcct tccttttgag   1080

gagctggagg ggtggggagc tagaggccac ctatgccagt gctcaaggtt actgggagtg   1140

tgggctgccc ttgttgcctg cacccttccc tcttccctct ccctctctct gggaccactg   1200

ggtacaagag atgggatgct ccgacagcgt ctccaattat gaaactaatc ttaaccctgt   1260

gctgtcagat accctgtttc tggagtcaca tcagtgagga gggatgtggg taagaggagc   1320
```

-continued agagggcagg ggtgctgtgg acatgtgggt ggagaaggga gggtggccag cactagtaaa 1380
ggaggaatag tgcttgctgg ccacaaggaa aaggaggagg tgtctggggt gagggagtta 1440
gggagagaga agcaggcaga taagttggag caggggttgg tcaaggccac ctctgcctct 1500
agtccccaag gcctctctct gcctgaaatg ttacacatta aacaggattt tacagcaaaa 1560
aaaaaaaaaa aaaaaaaaaa aaaaaaaa 1588

<210> SEQ ID NO 22
<211> LENGTH: 2263
<212> TYPE: DNA
<213> ORGANISM: Homo sapiens

<400> SEQUENCE: 22
cggagcccct cggcggcgcc cggcccagga cccgcctagg agcgcaggag ccccagcgca 60
gagaccccaa cgccgagacc cccgccccgg ccccgccgcg cttcctcccg acgcagagca 120
aaccgcccag agtagaagat ggattggggc acgctgcaga cgatcctggg gggtgtgaac 180
aaacactcca ccagcattgg aaagatctgg ctcaccgtcc tcttcatttt tcgcattatg 240
atcctcgttg tggctgcaaa ggaggtgtgg ggagatgagc aggccgactt tgtctgcaac 300
accctgcagc caggctgcaa gaacgtgtgc tacgatcact acttccccat ctcccacatc 360
cggctatggg ccctgcagct gatcttcgtg tccacgccag cgctcctagt ggccatgcac 420
gtggcctacc ggagacatga gaagaagagg aagttcatca agggggagat aaagagtgaa 480
tttaaggaca tcgaggagat caaaacccag aaggtccgca tcgaaggctc cctgtggtgg 540
acctacacaa gcagcatctt cttccgggtc atcttcgaag ccgccttcat gtacgtcttc 600
tatgtcatgt acgacggctt ctccatgcag cggctggtga agtgcaacgc ctggccttgt 660
cccaacactg tggactgctt tgtgtcccgg cccacggaga agactgtctt cacagtgttc 720
atgattgcag tgtctggaat ttgcatcctg ctgaatgtca ctgaattgtg ttatttgcta 780
attagatatt gttctgggaa gtcaaaaaag ccagtttaac gcattgccca gttgttagat 840
taagaaatag acagcatgag agggatgagg caacccgtgc tcagctgtca aggctcagtc 900
gccagcattt cccaacacaa agattctgac cttaaatgca accatttgaa acccctgtag 960
gcctcaggtg aaactccaga tgccacaatg gagctctgct cccctaaagc ctcaaaacaa 1020
aggcctaatt ctatgcctgt cttaattttc tttcacttaa gttagttcca ctgagacccc 1080
aggctgttag gggttattgg tgtaaggtac tttcatattt taaacagagg atatcggcat 1140
ttgtttcttt ctctgaggac aagagaaaaa agccaggttc cacagaggac acagagaagg 1200
tttgggtgtc ctcctggggt tctttttgcc aactttcccc acgttaaagg tgaacattgg 1260
ttctttcatt tgctttggaa gttttaatct ctaacagtgg acaaagttac cagtgcctta 1320
aactctgtta cactttttgg aagtgaaaac tttgtagtat gataggttat tttgatgtaa 1380
agatgttctg gataccatta tatgttcccc ctgtttcaga ggctcagatt gtaatatgta 1440
aatggtatgt cattcgctac tatgatttaa tttgaaatat ggtcttttgg ttatgaatac 1500
tttgcagcac agctgagagg ctgtctgttg tattcattgt ggtcatagca cctaacaaca 1560
ttgtagcctc aatcgagtga gacagactag aagttcctag tgatggctta tgatagcaaa 1620
tggcctcatg tcaaatattt agatgtaatt ttgtgtaaga aatacagact ggatgtacca 1680
ccaactacta cctgtaatga caggcctgtc caacacatct cccttttcca tgactgtggt 1740
agccagcatc ggaaagaacg ctgatttaaa gaggtcgctt gggaatttta ttgacacagt 1800

-continued

```
accatttaat ggggaggaca aaatggggca ggggagggag aagtttctgt cgttaaaaac   1860

agatttggaa agactggact ctaaattctg ttgattaaag atgagctttg tctacttcaa   1920

aagtttgttt gcttacccct tcagcctcca attttttaag tgaaaatata actaataaca   1980

tgtgaaaaga atagaagcta aggtttagat aaatattgag cagatctata ggaagattga   2040

acctgaatat tgccattatg cttgacatgg tttccaaaaa atggtactcc acatacttca   2100

gtgagggtaa gtattttcct gttgtcaaga atagcattgt aaaagcattt tgtaataata   2160

aagaatagct ttaatgatat gcttgtaact aaaataattt tgtaatgtat caaatacatt   2220

taaaacatta aaatataatc tctataataa aaaaaaaaaa aaa                     2263


<210> SEQ ID NO 23
<211> LENGTH: 2220
<212> TYPE: DNA
<213> ORGANISM: Homo sapiens

<400> SEQUENCE: 23

gaacttcttt cctggcacag gactcactgt gccccttccc gctgtgggta caaggtctgc     60

cccccacccc agctctccaa agcccaccgg cctccctgga ggccgaggtc gacggcccgt    120

cgcaccggga ggggggctc ccaggggtgc cccacgcacg gtcaaggtcc cgcgccaagc    180

ggggaccggg ctgggccgga agcgggcacg gtactcgcgg caaactagcg tgggcgagtc    240

ctgattgcag tcggacctgc cgccgcggca cttaacagtt tgcagagtgc ttcccgcccc    300

tgatctcatt ggagccttcg gacagcccag cccatggcca ccgatgcccc catttcacgc    360

ctgaggaagc ggaggctcag acgggccacc agcccctccg gaggctggcc cgggagcgcc    420

tggcagcgtc gggtctagga gccggctccc tcctgctccc tcctccgcgc cgcccggggt    480

gtgcccgccg tctgtgtgca ccactgctga gcccagctcc ggcgccctcg cctctgctgt    540

gggcccccggg gacgcggggt caggccaccg cgttggccag gccgctgcag gtaggcacgg    600

cccccaccag gcgccatgga ctggaagaca ctccaggccc tactgagcgg tgtgaacaag    660

tactccacag cgttcgggcg catctggctg tccgtggtgt tcgtcttccg ggtgctggta    720

tacgtggtgg ctgcagagcg cgtgtggggg gatgagcaga aggactttga ctgcaacacc    780

aagcagcccg gctgcaccaa cgtctgctac gacaactact tccccatctc caacatccgc    840

ctctgggccc tgcagctcat cttcgtcaca tgcccctcgc tgctggtcat cctgcacgtg    900

gcctaccgtg aggagcggga gcgccggcac cgccagaaac acggggacca gtgcgccaag    960

ctgtacgaca acgcaggcaa gaagcacgga ggcctgtggt ggacctacct gttcagcctc   1020

atcttcaagc tcatcattga gttcctcttc ctctacctgc tgcacactct ctggcatggc   1080

ttcaatatgc cgcgcctggt gcagtgtgcc aacgtggccc cctgccccaa catcgtggac   1140

tgctacattg cccgacctac cgagaagaaa atcttcacct acttcatggt gggcgcctcc   1200

gccgtctgca tcgtactcac catctgtgag ctctgctacc tcatctgcca cagggtcctg   1260

cgaggcctgc acaaggacaa gcctcgaggg ggttgcagcc cctcgtcctc cgccagccga   1320

gcttccacct gccgctgcca ccacaagctg gtggaggctg gggaggtgga tccagaccca   1380

ggcaataaca agctgcaggc ttcagcaccc aacctgaccc ccatctgacc acagggcagg   1440

ggtggggcaa catgcgggct gccaatggga catgcagggc ggtgtggcag gtggagaggt   1500

cctacagggg ctgagtgacc ccactctgag ttcactaagt tatgcaactt tcgttttggc   1560

agatattttt tgacactggg aactgggctg tctagccggg tataggtaac ccacaggccc   1620

agtgccagcc ctcaaaggac atagactttg aaacaagcga attaactatc tacgctgcct   1680
```

gcaaggggcc acttagggca ctgctagcag ggcttcaacc aggaagggat caacccagga 1740
agggatgatc aggagaggct tccctgagga cataatgtgt aagagaggtg agaagtgctc 1800
ccaagcagac acaacagcag cacagaggtc tggaggccac acaaaaagtg atgctcgccc 1860
tgggctagcc tcagcagacc taaggcatct ctactccctc cagaggagcc gcccagattc 1920
ctgcagtgga gaggaggtct tccagcagca gcaggtctgg agggctgaga atgaacctga 1980
ctagaggttc tggagatacc cagaggtccc ccaggtcatc acttggctca gtggaagccc 2040
tctttcccca aatcctactc cctcagcctc aggcagtggt gctcccatct tcctccccac 2100
aactgtgctc aggctggtgc cagcctttca gaccctgctc ccagggactt gggtggatgc 2160
gctgatagaa catcctcaag acagtttcct tgaaatcaat aaatactgtg ttttataaaa 2220

<210> SEQ ID NO 24
<211> LENGTH: 1243
<212> TYPE: DNA
<213> ORGANISM: Homo sapiens

<400> SEQUENCE: 24
caaggctccc aaggcctgag tgggcaggta gcacccaggt atagaccttc cacgtgcagc 60
acccaggaca cagccagcat gaactgggca tttctgcagg gcctgctgag tggcgtgaac 120
aagtactcca cagtgctgag ccgcatctgg ctgtctgtgg tgttcatctt tcgtgtgctg 180
gtgtacgtgg tggcagcgga ggaggtgtgg gacgatgagc agaaggactt tgtctgcaac 240
accaagcagc ccggctgccc caacgtctgc tatgacgagt tcttccccgt gtcccacgtg 300
cgcctctggg ccctacagct catcctggtc acgtgcccct cactgctcgt ggtcatgcac 360
gtggcctacc gcgaggaacg cgagcgcaag caccacctga aacacgggcc caatgccccg 420
tccctgtacg acaacctgag caagaagcgg ggcggactgt ggtggacgta cttgctgagc 480
ctcatcttca aggccgccgt ggatgctggc ttcctctata tcttccaccg cctctacaag 540
gattatgaca tgccccgcgt ggtggcctgc tccgtggagc cttgccccca cactgtggac 600
tgttacatct cccggcccac ggagaagaag gtcttcacct acttcatggt gaccacagct 660
gccatctgca tcctgctcaa cctcagtgaa gtcttctacc tggtgggcaa gaggtgcatg 720
gagatcttcg gccccaggca ccggcggcct cggtgccggg aatgcctacc cgatacgtgc 780
ccaccatatg tcctctccca gggagggcac cctgaggatg ggaactctgt cctaatgaag 840
gctgggtcgg ccccagtgga tgcaggtggg tatccataac ctgcgagatc agcagataag 900
atcaacaggt ccccccccaca tgaggccacc caggaaaaaa ggcaggggca gtggcatcct 960
tgccgtagca gggtggtgag gagggtggct gtgggggctc aggaagctcg cccaggggcc 1020
aatgtgggag gttgggggta gtttggtccc tgggtcctga gcctcagggg agggaggttg 1080
atagctactg ggattttgt atatggcaac agtatatgtc aaacctctta ttaaatatga 1140
ttttcccagt aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaa 1243

<210> SEQ ID NO 25
<211> LENGTH: 1299
<212> TYPE: DNA
<213> ORGANISM: Homo sapiens

<400> SEQUENCE: 25
atgaaattca agctgcttgc tgagtcctat tgccggctgc tgggagccag gagagccctg 60

```
aggagtagtc actcagtagc agctgacgcg tgggtccacc atgaactgga gtatctttga    120
gggactcctg agtggggtca acaagtactc cacagccttt gggcgcatct ggctgtctct    180
ggtcttcatc ttccgcgtgc tggtgtacct ggtgacggcc gagcgtgtgt ggagtgatga    240
ccacaaggac ttcgactgca atactcgcca gcccggctgc tccaacgtct gctttgatga    300
gttcttccct gtgtcccatg tgcgcctctg ggccctgcag cttatcctgg tgacatgccc    360
ctcactgctc gtggtcatgc acgtggccta ccgggaggtt caggagaaga ggcaccgaga    420
agcccatggg gagaacagtg ggcgcctcta cctgaacccc ggcaagaagc ggggtgggct    480
ctggtggaca tatgtctgca gcctagtgtt caaggcgagc gtggacatcg cctttctcta    540
tgtgttccac tcattctacc ccaaatatat cctccctcct gtggtcaagt gccacgcaga    600
tccatgtccc aatatagtgg actgcttcat ctccaagccc tcagagaaga acattttcac    660
cctcttcatg gtggccacag ctgccatctg catcctgctc aacctcgtgg agctcatcta    720
cctggtgagc aagagatgcc acgagtgcct ggcagcaagg aaagctcaag ccatgtgcac    780
aggtcatcac ccccacggta ccacctcttc ctgcaaacaa gacgacctcc tttcgggtga    840
cctcatcttt ctgggctcag acagtcatcc tcctctctta ccagaccgcc cccgagacca    900
tgtgaagaaa accatcttgt gaggggctgc ctggactggt ctggcaggtt gggcctggat    960
ggggaggctc tagcatctct cataggtgca acctgagagt gggggagcta agccatgagg   1020
taggggcagg caagagagag gattcagacg ctctgggagc cagttcctag tcctcaactc   1080
cagccacctg ccccagctcg acggcactgg gccagttccc cctctgctct gcagctcggt   1140
ttccttttct agaatggaaa tagtgagggc caatgcccag ggttggaggg aggagggcgt   1200
tcatagaaga acacacatgc gggcaccttc atcgtgtgtg gcccactgtc agaacttaat   1260
aaaagtcaac tcatttgctg gaaaaaaaaa aaaaaaaaa                          1299
```

<210> SEQ ID NO 26
<211> LENGTH: 1805
<212> TYPE: DNA
<213> ORGANISM: Homo sapiens

<400> SEQUENCE: 26

```
ctgggaagac gctggtcagt tcacctgccc cactggttgt tttttaaaca aattctgata     60
caggcgacat cctcactgac cgagcaaaga ttgacattcg tatcatcact gtgcaccatt    120
ggcttctagg cactccagtg ggtaggaga aggaggtctg aaaccctcgc agagggatct    180
tgccctcatt ctttgggtct gaaacactgg cagtcgttgg aaacaggact cagggataaa    240
ccagcgcaat ggattggggg acgctgcaca ctttcatcgg gggtgtcaac aaacactcca    300
ccagcatcgg gaaggtgtgg atcacagtca tctttatttt ccgagtcatg atcctcgtgg    360
tggctgccca ggaagtgtgg ggtgacgagc aagaggactt cgtctgcaac acactgcaac    420
cgggatgcaa aaatgtgtgc tatgaccact tttcccggt gtcccacatc cggctgtggg    480
ccctccagct gatcttcgtc tccaccccag cgctgctggt ggccatgcat gtggcctact    540
acaggcacga aaccactcgc aagttcaggc gaggagagaa gaggaatgat ttcaaagaca    600
tagaggacat taaaaagcag aaggttcgga tagaggggtc gctgtggtgg acgtacacca    660
gcagcatctt tttccgaatc atctttgaag cagcctttat gtatgtgttt tacttccttt    720
acaatgggta ccacctgccc tgggtgttga aatgtgggat tgacccctgc cccaaccttg    780
ttgactgctt tatttctagg ccaacagaga agaccgtgtt taccattttt atgatttctg    840
cgtctgtgat ttgcatgctg cttaacgtgg cagagttgtg ctacctgctg ctgaaagtgt    900
```

```
gttttaggag atcaaagaga gcacagacgc aaaaaaatca ccccaatcat gccctaaagg    960

agagtaagca gaatgaaatg aatgagctga tttcagatag tggtcaaaat gcaatcacag   1020

gtttcccaag ctaaacattt caaggtaaaa tgtagctgcg tcataaggag acttctgtct   1080

tctccagaag gcaataccaa cctgaaagtt ccttctgtag cctgaagagt ttgtaaatga   1140

ctttcataat aaatagacac ttgagttaac tttttgtagg atacttgctc cattcataca   1200

caacgtaatc aaatatgtgg tccatctctg aaaacaagag actgcttgac aaaggagcat   1260

tgcagtcact ttgacaggtt ccttttaagt ggactctctg acaaagtggg tactttctga   1320

aaatttatat aactgttgtt gataaggaac atttatccag gaattgatac ttttattagg   1380

aaaagatatt tttataggct tggatgtttt tagttctgac tttgaattta tataaagtat   1440

ttttataatg actggtcttc cttacctgga aaaacatgcg atgttagttt tagaattaca   1500

ccacaagtat ctaaatttgg aacttacaaa gggtctatct tgtaaatatt gttttgcatt   1560

gtctgttggc aaatttgtga actgtcatga tacgcttaag gtggaaagtg ttcattgcac   1620

aatatatttt tactgctttc tgaatgtaga cggaacagtg tggaagcaga aggctttttt   1680

aactcatccg tttgccaatc attgcaaaca actgaaatgt ggatgtgatt gcctcaataa   1740

agctcgtccc cattgcttaa gccttcaaaa aaaaaaaaaa aaaaaaaaaa aaaaaaaaaa   1800

aaaaa                                                               1805
```

<210> SEQ ID NO 27
<211> LENGTH: 2094
<212> TYPE: DNA
<213> ORGANISM: Homo sapiens

<400> SEQUENCE: 27

```
aaatgaaaga gggagcagga ggcgccggtc ccagccacct cccaaggtcc ctggctcagc     60

tctgacaccc cagtcccggc cccagggtga gtggggttgg gtggcggttt aggggcacca    120

ggggcgtgtg gggacctgtg taagtgtggg gtggggagga tctcaggaga tgtggaggct    180

ggaggcacag gaggccaggg aggagggaga agcctggtgc cgcactccca ccacgctggg    240

gtaggagggc agggacacct ccgacaaagg accctgtgag agttatgaaa gcggagttgc    300

ctctgtacca gccccccacc ctgagaggag ttcactgcag taaaaatggt gagagaaatg    360

gtgggccaag aaaggagtgg tctcgctgcc tctgccactc ccactcctcc catgggcacc    420

aaattgggtc tagcgtctcg ggttcgaggc tccactcttc ccacagcatc cttgacagct    480

aagggcaccg ctgggtttcc gcttccgaaa ccaggcaagt caggggctgg tccagctgat    540

ctccaaggtc cttcctaaga atctgggatc tggaggatcc cagggtcgaa cggagacggc    600

tcagggggtg cggctaaaat gcaaatgggg gatcctcccc agcacccatc ggtcccaaag    660

agaaggtaac ccatagctga gcgtcgcctg ctcccctcgg gccctcccgt ggccctccgt    720

ttcatactgg tctcatcgct aaacccgggc ctctcctacc tcacgactca ccctgaagtc    780

agagaaggtc caacggaccc caccccgata ggcttggaag gggcaggggt ccctgacttg    840

ccccatcccc tgactccccg ccccgcgtcc ccagcgccat gggggagtgg gcgttcctgg    900

gctcgctgct ggacgccgtg cagctgcagt cgccgctcgt gggccgcctc tggctggtgg    960

tcatgctgat cttccgcatc ctggtgctgg ccacggtggg cggcgccgtg ttcgaggacg   1020

agcaagagga gttcgtgtgc aacacgctgc agccgggctg tcgccagacc tgctacgacc   1080

gcgccttccc ggtctcccac taccgcttct ggctcttcca catcctgctg ctctcggcgc   1140
```

-continued ccccggtgct gttcgtcgtc tactccatgc accgggcagg caaggaggcg ggcggcgctg 1200
aggcggcggc gcagtgcgcc cccggactgc ccgaggccca gtgcgcgccg tgcgccctgc 1260
gcgcccgccg cgcgcgccgc tgctacctgc tgagcgtggc gctgcgcctg ctggccgagc 1320
tgaccttcct gggcggccag gcgctgctct acggcttccg cgtggccccg cacttcgcgt 1380
gcgccggtcc gccctgcccg cacacggtcg actgcttcgt gagccggccc accgagaaga 1440
ccgtcttcgt gctcttctat ttcgcggtgg ggctgctgtc ggcgctgctc agcgtagccg 1500
agctgggcca cctgctctgg aagggccgcc cgcgcgccgg ggagcgtgac aaccgctgca 1560
accgtgcaca cgaagaggcg cagaagctgc tcccgccgcc gccgccgcca cctattgttg 1620
tcacttggga agaaaacaga caccttcaag gagagggctc ccctggtagc ccccacccca 1680
agacagagct ggatgcccct cgcttccgta gggaaagcac ttctcctgca ggatggcatt 1740
gctctctccc cttccatggc acgtagtatg tgctcagtaa atatgtgttg gatgagaaac 1800
tgaaggtgtc cccaggccta caccactgcc atgcccgaac actatccatg ctatggtggg 1860
caccatctct ctgatgacag ttctgtgtcc acaacccaga cccctccaca caaacccaga 1920
tggggctgtg ccgctgtttt ccagatgtat tcattcaaca aatatttgta gggtacctac 1980
tgtgtgtcag aagatgttca agatcagcat catccgatgg aaatagcata tgagccatgt 2040
atgtagtttc aagtttttca ttagccgcat taaaaaagta aaaggaaaca aatg 2094

<210> SEQ ID NO 28
<211> LENGTH: 840
<212> TYPE: DNA
<213> ORGANISM: Homo sapiens

<400> SEQUENCE: 28
atgtgtggca ggttcctgcg gcggctgctg gcggaggaga gccggcgctc cacccccgtg 60
gggcgcctct tgcttcccgt gctcctggga ttccgccttg tgctgctggc tgccagtggg 120
cctggagtct atggtgatga gcagagtgaa ttcgtgtgtc acacccagca gccgggctgc 180
aaggctgcct gcttcgatgc cttccacccc ctctccccgc tgcgtttctg ggtcttccag 240
gtcatcttgg tggctgtacc cagcgccctc tatatgggtt tcactctgta tcacgtgatc 300
tggcactggg aattatcagg aaaggggaag gaggaggaga ccctgatcca gggacgggag 360
ggcaacacag atgtcccagg ggctggaagc ctcaggctgc tctgggctta tgtggctcag 420
ctgggggctc ggcttgtcct ggagggggca gccctggggt tgcagtacca cctgtatggg 480
ttccagatgc ccagctcctt tgcatgtcgc cgagaacctt gccttggtag tataacctgc 540
aatctgtccc gcccctctga gaagaccatt ttcctaaaga ccatgtttgg agtcagcggt 600
ttctgtctct tgtttacttt tttggagctt gtgcttctgg gtttggggag atggtggagg 660
acctggaagc acaaatcttc ctcttctaaa tacttcctaa cttcagagag caccagaaga 720
cacaagaaag caaccgatag cctcccagtg gtggaaacca aagagcaatt tcaagaagca 780
gttccaggaa gaagcttagc ccaggaaaaa caaagaccag ttggacccag agatgcctga 840

<210> SEQ ID NO 29
<211> LENGTH: 672
<212> TYPE: DNA
<213> ORGANISM: Homo sapiens

<400> SEQUENCE: 29
atgagttgga tgttcctcag agatctcctg agtggagtaa ataaatactc cactgggact 60
ggatggattt ggctggctgt cgtgtttgtc ttccgtttgc tggtctacat ggtggcagca 120
gagcacatgt ggaaagatga gcagaaagag tttgagtgca acagtagaca gcccggttgc 180
aaaaatgtgt gttttgatga cttcttcccc atttcccaag tcagactttg ggccttacaa 240
ctgataatgg tctccacacc ttcacttctg gtggttttac atgtagccta tcatgagggt 300
agagagaaaa ggcacagaaa gaaactctat gtcagcccag gtacaatgga tgggggccta 360
tggtacgctt atcttatcag cctcattgtt aaaactggtt ttgaaattgg cttccttgtt 420
ttattttata agctatatga tggctttagt gttccctacc ttataaagtg tgatttgaag 480
ccttgtccca acactgtgga ctgcttcatc tccaaaccca ctgagaagac gatcttcatc 540
ctcttcttgg tcatcacctc atgcttgtgt attgtgttga atttcattga actgagtttt 600
ttggttctca agtgctttat taagtgctgt ctccaaaaat atttaaaaaa acctcaagtc 660
ctcagtgtgt ga 672

<210> SEQ ID NO 30
<211> LENGTH: 1113
<212> TYPE: DNA
<213> ORGANISM: Homo sapiens

<400> SEQUENCE: 30
atggaaggcg tggacttgct agggtttctc atcatcacat taaactgcaa cgtgaccatg 60
gtaggaaagc tctggttcgt cctcacgatg ctgctgcgga tgctggtgat tgtcttggcg 120
gggcgacccg tctaccagga cgagcaggag aggtttgtct gcaacacgct gcagccggga 180
tgcgccaatg tttgctacga cgtcttctcc cccgtgtctc acctgcggtt ctggctgatc 240
cagggcgtgt gcgtcctcct cccctccgcc gtcttcagcg tctatgtcct gcaccgagga 300
gccacgctcg ccgcgctggg cccccgccgc tgccccgacc cccgggagcc ggcctccggg 360
cagagacgct gcccgcggcc attcggggag cgcggcggcc tccaggtgcc cgacttttcg 420
gccggctaca tcatccacct cctcctccgg accctgctgg aggcagcctt cggggccttg 480
cactactttc tctttggatt cctggccccg aagaagttcc cttgcacgcg ccctccgtgc 540
acgggcgtgg tggactgcta cgtgtcgcgg cccacagaga agtccctgct gatgctgttc 600
ctctgggcgg tcagcgcgct gtcttttctg ctgggcctcg ccgacctggt ctgcagcctg 660
cggcggcgga tgcgcaggag gccgggaccc cccacaagcc cctccatccg gaagcagagc 720
ggagcctcag gccacgcgga gggacgccgg actgacgagg agggtgggcg ggaggaagag 780
ggggcaccgg cgcccccggg tgcacgcgcc ggaggggagg gggctggcag ccccaggcgt 840
acatccaggg tgtcagggca cacgaagatt ccggatgagg atgagagtga ggtgacatcc 900
tccgccagcg aaaagctggg cagacagccc cggggcaggc cccaccgaga ggccgcccag 960
gaccccaggg gctcaggatc cgaggagcag ccctcagcag cccccagccg cctggccgcg 1020 ccccccttcct gcagcagcct gcagcccccct gacccgcctg ccagctccag tggtgctccc 1080
cacctgagag ccaggaagtc tgagtgggtg tga 1113

<210> SEQ ID NO 31
<211> LENGTH: 1632
<212> TYPE: DNA
<213> ORGANISM: Homo sapiens

<400> SEQUENCE: 31
atgggggact ggaacttatt gggtggcatc ctagaggaag ttcactccca ctcaaccata 60
gtggggaaaa tctggctgac catcctcttc atcttccgaa tgctggtact tcgtgtggct 120

-continued

```
gctgaggatg tctgggatga tgaacagtca gcatttgcct gcaacacccg gcagccaggt    180
tgcaacaata tctgttatga tgatgcattc cctatctctt tgatcaggtt ctgggtttta    240
cagatcatct ttgtgtcttc tccttctttg gtctatatgg gccatgcact ttataggctc    300
agggcctttg agaaagacag gcagaggaaa aagtcacacc ttagagccca gatggagaat    360
ccagatcttg acttggagga gcagcaaaga atagataggg aactgaggag gttagaggag    420
cagaagagga tccataaagt ccctctgaaa ggatgtctgc tgcgtactta tgtcttacac    480
atcttgacca gatctgtgct ggaagtagga ttcatgatag gccaatatat tctctatggg    540
tttcaaatgc accccttta caaatgcact caacctcctt gccccaatgc ggtggattgc    600
tttgtatcca ggcccactga gaagacaatt ttcatgcttt ttatgcacag cattgcagcc    660
atttccttgt tactcaatat actggaaata tttcatctag gcatcagaaa aattatgagg    720
acactttata agaaatccag cagtgagggc attgaggatg aaacaggccc tccattccat    780
ttgaagaaat attctgtggc ccagcagtgt atgatttgct cttcattgcc tgaaagaatc    840
tctccacttc aagctaacaa tcaacagcaa gtcattcgag ttaatgtgcc aaagtctaaa    900
accatgtggc aaatcccaca gccaaggcaa cttgaagtag acccttccaa tgggaaaaag    960
gactggtctg agaaggatca gcatagcgga cagctccatg ttcacagccc gtgtccctgg   1020
gctggcagtg ctggaaatca gcacctggga cagcaatcag accattcctc atttggcctg   1080
cagaatacaa tgtctcagtc ctggctaggt acaactacgg ctcctagaaa ctgtccatcc   1140
tttgcagtag gaacctggga gcagtcccag gacccagaac cctcaggtga gcctctcaca   1200
gatcttcata gtcactgcag agacagtgaa ggcagcatga gagagagtgg ggtctggata   1260
gacagatctc gcccaggcag tcgcaaggcc agctttctgt ccagattgtt gtctgaaaag   1320
cgacatctgc acagtgactc aggaagctct ggttctcgga atagctcctg cttggatttt   1380
cctcactggg aaaacagccc ctcacctctg ccttcagtca ctgggcacag aacatcaatg   1440
gtaagacagg cagccctacc gatcatggaa ctatcacaag agctgttcca ttctggatgc   1500
tttctttttc ctttctttct tcctggggtg tgtatgtatg tttgtgttga cagagaggca   1560
gatggagggg gagattattt atggagagat aaaattattc attcgataca ttcagttaaa   1620
ttcaattcat aa                                                       1632
```

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32

```
ccaaggcagg ctagctacaa cgatccagtc a                                    31
```

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33

```
ccgtgggagg ctagctacaa cgagtgagag g                                    31
```

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ccgtgggagg ctaactacaa cgagtgagag g 31

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
agtcttttgg gctagctaca acgatgggct ca 32

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
tttggagagg ctagctacaa cgaccgcagt c 31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
tttggagagg ctaactacaa cgaccgcagt c 31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
acgaggaagg ctagctacaa cgatgtttct g 31

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
ttgcggcggc tagctacaac gacgaggaat 30

<210> SEQ ID NO 40

<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
ccatgcgagg ctagctacaa cgatttgctc t 31

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
ttggtccagg ctagctacaa cgagatggct a 31

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
gtaattgcgg caggaggaat tgtttctgtc 30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
gacagaaaca attcctcctg ccgcaattac 30

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ccaaggcact ccagtcac 18

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tccgtgggac gtgagagga 19

<210> SEQ ID NO 46
<211> LENGTH: 18

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
agtcttttga tgggctca 18

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
ttttggagat ccgcagtct 19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
cacgaggaat tgtttctgt 19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
tttgcggcac gaggaatt 18

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
cccatgcgat tttgctctg 19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 51
gttggtccac gatggctaa 19

<210> SEQ ID NO 52
<211> LENGTH: 31
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 52
gttgcagagg ctagctacaa cgaaaaatcg g 31

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gttctttagg ctagctacaa cgactctccc t 31

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtccttaaag gctagctaca acgatcgttc ttt 33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tctcttcgag gctagctaca acgagtcctt aaa 33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tctcttcgag gctaactaca acgagtcctt aaa 33

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gatacggagg ctagctacaa cgacttctgg g 31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
cttcgatagg ctagctacaa cgaggacctt c 31

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
cttcgatagg ctaactacaa cgaggacctt c 31

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60
ggtgaagagg ctagctacaa cgaagtcttt tct 33

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
ccttaaactc gttctttatc tctcccttca 30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
acttccctct ctatttcttg ctcaaattcc 30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
tacggacctt ctgggttttg atctcttcga 30

<210> SEQ ID NO 64
<211> LENGTH: 30
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 64

agcttctcta gttttgggtc ttccaggcat                                      30


<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

gtaattgcgg caggaggaat tgtttctgtc                                      30


<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

ggctagctac aacga                                                      15


<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

ggctaactac aacga                                                      15
```

ANTI-CONNEXIN COMPOUNDS TARGETED TO CONNEXINS AND METHODS OF USE THEREOF

RELATED PATENT APPLICATIONS

This application is a divisional application of and claims benefit of priority under 35 U.S.C. § 119(e) to U.S. Utility application Ser. No. 13/230,744, entitled "ANTI-CONNEXIN COMPOUNDS TARGETED TO CONNEXINS AND METHODS OF USE THEREOF," filed on Sep. 12, 2011, which is a divisional of U.S. Utility application Ser. No. 10/581,813, entitled "ANTISENSE COMPOUNDS TARGETED TO CONNEXINS AND METHODS OF USE THEREOF," filed on Jan. 29, 2007, which claims benefit of National Stage Application under 35 U.S.C. § 371 of International Application No. PCT/162004/004431, entitled "ANTISENSE COMPOUNDS TARGETED TO CONNEXINS AND METHODS OF USE THEREOF," filed on Dec. 3, 2004, which claims the benefit of New Zealand Application No. 529936, entitled "TISSUE ENGINEERING OR REMODELING," filed on Dec. 3, 2003, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 29, 2014, is named E3697-00338_SL.txt and is 55,094 bytes in size.

TECHNICAL FIELD

The present disclosure relates to and describes agents, compositions and methods of using compounds for modulation of gap-junction-associated protein expression. These agents, compositions, and methods are useful, for example, for tissue engineering in vivo and in vitro, including for example in the skin, in corneal tissue, and conjunction with surgical procedures of the eye.

BACKGROUND

Tissue or organ failure due to illness or injury is a major health problem worldwide with little option for full recovery other than organ or tissue transplantation. However, problems finding a suitable donor mean that this option is not available to the majority of patients. tissue engineering or remodeling whereby synthetic or semi synthetic tissue or organ mimics that are either fully functional or which are grown in a desired functionality is currently being investigated as replacements.

One area in particular that this technology is becoming increasingly important is in the cornea of the eye. Corneal transplantation is the most common form of solid organ transplant performed worldwide. Each year around 80,000 are performed in the USA and the UK alone. The prevalence of refractive surgery for correction of myopia such as photorefractive keratectomy (PRK) and laser in situ keratomileusis (LASIK) has led to shortage of suitable cornea for transplant for tissue reconstruction after surgery or disease processes and for tissue manipulation in vivo to engineer changes. In addition, approximately 5% of patients undergoing laser surgery experience unexpected outcomes.

The cornea is a transparent tissue that comprises the central one sixth of the outer tunic of the eye. Its unified structure and function provide the eye with a clear refractive interface, tensile strength, and protection from external factors. The cornea is built from three different main layers of cells: the epithelium, the stroma, and the endothelium (Pepose, J. S. et al., "The cornea; Adler's Physiology of the eye: Clinical application", 9th ed. St. Louis: Mosby Year Book, 1992, 29-47; Spencer, W. H., "The cornea; Ophthalmic Pathology: an atlas and textbook", 4th ed., Philadelphia: W. B. Saunders Co., 1996, 157-65). In addition, the Descemet's membrane, the Bowman's layer, and the basement membrane are structures that are derived in some ways from one of these main cellular layers.

The corneal epithelium is the layer in direct contact with the external environment. It is a stratified squamous, non-keratinized structure with a thickness ranging from 40 to 100 μm, in rats and in humans, respectively. It is comprised of a superficial zone, usually formed by two to three layers of flat squamous cells; a middle zone, formed by two or three layers of polyhedral wing cells; and a basal zone consisting of a single row of columnar cells. The stratified corneal epithelium is characterized as a "tight" ion transporting functional syncitium which serves both as a protective barrier to the ocular surface, as well as an adjunct fluid secreting layer assisting the corneal endothelium in the regulation of stromal hydration, and thereby contributing to the maintenance of corneal transparency. The unique and specialized qualities offered by the corneal epithelium have been proven to be essential for the operation of the cornea as the principal refractive element of the eye. It is therefore important that its stratified structure be maintained irrespective of any environmental stresses.

Trauma to the surface of the cornea is highly prevalent; for example, minor scrapes, eye infections and diseases, chemical or mechanical accidents and surgical practice can all damage the cornea. One major complication in post corneal-trauma wound healing is the loss of visual acuity due to tissue reorganization. Patients at risk for ophthalmic healing problems include those who have undergone surgery. Examples of such surgery include, but are not limited to, cataract extraction, with or without lens replacement; corneal transplant or other penetrating procedures, such as penetrating keratoplasty (PKP); excimer laser photorefractive keratectomy; glaucoma filtration surgery; radial keratotomy; and other types of surgery to correct refraction or replace a lens.

The cornea provides the external optically smooth surface to transmit light into the eye. Surgery disrupts the forces which anchor the cornea in its normal configuration. In cataract patients, a full-thickness surgical incision is made in the region of the limbus. The cornea contracts when it heals, causing a local distortion of the tissue and a concomitant distortion in the visual field in the affected region (astigmatism).

Other surgical wounds in the cornea can initiate a wound healing process that causes a predetermined local shift in the curvature of the cornea. The most widely known of these techniques is radial keratotomy (RK), in which several partial-thickness incisions are produced to cause central corneal flattening. This technique, however, is limited due to a lack of predictable results and significant fluctuations in vision, both of which are related to the nature and extent of wound healing (Jester et al., Cornea (1992) 11: 191). For example, a reduction in peripheral bulging of the corneal tissue with an associated regression in the initial visual improvement has been observed in most RK patients (McDonnell and Schanzlin, *Arch. Ophthalmol.* (1988), 106: 212).

Wounds in the cornea also heal slowly, and incomplete healing tends to be associated with instability of visual acuity (with fluctuations in vision from morning to evening, as well as drifting visual acuity occurring over a period of weeks to months). This may be the cause of 34% or more of patients who have had radial keratotomy complaining of fluctuating vision one year after surgery (Waring et al., *Amer. J. Ophthalmol.* (1991) 111: 133). Also, if a corneal wound fails to heal completely, a wound "gape" can occur leading to a progressive hyperopic effect. Up to 30% of patients having the RK procedure are afflicted with hyperopic shifts associated with wound gape (Dietz et al., *Ophthalmology* (1986) 93: 1284).

Corneal regeneration after trauma is complex and not well understood. It involves the regeneration of three tissues: the epithelium, the stroma and the endothelium. Three main intercellular signaling pathways are thought to coordinate tissue regeneration: one mediated by growth factors (Baldwin, H. C. and Marshall, J., *Acta Ophthalmol. Scand.*, (2002) 80: 238-47), cytokines (Ahmadi, A. J. and Jakobiec, F. A., *Int. Ophthalmol. Clinics*, (2002) 42(3): 13-22) and chemokines (Kurpakus-Wheater, M, et al., *Biotech. Histochem*, (1999) 74: 146-59); another mediated by cell-matrix interactions (Tanaka, T., et al., *Jpn. J. Ophthalmol.,* (1999) 43: 348-54); and another mediated by the gap junctions and the connexin family of channel forming proteins.

Gap junctions are cell membrane structures, which facilitate direct cell-cell communication. A gap junction channel is formed of two connexins, each composed of six connexin subunits. Each hexameric connexin docks with a connexin in the opposing membrane to form a single gap junction. Gap junction channels can be found throughout the body. A tissue such as the corneal epithelium, for example, has six to eight cell layers, yet expresses different gap junction channels in different layers with connexin-43 in the basal layer and connexin-26 from the basal to middle wing cell layers. In general, connexins are a family of proteins, commonly named according to their molecular weight or classified on a phylogenetic basis into alpha, beta, and gamma subclasses. To date, 20 human and 19 murine isoforms have been identified (Willecke, K. et al., *Biol. Chem.*, (2002) 383, 725-37) perhaps indicating that each different connexin protein may be functionally specialized. Different tissues and cell types have characteristic patterns of connexin protein expression and tissues such as cornea have been shown to alter connexin protein expression pattern following injury or transplantation (Qui, C. et al., (2003) *Current Biology,* 13: 1967-1703; Brander et al., (2004), *J Invest Dermatol.* 122(5): 1310-20).

The corneal regeneration process post-trauma can result in the loss of corneal clarity and therefore influence the outcome of refractive surgery. Present treatments for damaged cornea generally include corneal transplant or attempts to use corneal cells/tissue for reconstruction. However, post-operative trauma to the corneal and the surrounding soft tissue following surgical procedures such as, for example, excimer laser photorefractive keratectomy, often results in scarring due to hypercellularity associated with modification of the extracellular matrix; including changes in epithelial cell patterning, myofibroblast differentiation, stromal remodeling, and epithelial hyperplasia at the site of a laser induced lesion.

In severe spinal cord injuries, the pathological changes that occur, whether by transection, contusion or compression, share some similarities with post-operative scar formation and tissue remodeling. Within 24-48 hours after injury, the damage spreads and significantly increases the size of the affected area. A gap junction-mediated bystander effect (Lin, J. H. et al., 1998*, Nature Neurosci.* 1: 431-432), by which gap junction channels spread neurotoxins and calcium waves from the damage site to otherwise healthy tissue may be involved. This is accompanied by the characteristic inflammatory swelling. The region of damage in the spinal cord is replaced by a cavity or connective tissue scar, both of which impede axonal regeneration (McDonald, J. W. et al, (September 1999) *Scientific American.* 55-63; Ramer, M. S. et al., *Spinal Cord.* (2000) 38: 449-472; Schmidt, C. E. and Baier Leach, J.; (2003) *Ann. Rev. Biomed. Eng.* 5: 293-347). Although progress has been made with some current therapeutic modalities, major constraints to spinal cord repair still remains, including the invasive intervention itself can further lesion spread and glial scar formation, impeding the repair process and risk further loss of neural function (Raisman, G. *J. Royal Soc. Med.* 96: 259-261).

Antisense technology has been used for the modulation of the expression for genes implicated in viral, fungal and metabolic diseases. U.S. Pat. No. 5,166,195, proposes oligonucleotide inhibitors of HIV. U.S. Pat. No. 5,004,810 proposes oligomers for hybridizing to herpes simplex virus Vmw65 mRNA and inhibiting replication. See also WO00/44409 to Becker et al., filed Jan. 27, 2000, and entitled "Formulations Comprising Antisense Nucleotides to Connexins", the contents of which are hereby incorporated by reference in their entirety, describes the use of antisense (AS) oligodeoxynucleotides to downregulate connexin expression to treat local neuronal damage in the brain, spinal cord or optic nerve, in the promotion of wound healing and reducing scar formation of skin tissue following surgery or burns. However, many difficulties remain that need to be overcome. It is often the case, for example, that the down regulation of a particular gene product in a non-target cell type can be deleterious. Additional problems that need to be overcome include the short half life of such ODN's (unmodified phosphodiester oligomers) typically have an intracellular half life of only 20 minutes owing to intracellular nuclease degradation (Wagner 1994, supra) and their delivery consistently and reliably to target tissues.

Therefore, there is a need and there are enormous potential advantages for the development of compounds for the problems described above. Such compounds, related compositions, and methods for their use are described and claimed herein.

BRIEF SUMMARY

The inventions described and claimed herein have many attributes and embodiments including, but not limited to, those set forth or described or referenced in this Summary. The inventions described and claimed herein are not limited to or by the features or embodiments identified in this Summary, which is included for purposes of illustration only and not restriction.

Provided herein are compounds useful for tissue engineering, including antisense compounds. Also provided are antisense compounds and methods for reducing tissue damage associated with ophthalmic procedures. The methods comprise, for example, administering an antisense compound to the eye of a subject in an amount sufficient to inhibit the expression of a connexin protein in the eye or in cells associated with the eye of the subject. While it is preferred that the expression of connexin protein is inhibited, it is envisioned that other proteins may be targets for modulation by the compounds, including the antisense compounds, either alone of in combination with antisense or other compounds that inhibit the expression of human connexins.

In certain embodiments, the ophthalmic procedure is an ophthalmic surgery, including but not limited to an excimer laser photorefractive keratectomy, a cataract extraction, corneal transplant, a surgery to correct refraction, a radial keratotomy, a glaucoma filtration surgery, a keratoplasty, an excimer laser photorefractive keratectomy, a corneal transplant, a surgery to correct refraction, a ocular surface neoplasm excision, a conjunctival or amniotic membrane graft, a pterygium and pingeculae excision, a ocular plastic surgery, a lid tumour excision, a reconstructive lid procedures for congentital abnormalities, an ectropian and entropian eyelid repair, a strabismus surgery (occular muscle), or any penetrating eye trauma.

Generally, at least a portion of the nucleotide sequence is known for connexins in which the inhibition of expression is desired. Preferably, an antisense compound is targeted to one or more specific connexin isotypes. Specific isotypes of connexins that may be targeted by the antisense compounds include, without limitation, 43, 37, 31.1, and 26. It is preferred, but not required, that the targeted connexins are human. A connexin (e.g., human) may, for example, have a nucleobase sequence selected from SEQ ID NO: 12-31.

In certain embodiments, antisense compounds are targeted to at least about 8 nucleobases of a nucleic acid molecule encoding a connexin having a nucleobase sequence selected from SEQ ID NO: 12-31.

In certain other embodiments, a second antisense compound is administered to the subject (e.g. the eye), wherein one or more other antisense compounds are targeted to at least about 8 nucleobases of a nucleic acid molecule encoding a connexin (e.g., human) having a nucleobase sequence selected from SEQ ID NO: 12-31. At least a second antisense compound may, for example, be targeted to a different connexin than a first antisense compound.

Examples of types of antisense compounds that may be used in various aspects of the invention include antisense oligonucleotides, antisense polynucleotides, deoxyribozymes, morpholino oligonucleotides, dsRNA, RNAi molecules, siRNA molecules, PNA molecules, DNAzymes, and 5'-end-mutated U1 small nuclear RNAs, analogs of the preceding; as well other compounds provided herein or known in the art; including but not limited to, for example, non-specific uncouplers such as octanol, glycerhetinic acids, and heptanol.

In certain embodiments, for example, the antisense compounds are antisense oligonucleotides that comprise naturally occurring nucleobases and an unmodified internucleoside linkage. In other embodiments, for example, the antisense compounds are antisense oligonucleotides comprising at least one modified internucleoside linkage, including those with a phosphorothioate linkage. Suitable antisense compounds also include, for example, oligonucleotides comprising at least one modified sugar moiety. Suitable antisense compounds also include, by way of example, oligonucleotides comprising at least one modified nucleobase.

In certain embodiments, antisense compounds provided herein are administered in combination with another compound, for example a compound useful for reducing tissue damage, reducing inflammation, promoting healing, or some other desired activity.

In another aspect, the invention includes methods of treating a subject (e.g., a patient) by administering antisense compounds to the subject.

In certain embodiments, antisense compounds provided herein are administered by local or topical administration. Antisense compounds provided herein can also be administered, for example, systemically or by intraocular injection.

Antisense compounds provided herein can be administered to a subject at a predetermined time, for example, relative to the formation of a wound, such as that occurs in an ophthalmic procedure (e.g., surgical). For example, antisense compounds can be administered before an ophthalmic procedure is performed, during an ophthalmic procedure, or after an ophthalmic procedure. Antisense compounds, for example, may be administered to a subject within minutes or hours before or after an ophthalmic procedure is performed. In certain embodiments, an antisense compound is administered after an ophthalmic procedure is performed, and for example the antisense compound is administered within about 4 hours of the procedure, within about 3 hours of the procedure, and more typically within about 2 hours of the ophthalmic procedure, or within about 1 hour of an ophthalmic procedure.

In another aspect, antisense compounds provided herein may be administered in a methods to effect tissue engineering. For example, antisense compounds provided herein may be administered in conjunction with a method that increases the thickness of cornea tissue in a subject. Such method may, or may not, be associated with an ophthalmic procedure (e.g., surgery). As an example, antisense compounds provided herein may be administered in conjunction with a method that promotes healing or prevents tissue damage in cells associated with the cornea of the subject (e.g., corneal cells).

In certain embodiments, for example, the antisense compound decreases scar formation. In certain embodiments, for example, the antisense compound reduces inflammation. In certain embodiments, for example, the antisense compound promotes wound healing.

In certain preferred embodiments, for example, the antisense compound is used in association with a surgical implantation procedure.

In certain embodiments, for example, the antisense compound is directed to connexin 43 and is administered to regulate epithelial basal cell division and growth.

In certain embodiments, for example, the antisense compound is directed to connexin 31.1 and is administered to regulate outer layer keratinisation.

According to certain embodiments, for example, the ophthalmic procedure is cataract extraction. In other embodiments, for example, the ophthalmic procedure is a corneal transplant. In other embodiments, for example, the ophthalmic surgical procedure is surgery to correct refraction. In another embodiments, for example, the ophthalmic procedure is radial keratotomy. In another embodiments, for example, the ophthalmic procedure is glaucoma filtration surgery. In still other embodiments, for example, the ophthalmic procedure is keratoplasty. In other embodiments, for example, the ophthalmic procedure is an ocular surface neoplasm excision. In other embodiments, for example, the ophthalmic procedure is a conjunctival or amniotic membrane graft. In other embodiments, for example, the ophthalmic procedure is a pterygium and pingeculae excision. In other embodiments, for example, the ophthalmic procedure is an ocular plastic surgery. In other embodiments, for example, the ophthalmic procedure is a lid tumour excision. In other embodiments, for example, the ophthalmic procedure is a reconstructive lid procedure for congentital abnormalities. In other embodiments, for example, the ophthalmic procedure is an ectropian and entropian eyelid repair. In other embodiments, for example, the ophthalmic procedure is a strabismus surgery (occular muscle). In other embodiments, for example, the ophthalmic procedure is a penetrating eye trauma.

In certain further embodiments, for example, compounds and compositions are used to promote healing or to prevent tissue damage in cells associated with cornea, where the cells associated with the cornea may be any cell in the eye, including but not limited to corneal cells.

The agents provided herein, including antisense compounds, may increase the thickness of cornea tissue in a subject. In certain embodiments, for example, the antisense compound is used in combination with another compound useful for reducing tissue damage or promoting healing. For example, the antisense compounds may be coadministered with a growth factor, cytokine, or the like.

In another aspect, for example, a pharmaceutical composition for reducing tissue damage associated with ophthalmic surgery is provided. The pharmaceutical composition is suitably formulated, for example, for topical or local administration to the eye of a subject comprising an antisense compound present in an amount sufficient to inhibit the expression of a human connexin protein in cells associated with the eye of the subject. The antisense compound, for example, is preferably targeted to at least about 8 nucleobases of a nucleic acid molecule encoding a connexin (e.g., human) having a nucleobase sequence selected from SEQ ID NO:12-31.

In certain embodiments, for example, the antisense compounds are in the form of a pharmaceutical composition comprising a pharmaceutically acceptable carrier or vehicle and the agent or antisense compound is present in an amount effective to promote wound healing in a subject. In certain embodiments, the pharmaceutical compositions may be, for example, in a form suitable for topical administration, including in a form suitable for topical or local administration to the eye of a subject. In certain further embodiments, for example, the compositions and formulations may be in the form of a gel, a cream, or any of the forms described herein or known in the art, whether currently or in the future.

In another aspect, the invention includes pharmaceutical compositions comprising antisense compounds. In one embodiment, for example, a pharmaceutical composition is provided for reducing tissue damage associated with an ophthalmic procedure (e.g., surgery), such that the pharmaceutical composition is formulated for topical or local administration to the eye of a subject and it comprises an antisense compound present in an amount sufficient to inhibit the expression of a human connexin protein in cells associated with the eye of the subject. In certain embodiments, for example, the antisense compound is targeted to at least about 8 nucleobases of a nucleic acid molecule encoding a connexin (e.g., human) having a nucleobase sequence selected from SEQ ID NO: 12-31.

In certain embodiments, for example, the pharmaceutical composition includes a pharmaceutically acceptable carrier comprising a buffered pluronic acid or gel. This includes in one embodiment, for example, up to about 30% pluronic acid in phosphate buffered saline.

In another aspect, methods of designing antisense oligonucleotides that are targeted to one or more connexin are provided. The method may include the optimization of selected parameters, such as the thermo stability, affinity, and specificity of a particular oligonucleotide with a selected target. This method may be used to selected and develop antisense oligonucleotides comprising one or more particular desired polynucleotide sequence. Testing of the antisense oligonucleotides may be performed in conjunction with the method, for example, for their ability to cleave mRNA or block the translation of a connexin protein.

BRIEF DESCRIPTION OF THE DRAWINGS

FIGS. 4A, 4B, and 4C are controls; and 4D, 4E, and 4F are antisense treated corneas.

FIG. 5F—central) and it was very uneven (5E). In contrast antisense ODN treated corneas had a continuous and relatively even basal lamina at the wound edge (5G) and centrally (5H).

FIG. 4A shows the normal connexin-43 protein expression (light, gray-scale) in the basal cells and connexin-26 protein expression (dark, gray-scale) in the basal to intermediate cells of a Pluronic gel control treated corneal epithelium. As14 (14B), as769 (14D), as892 (14F), all three showing no deoxyribozyme cleavage in vitro) and DB1 sense control (14H) oligomers did not affect the expression of both connexins in ex vivo cultures. as605 (14C), as783 (14E) and DB1 (14G) (all three showing positive in vitro deoxyribozyme cleavage) showed only specific connexin-43 knock down in the epithelium of treated corneas.

DETAILED DESCRIPTION

Figure 1:
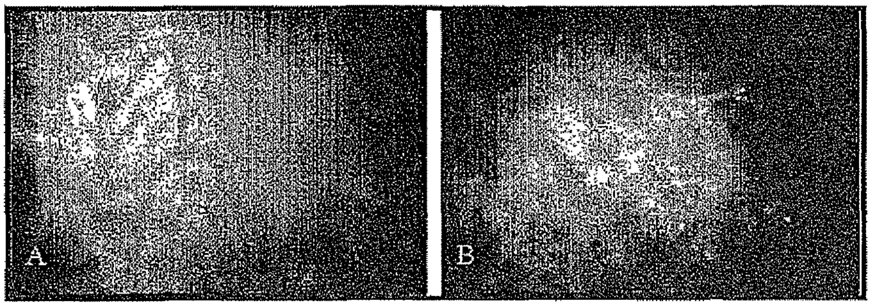
FIG. 1 shows in vivo confocal microscopic images of corneas 12 hours post photorefractive keratectomy in control and antisense oligonucleotides treated eyes.

The practice of the present inventions may employ various conventional techniques of molecular biology (including recombinant techniques), microbiology, cell biology, biochemistry, nucleic acid chemistry, and immunology, which are within the skill of the art. Such techniques are explained fully in the literature, and include but are not limited to, by way of example only, Molecular Cloning: A Laboratory Manual, second edition (Sambrook et al., 1989) and Molecular Cloning: A Laboratory Manual, third edition (Sambrook and Russel, 2001), jointly and individually referred to herein as "Sambrook"; Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. (jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993).

Definitions

Before further describing the inventions in general and in terms of various nonlimiting specific embodiments, certain terms used in the context of the describing the invention are set forth. Unless indicated otherwise, the following terms have the following meanings when used herein and in the appended claims. Those terms that are not defined below or elsewhere in the specification shall have their art-recognized meaning.

"Antisense compounds" include different types of molecule that act to inhibit gene expression, translation, or function, including those that act by sequence-specific targeting of mRNAs for therapeutic applications.

Antisense compounds thus include, for example, the major nucleic-acid based gene-silencing molecules such as, for example, chemically modified antisense oligodeoxyribonucleic acids (ODNs), ribozymes and siRNAs (Scherer, L. J. and Rossi, J. J. *Nature Biotechnol.* 21: 1457-1465 (2003). Antisense compounds may also include antisense molecules such as, for example, peptide nucleic acids (PNAs) (Braasch, D. A. and Corey, D. R., *Biochemistry* 41, 4503-4510 (2002)), morpholino phosphorodiamidates (Heasman, J., *Dev. Biol.,* 243, 209-214 (2002), DNAzymes (Schubert, S. et al., *Nucleic Acids Res.* 31, 5982-5992 (2003). Chakraborti, S. and Banerjea, A. C., *Mol. Ther.* 7, 817-826 (2003), Santoro, S. W. and Joyce, G. F. *Proc. Natl Acad. Sci. USA* 94, 4262-4266 (1997), and the recently developed 5'-end-mutated U1 small nuclear RNAs (Fortes, P. et al., *Proc. Natl. Acad. Sci. USA* 100, 8264-8269 (2003)).

The term "antisense sequences" refers to polynucleotides having antisense compound activity and include, but are not limited to, sequences complementary or partially complementary, for example, to an RNA sequence. Antisense sequences thus include, for example, include nucleic acid sequences that bind to mRNA or portions thereof to block transcription of mRNA by ribosomes. Antisense methods are generally well known in the art. See, for example, PCT publication WO94/12633, and Nielsen et al., 1991, *Science* 254:1497; Oligonucleotides and Analogues, A Practical Approach, edited by F. Eckstein, IRL Press at Oxford University Press (1991); Antisense Research and Applications (1993, CRC Press.

As used herein, "messenger RNA" includes not only the sequence information to encode a protein using the three letter genetic code, but also associated ribonucleotide sequences which form the 5'-untranslated region, the 3'-untranslated region, and the 5' cap region, as well as ribonucleotide sequences that form various secondary structures. Oligonucleotides may be formulated in accordance with this invention which are targeted wholly or in part to any of these sequences.

In general, nucleic acids (including oligonucleotides) may be described as "DNA-like" (i.e., having 2'-deoxy sugars and, generally, T rather than U bases) or "RNA-like" (i.e., having 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like".

The term "complementary" generally refers to the natural binding of polynucleotides under permissive salt and temperature conditions by base pairing. For example, the sequence "A-G-T" binds to the complementary sequence "T-C-A". Complementarity between two single-stranded molecules may be "partial", such that only some of the nucleic acids bind, or it may be "complete", such that total complementarity exists between the single stranded molecules. The degree of complementarity between nucleic acid molecules has significant effects on the efficiency and strength of the hybridization between them. "Hybridizable" and "complementary" are terms that are used to indicate a sufficient degree of complementarity such that stable and binding occurs between the DNA or RNA target and the oligonucleotide. It is understood that an oligonucleotide need not be 100% complementary to its target nucleic acid sequence to be hybridizable, and it is also understood that the binding may be target-specific, or may bind to other non-target molecules so long as the non-specific binding does not significantly or undesirably thwart the therapeutic or other objective. An oligonucleotide is used to interfere with the normal function of the target molecule to cause a loss or diminution of activity, and it is preferred that there is a sufficient degree of complementarity to avoid non-specific or unwanted binding of the oligonucleotide to non-target sequences under conditions in which specific binding is desired, i.e., under physiological conditions in the case of in vivo assays or therapeutic treatment or, in the case of in vitro assays, under conditions in which the assays are conducted. In the context of certain embodiments of the invention, absolute complementarity is not required. Polynucleotides that have sufficient complementarity to form a duplex having a melting temperature of greater than 20° C., 30° C., or 40° C. under physiological conditions, are generally preferred.

A "disorder" is any condition that would benefit from treatment with a molecule or composition of the invention, including those described or claimed herein. This includes chronic and acute disorders or diseases including those pathological conditions that predispose the mammal to the disorder in question.

"Targeting" an oligonucleotide to a chosen nucleic acid target can be a multistep process. The process may begin with identifying a nucleic acid sequence whose function is to be modulated. This may be, for example, a cellular gene (or mRNA made from the gene) whose expression is associated with a particular disease state, or a foreign nucleic acid (RNA or DNA) from an infectious agent. The targeting process may also include determination of a site or sites within the nucleic acid sequence for the oligonucleotide interaction to occur such that the desired effect, i.e., inhibition of protein expression, reduced protein detection, or other modulation of activity, will result. Once a target site or sites have been identified, antisense compounds (e.g., oligonucleotides) are chosen which are sufficiently or desirably complementary to the target, i.e., hybridize sufficiently and with an adequate or otherwise desired specificity, to give the desired modulation. In the present invention, targets include nucleic acid molecules encoding one or more connexins. The targeting process may also include determination of a site or sites for the antisense interaction to occur such that the desired effect, will result. A preferred intragenic site, for example, is the region encompassing the translation initiation or termination codon of the open reading frame (ORF) of the gene. The translation initiation codon is typically 5'-AUG (in transcribed mRNA molecules; 5'-ATG in the corresponding DNA molecule), tand may also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions.

The term "oligonucleotide" includes an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide (ODN). Nuclease resistance is routinely measured by incubating oligonucleotides with cellular extracts or isolated nuclease solutions and measuring the extent of intact oligonucleotide remaining over time, usually by gel electrophoresis. Oligonucleotides, which have been modified to enhance their nuclease resistance, can survive intact for a longer time than unmodified oligonucleotides. A number of modifications have also been shown to increase binding (affinity) of the oligonucleotide to its target. Affinity of an oligonucleotide for its target is routinely determined by measuring the Tm (melting temperature) of an oligonucleotide/target pair, which is the temperature at which the oligonucleotide and target dissociate. Dissociation is detected spectrophotometrically. The greater the Tm, the greater the affinity of the oligonucleotide has for the target. In some cases, oligonucleotide modifications which enhance target-binding affinity are also able to enhance nuclease resistance.

A "polynucleotide" means a plurality of nucleotides. Thus, the terms "nucleotide sequence" or "nucleic acid" or "polynucleotide" or "oligonucleotide" or "oligodeoxynucleotide" all refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material.

A polynucleotide that encodes a connexin, a connexin fragment, or a connexin variant includes a polynucleotide encoding: the mature form of the connexin found in nature; the mature form of the connexin found in nature and additional coding sequence, for example, a leader or signal sequence or a proprotein sequence; either of the foregoing and non-coding sequences (for example, introns or non-coding sequence 5' and/or 3' of the coding sequence for the mature form of the polypeptide found in nature); fragments of the mature form of the connexin found in nature; and variants of the mature form of the connexin found in nature. Thus, "connexin-encoding polynucleotide" and the like encompass polynucleotides that include only a coding sequence for a desired connexin, fragment, or variant, as well as a polynucleotide that includes additional coding and/or non-coding sequences.

The terms "peptidomimetic" and "mimetic" refer to a synthetic chemical compound that may have substantially the same structural and functional characteristics of the antisense polypeptides provided herein and that mimic the connexin-specific inhibitory activity, at least in part and to some degree. Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15: 29 (1986); Veber and Freidinger; *TINS;* 392 (1985); and Evans et al., *J. Med. Chem.* 30: 1229 (1987); Beeley N., *Trends Biotechnol.* 1994 June; 12(6): 213-6; Kieber-Emmons T, et al.; *Curr Opin Biotechnol.* 1997 August; 8(4): 435-41. Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a antisense polynucleotide, but have one or more peptide linkages optionally replaced by a linkage selected from the group consisting of, for example, —CH2NH—, —CH2S—, —CH2-CH2-, —CH═CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of down-regulating biological activities of connexin proteins, such as, for example, gap-junction-mediated-cell-cell communication.

The term "composition" is intended to encompass a product comprising one or more ingredients.

The terms "modulator" and "modulation" of connexin activity, as used herein in its various forms, is intended to encompass inhibition in whole or in part of the expression or activity of a connexin. Such modulators include small molecules agonists and antagonists of connexin function or expression, antisense molecules, ribozymes, triplex molecules, and RNAi polynucleotides, gene therapy methods, and others.

The phrase "percent (%) identity" refers to the percentage of sequence similarity found in a comparison of two or more sequences. Percent identity can be determined electronically using any suitable software. Likewise, "similarity" between two sequences (or one or more portions of either or both of them) is determined by comparing the sequence of one sequence to the a second sequence.

By "pharmaceutically acceptable" it is meant, for example, a carrier, diluent or excipient that is compatible with the other ingredients of the formulation and suitable for administration to a recipient thereof.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As will be appreciated, a "fragment" of a protein may be a form of the protein truncated at the amino terminus, the carboxy terminus, and/or internally (such as by natural splicing), and may also be variant and/or derivative. A "domain" of a protein is also a fragment, and comprises the amino acid residues of the protein required to confer biochemical activity corresponding to naturally occurring protein. Truncated molecules that are linear biological polymers such as nucleic acid molecules or polypeptides may have one or more of a deletion from either terminus of the molecule and/or one or more deletions from a non-terminal region of the molecule, where such deletions may be deletions of from about 1-1500 contiguous nucleotide or amino acid residues, preferably about 1-500 contiguous nucleotide or amino acid residues and more preferably about 1-300 contiguous nucleotide or amino acid residues, including deletions of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues.

The term "stringent conditions" refers to conditions that permit hybridization between polynucleotides. Stringent conditions can be defined by salt concentration, the concentration of organic solvent (for example, formamide), temperature, and other conditions well known in the art. Stringency can be increased by reducing the concentration of salt, increasing the concentration of organic solvents, (for example, formamide), or raising the hybridization temperature. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, for example, formamide, while high stringency hybridization can be obtained in the presence of an organic solvent (for example, at least about 35% formamide, most preferably at least about 50% formamide). Stringent temperature conditions will ordinarily include temperatures of at least about 30° C., more preferably of at least about 37° C., and most preferably of at least about 42° C. Varying additional parameters, for example, hybridization time, the concentration of detergent, for example, sodium dodecyl sulfate (SDS), and the inclusion or exclusion of carrier DNA, are well known to those skilled in the art. Various levels of stringency are accomplished by combining these various conditions as needed, and are within the skill in the art. Stringent hybridization conditions may also be defined by conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, for example, Berger and Kimmel, 1987, Methods In Enzymology, Vol. 152*: Guide To Molecular Cloning Techniques*, San Diego: Academic Press, Inc. and Sambrook et al., (1989) Molecular Cloning: A Laboratory Manual, 2nd Ed., Vols. 1-3, Cold Spring Harbor Laboratory). As indicated by standard references, a simple estimate of the Tm value may be calculated by the equation: Tm=81.5+0.41(% G+C), when a nucleic acid is in aqueous solution at 1 M NaCl (see for example, Anderson and Young, "Quantitative Filter Hybridization" in Nucleic Acid Hybridization (1985)). The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (for example for example, the presence or absence of formamide, dextran sulfate, polyethylene glycol). The effects of these factors are well known and are discussed in standard references in the art, see for example, Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (for example, 10 to 50 nucleotides) and at least about 60° C. for long probes (for example, greater than 50 nucleotides). As noted, stringent conditions may also be achieved with the addition of destabilizing agents such as formamide, in which case lower temperatures may be employed. In the present invention, the polynucleotide may be a polynucleotide which hybridizes to the connexin mRNA under conditions of medium to high stringency such as 0.03M sodium chloride and 0.03M sodium citrate at from about 50 to about 60 degrees centigrade.

The term "therapeutically effective amount" means the amount of the subject compound that will elicit a desired response, for example, a biological or medical response of a tissue, system, animal or human that is sought, for example, by a researcher, veterinarian, medical doctor, or other clinician.

"Treatment" refers to both therapeutic treatment and prophylactic or preventive measures. Those in need of treatment include those already with the disorder as well as those in which the disorder is to be prevented.

The term "vector" refers to a nucleic acid molecule amplification, replication, and/or expression vehicle in the form of a plasmid, phage, viral, or other system (be it naturally occurring or synthetic) for the delivery of nucleic acids to cells where the plasmid, phage, or virus may be functional with bacterial, yeast, invertebrate, and/or mammalian host cells. The vector may remain independent of host cell genomic DNA or may integrate in whole or in part with the genomic DNA. The vector will generally but need not contain all necessary elements so as to be functional in any host cell it is compatible with. An "expression vector" is a vector capable of directing the expression of an exogenous polynucleotide, for example, a polynucleotide encoding a binding domain fusion protein, under appropriate conditions.

As described herein, the terms "homology and homologues" include polynucleotides that may be a homologue of sequence in connexin polynucleotide (e.g. mRNA). Such polynucleotides typically have at least about 70% homology, preferably at least about 80%, 90%, 95%, 97% or 99% homology with the relevant sequence, for example over a region of at least about 15, 20, 30, 40, 50, 100 more contiguous nucleotides (of the homologous sequence).

Homology may be calculated based on any method in the art. For example the UWGCG Package provides the BEST- FIT program which can be used to calculate homology (for example used on its default settings) (Devereux et al. (1984) Nucleic Acids Research 12, p 387-395). The PILEUP and BLAST algorithms can be used to calculate homology or line up sequences (typically on their default settings), for example as described in Altschul S. F. (1993); *J Mol Evol* 36: 290-300; Altschul, S. F. et al.; (1990); *J Mol Biol* 215: 403-10. Software for performing BLAST analyses is publicly available through the National Center for Biotechnology Information (http://www.ncbi.nlm.nih.gov/L). This algorithm involves first identifying high scoring sequence pair by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence is less than about 1, preferably less than about 0.1, more preferably less than about 0.01, and most preferably less than about 0.001.

The homologous sequence typically differs from the relevant sequence by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example 0.03M sodium chloride and 0.03M sodium citrate at from about 50 degrees C. to about 60 degrees C.). However, such hybridization may be carried out under any suitable conditions known in the art (see Sambrook et al. (1989), Molecular Cloning: A Laboratory Manual). For example, if high stringency is required, suitable conditions include 0.2×SSC at 60 degrees C. If lower stringency is required, suitable conditions include 2×SSC at 60 degrees C.

A "cell" means any living cell suitable for the desired application. Cells include eukaryotic and prokaryotic cells.

The term "gene product" refers to an RNA molecule transcribed from a gene, or a polypeptide encoded by the gene or translated from the RNA.

The term "recombinant" refers to a polynucleotide synthesized or otherwise manipulated in vitro (for example, "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process refers to use of recombinant nucleic acid techniques, for example, involving human intervention in the nucleotide sequence, typically selection or production. Alternatively, it can be a polynucleotide made by generating a sequence comprising a fusion of two or more fragments that are not naturally contiguous to each other. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

A "recombinant host cell" is a cell that contains a vector, for example, a cloning vector or an expression vector, or a cell that has otherwise been manipulated by recombinant techniques to express a protein of interest.

This invention includes methods of using compounds and compositions for site-specific modulation of gap-junction-associated protein expression for wound-healing, for example, well as, for example, surgically related wound-healing and/or tissue remodeling applications. The invention is useful, for example, for correcting visual defects in conjunction with laser surgery, for in vitro corneal engineering, and for direct eye treatments where remodeling of the cornea is desired, including those preformed independent of or alternatively, in conjunction with, a procedure (e.g., surgery) performed on the eye. Antisense modulation of direct cell-cell communication is preferably mediated by molecules that directly or indirectly reduce coupling between cells in tissues. Such molecules include polynucleotides such as antisense deoxynucleotides, morpholino nucleotides, RNAi and deoxribozymes targeted to specific connexin isoforms which result in reduced translation of the protein isoform and interfere with the function of cell gap junctions. Administration of these antisense compounds results in the reduction of gap-junction-mediated cell-cell communication at the site at which connexin expression is downregulated.

Connexins play important roles in gap junction-mediated cell-cell signaling. Overexpression of connexin is associated with post surgical scarring and post-trauma-induced tissue remodeling. According to certain embodiments of the invention, connexins represent useful targets for treatment of adverse effects associated with corneal trauma and post-surgical tissue remodeling; and for diseases and disorders where localized disruption in direct cell-cell communication is desirable. Particularly, modulation of the expression of connexins can be useful for the site-specific modulation of gap-junction-associated protein expression for tissue remodeling/tissue engineering applications. Antisense compounds provided herein may be used for the modulation of connexins in association with ophthalmic procedures or surgeries such as, for example, cataract surgery, intraocular lens surgery, corneal transplant surgery and some types of glaucoma surgery, and other procedures described herein.

In certain embodiments, the modulation of the connexins can be applied in ophthalmic disorders affecting the posterior segment, including the retina and lens. In another aspect of this invention, the modulation of the connexins can be applied in ophthalmic disorders affecting the anterior segment, which includes the cornea, conjunctiva and sclera. In the context of this invention, posterior segment disorders include macular holes and degeneration, retinal tears, diabetic retinopathy, vitreoretinopathy and miscellaneous disorders. Also in the context of this invention, a disorder of the lens may include cataracts. In yet another aspect, it is contemplated that the disorders of the cornea are refractive disorders such as the sequalae of radial keratotomy, dry eye, viral conjunctivitis, ulcerative conjunctivitis and scar formation in wound healing, such as, for example, corneal epithelial wounds, and the consequences of Sjogren's syndrome.

The present invention discloses antisense compounds, particularly oligonucleotides, for use in modulating the function of nucleic acid molecules encoding connexins, ultimately modulating the amount of connexins produced. This is accomplished by providing oligonucleotides which specifically hybridize with nucleic acids, preferably mRNA, encoding connexins.

This relationship between an antisense compound such as an oligonucleotide and its complementary nucleic acid target, to which it hybridizes, is commonly referred to as "antisense". As described herein, "targeting" of an oligonucleotide to a chosen nucleic acid target is typically a multistep process. The process usually begins with identifying a nucleic acid sequence whose function is to be modulated. This may be, as an example, a cellular gene (or mRNA made from the gene) whose expression is associated with a particular disease state. In the present invention, the targets are nucleic acids encoding connexins; in other words, a gene encoding connexin, or mRNA expressed from the connexin gene. mRNA which encodes connexin is presently a preferred target. The targeting process also includes determination of a site or sites within the nucleic acid sequence for the antisense interaction to occur such that modulation of gene expression will result.

In the context of the invention, messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with the present invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding connexin, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

In the context of this invention, an antisense polynucleotide may, for example, hybridize to all or part of a connexin mRNA. Typically the antisense polynucleotide hybridizes to the ribosome binding region or the coding region of the connexin mRNA. The polynucleotide may be complementary to all of or a region of a connexin mRNA. For example, the polynucleotide may be the exact complement of all or a part of connexin mRNA. The antisense polynucleotide may inhibit transcription and/or translation of the connexin. Preferably the polynucleotide is a specific inhibitor of transcription and/or translation of the connexin gene, and does not inhibit transcription and/or translation of other genes. The product may bind to the connexin gene or mRNA either (i) 5' to the coding sequence, and/or (ii) to the coding sequence, and/or (iii) 3' to the coding sequence. Generally the antisense polynucleotide will cause the expression of connexin mRNA and/or protein in a cell to be reduced. The antisense polynucleotide is generally antisense to the connexin mRNA. Such a polynucleotide may be capable of hybridizing to the connexin mRNA and may inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of connexin. In the context of this invention "modulation" includes either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

Once the target site or sites have been identified, oligonucleotides are chosen which are sufficiently complementary to the target, i.e., hybridize sufficiently well and with sufficient specificity, to give the desired modulation. The antisense nucleic acids (DNA, RNA, modified, analogues, and the like) can be made using any suitable method for producing a nucleic acid. Oligodeoxynucleotides directed to other connexin proteins can be selected in terms of their nucleotide sequence by any art recognized approach, such as, for example, the computer programs MacVector and OligoTech (from Oligos etc. Eugene, Oreg., USA). Equipment for such synthesis is available through several vendors including MacVector and OligoTech (from Oligos etc. Eugene, Oreg., USA). For general methods relating to antisense polynucleotides, see Antisense RNA and DNA, D. A. Melton, Ed., Cold Spring Harbor Laboratory, Cold Spring Harbor, N.Y. (1988)). See also, Dagle et al., *Nucleic Acids Research,* 19: 1805 (1991). For antisense therapy, see, for example, Uhlmann et al., *Chem. Reviews,* 90: 543-584 (1990). Typically, at least a portion of the nucleotide sequence is known for connexins in which the inhibition of expression is desired. Preferably, an antisense compound is targeted to one or more specific connexin isotypes. Specific isotypes of connexins that may be targeted by the antisense compounds include, without limitation, 43, 37, 31.1, 26, and others described herein. It is preferred, but not required, that the targeted connexins are human. A connexin may, for example, have a nucleobase sequence selected from SEQ ID NO:12-31. In certain embodiments, antisense compounds are targeted to at least 8 nucleobases of a nucleic acid molecule encoding a connexin having a nucleobase sequence selected from SEQ ID NO:12-31.

In certain other embodiments, a second antisense compound is administered to the eye of the subject, wherein the second antisense compound is targeted to at least about 8 nucleobases of a nucleic acid molecule encoding a connexin having a nucleobase sequence selected from SEQ ID NO:12-31, wherein said second antisense compound is targeted to a different connexin than a first antisense compound.

Connexin targets will vary depending upon the type of tissue to be engineered or remodeled and the precise sequence of the antisense polynucleotide used in the invention will depend upon the target connexin protein. The connexin protein or proteins targeted by the oligonucleotides will be dependent upon the site at which downregulation is to be directed. This reflects the nonuniform make-up of gap junction (s) at different sites throughout the body in terms of connexin sub-unit composition. Some connexin proteins are however more ubiquitous than others in terms of distribution in tissue. As described herein, cornea-associated connexins such as connexin 43 are preferred in some embodiments. Therefore, in the context of the invention, oligonucleotides either alone or in combination, targeted towards connexin 43, 26, 37, 30 and/or 31.1 (e.g. see SEQ. ID. NOS: 1-11) which are suitable for corneal engineering or remodeling application. In one aspect of the invention, the oligodeoxynucleotides may be unmodified phosphodiester oligomers. In another aspect of the invention, the polynucleotides may be single or double stranded.

It is also contemplated that oligonucleotides targeted at separate connexin proteins may be used in combination (for example one, two, three, four or more different connexins may be targeted). For example, ODNs targeted to connexin 43, and one or more other members of the connexin family (such as connexin 26, 30, 31.1, 37 and 43) can be used in combination. It is also contemplated that individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences. Thus, in certain embodiments, antisense compounds are targeted to at least 8 nucleobases of a nucleic acid molecule encoding human connexin 26, connexin 30, connexin 31.1, human connexin 37, connexin 43, wherein said antisense compound inhibits the expression of a human connexin protein in cells associated with the eye of said patient.

In certain embodiments, the nucleic acid molecules encoding a connexin have a nucleobase sequence selected from SEQ. ID NO:12-31. In certain embodiments, the compositions target two or more human connexin proteins and inhibit the expression of two or more human connexin proteins. In further certain embodiments, the antisense compounds are antisense oligonucleotides. Exemplary antisense oligonucleotide to connexin 43 selected include GTA ATT GCG GCA AGA AGA ATT GTT TCT GTC (SEQ ID NO: 1); GTA ATT GCG GCA GGA GGA ATT GTT TCT GTC (SEQ ID NO: 2); and GGC AAG AGA CAC CAA AGA CAC TAC CAG CAT (SEQ ID NO: 3). An example of an antisense oligonucleotide to connexin 26 has the sequence TCC TGA GCA ATA CCT AAC GAA CAA ATA (SEQ ID NO: 4). Exemplary antisense oligonucleotide to connexin 37 selected include 5' CAT CTC CTT GGT GCT CAA CC 3' (SEQ ID NO: 5) and 5' CTG AAG TCG ACT TGG CTT GG 3' (SEQ ID NO: 6). Exemplary antisense oligonucleotide to connexin 30 selected include 5' CTC AGA TAG TGG CCA GAA TGC 3' (SEQ ID NO: 7) and 5' TTG TCC AGG TGA CTC CAA GG 3' (SEQ ID NO: 8). Exemplary antisense oligonucleotide to connexin 31.1 selected include 5' CGT CCG AGC CCA GAA AGA TGA GGT C 3'(SEQ ID NO: 9); 5' AGA GGC GCA CGT GAG ACA C 3' (SEQ ID NO: 10); and 5' TGA AGA CAA TGA AGA TGT T 3'(SEQ ID NO: 11).

In a further embodiment, oligodeoxynucleotides selected from the following sequences are particularly suitable for down-regulating connexin43 expression:

```
                                        (SEQ ID NO: 1)
5' GTA ATT GCG GCA AGA AGA ATT GTT TCT GTC 3'

                                        (SEQ ID NO: 2)
5' GTA ATT GCG GCA GGA GGA ATT GTT TCT GTC 3';
and

                                        (SEQ ID NO: 3)
5' GGC AAG AGA CAC CAA AGA CAC TAC CAG CAT 3'
```

In yet another embodiment, oligodeoxynucleotides selected from the group following sequences are particularly suitable for connexins 26, 37, 30, and 31.1:

```
(connexin26)
                                      (SEQ ID NO: 4)
5' TCC TGA GCA ATA CCT AAC GAA CAA ATA 3'

(connexin37)
                                      (SEQ ID NO: 5)
5' CAT CTC CTT GGT GCT CAA CC 3'

(connexin37)
                                      (SEQ ID NO: 6)
5' CTG AAG TCG ACT TGG CTT GG 3'

(connexin30)
                                      (SEQ ID NO: 7)
5' CTC AGA TAG TGG CCA GAA TGC 3'

(connexin30)
                                      (SEQ ID NO: 8)
5' TTG TCC AGG TGA CTC CAA GG 3'

(connexin31.1)
                                      (SEQ ID NO: 9)
5' CGT CCG AGC CCA GAA AGA TGA GGT C 3'

(connexin31.1)
                                     (SEQ ID NO: 10)
5' AGA GGC GCA CGT GAG ACA C 3'

(connexin31.1)
                                     (SEQ ID NO: 11)
5' TGA AGA CAA TGA AGA TGT T 3'
```

The antisense compounds provided herein generally comprise from about 8 to about 40 nucleobases (i.e. from about 8 to about 40 linked nucleosides), and more typically those comprising from about 12 to about 40 nucleobases, and even more typically about 30 nucleobases. Antisense compounds comprising polynucleotides may be at least about 40, for example at least about 60 or at least about 80, nucleotides in length and up to 100, 200, 300, 400, 500, 1000, 2000 or 3000 or more nucleotides in length. Suitable antisense compounds include, for example, a 30 mer ODN.

In certain embodiments, antisense compounds are targeted to at least about 8 nucleobases of a nucleic acid molecule encoding a connexin having a nucleobase sequence selected from SEQ ID NO:12-31. In other embodiments, the antisense compound is targeted to at least about 10, at least about 12, at least about 14, at least about 16, at least about 18, at least about 20, at least about 25, at least about 30, and at least about 35 nucleobases of a nucleic acid molecule encoding a connexin having a nucleobase sequence selected from SEQ ID NO:12-31. The size of the antisense compounds, including oligonucleotides targeted to between at least about 8 and 35 nucleobases of a nucleic acid molecule encoding a human connexin, may be 8 nucleobases in length or longer, between 8 and 100 nucleobases, between eight and 50 nucleobases, between eight and 40 nucleobases, between 10 and 50 nucleobases, between 12 and 50 nucleobases, between 14 and 50 nucleobases, between 16 and 50 nucleobases, between 18 and 50 nucleobases, between 20 and 50 nucleobases, between 25 and 50 nucleobases, between 15 and 35 nucleobases in length, and the like. Other antisense compounds of the invention may be or smaller or larger is size, for example having more than 100 nucleobases in length.

Antisense compounds include antisense oligonucleotides (ODN), antisense polynucleotides, deoxyribozymes, morpholino oligonucleotides, RNAi molecules or analogs thereof, siRNA molecules or analogs thereof, PNA molecules or analogs thereof, DNAzymes or analogs thereof, 5'-end-mutated U1 small nuclear RNAs and analogs thereof.

As provided herein, the antisense compound may include the use of oligodeoxynucleotides (ODNs). ODNs are generally about 20 nucleotides in length and act by hybridizing to pre-mRNA and mRNA to produce a substrate for ribonuclease H (RNase H), which specifically degrades the RNA strand of the formed RNA-DNA duplexes. If modified in a way to prevent the action of RNase H, ODNs can inhibit translation of mRNA via steric hindrance, or inhibit splicing of pre-mRNAs. ODNs and modifications thereof have been used to target dsDNA for the inhibition of transcription by the formation of triple helices. ODN may be obtained by art recognized methods of automated synthesis and it is relatively straightforward to obtain ODNs of any sequence and to block gene expression via antisense base pairing.

In certain aspects, the phosphodiester backbone of ODNs can be modified to increase their efficacy as target-specific agents for blocking gene expression. These backbone modifications were developed to improve the stability of the ODNs and to enhance their cellular uptake. The most widely used modification is one in which the nonbridging oxygen is replaced by a sulfur atom, creating phosphorothioate ODNs. At least one phosphorothioate ODN has been approved by the FDA, and several other phosphorothioate antisense ODNs are in earlier stages of clinical trials for a variety of cancers and inflammatory diseases.

The mechanisms of action of ODNs with respect to blocking gene function vary depending upon the backbone of the ODN (Branch, A. D. Hepatology 24, 1517-1529 (1996); Dias, N. and Stein, C. A. Mol. Cancer Thor. 1, 347-355 (2002); Stein, C. A. and Cohen, J. S., Cancer Res. 48, 2659-2668 (1988); Zon, G. Ann. N.Y. Acad Sci., 616, 161-172 (1990). Net negatively charged ODNs, such as phosphodiesters and phorphorothioates, elicit RNAse H-mediated cleavage of the target mRNA. Other backbone modifications that do not recruit RNAse H, because of their lack of charge or the type of helix formed with the target RNA, can be classified as steric hindrance ODNs. Popularly used members of this latter group include morpholinos, U—O-methyls, 2"-O-allyls, locked nucleic acids and peptide nucleic acids (PNAs). These ODNs can block splicing, translation, nuclear-cytoplasmic transport and translation, among other inhibition targets.

In another aspect, modulation of the connexin expression involves the use of ribozymes. Ribozymes are RNA molecules that act as enzymes, even in the complete absence of proteins. They have the catalytic activity of breaking and/or forming covalent bonds with extraordinary specificity, thereby accelerating the spontaneous rates of targeted reactions by many orders of magnitude.

Ribozymes bind to RNA through Watson-Crick base pairing and act to degrade target RNA by catalysing the hydrolysis of the phosphodiester backbone. There are several different classes of ribozymes, with the 'hammerhead' ribozyme being the most widely studied. As its name implies, the hammerhead ribozyme forms a unique secondary structure when hybridized to its target mRNA. The catalytically important residues within the ribozyme are flanked by target-complementary sequences that flank the target RNA cleavage site. Cleavage by a ribozyme requires divalent ions, such as magnesium, and is also dependent on target RNA structure and accessibility. Co-localizing a ribozyme with a target RNA within the cell through the use of localization signals greatly increases their silencing efficiency. The hammerhead ribozymes are short enough to be chemically synthesized or can be transcribed from vectors, allowing for the continuous production of ribozymes within cells.

The ability of RNA to serve as a catalyst was first demonstrated for the self-splicing group I intron of *Tetrahymena thermophila* and the RNA moiety of RNAse. After the discovery of these two RNA enzymes, RNA-mediated catalysis has been found associated with the self-splicing group II introns of yeast, fungal and plant mitochondria (as well as chloroplasts) single-stranded plant viroid and virusoid RNAs, hepatitis delta virus and a satellite RNA from *Neurospora crassa* mitochondria. Ribozymes occur naturally, but can also be artificially engineered for expression and targeting of specific sequences in cis (on the same nucleic acid strand) or trans (a noncovalently linked nucleic acid). New biochemical activities are being developed using in vitro selection protocols as well as generating new ribozyme motifs that act on substrates other than RNA.

The group I intron of *T. thermophile* was the first cis-cleaving ribozyme to be converted into a trans-reacting form, which we refer to as an intron/ribozyme, making it useful both in genomic research and as a possible therapeutic. In the trans-splicing reaction, a defective exon of a targeted mRNA can be exchanged for a correct exon that is covalently attached to the intron/ribozyme. This occurs via a splicing reaction in which the exon attached to the intron is positioned by base pairing to the target mRNA so that it can be covalently joined to the 5" end of the target transcript in a transesterification reaction. This reaction has been used to trans-splice wild-type sequences into sickle cell globin transcripts and mutant p53 transcripts and replace the expanded triplets in the 3"-UTR of protein kinase transcripts in a myotonic dystrophy allele.

The endoribonuclease RNAse P is found in organisms throughout nature. This enzyme has RNA and one or more protein components depending upon the organism from which it is isolated. The RNA component from the *Escherichia coli* and *Bacillus subtilis* enzymes can act as a site-specific cleavage agent in the absence of the protein trader certain salt and ionic conditions. Studies of the substrate requirements for human and bacterial enzymes have shown that the minimal substrates for either enzyme resemble a segment of a transfer RNA molecule. This structure can be mimicked by uniquely designed antisense RNAs, which pair to the target RNA, and serve as substrates for RNAse P-mediated, site-specific cleavage both in the test tube and in cells. It has also been shown that the antisense component can be covalently joined to the RNAse P RNA, thereby directing the enzyme only to the target RNA of interest. Investigators have taken advantage of this property in the design of antisense RNAs, which pair with target mRNAs of interest to stimulate site-specific cleavage of the target and for targeted inhibition of both herpes simplex virus and cytomegalovirus in cell culture.

A number of small plant pathogenic RNAs (viroids, satellite RNAs and virusoids), a transcript from a *N. crassa* mitochondrial DNA plasmid and the animal hepatitis delta virus undergo a self-cleavage reaction in vitro in the absence of protein. The reactions require neutral pH and $Mg^{2+}$. The self-cleavage reaction is an integral part of the in vivo rolling circle mechanism of replication. These self-cleaving RNAs can be subdivided into groups depending on the sequence and secondary structure formed about the cleavage site. Small ribozymes have been derived from a motif found in single-stranded plant viroid and virusoid RNAs. On the basis of a shared secondary structure and a conserved set of nucleotides, the term "hammerhead" has been given to one group of this self-cleavage domain. The hammerhead ribozyme is composed of 30 nucleotides. The simplicity of the hammerhead catalytic domain has made it a popular choice in the design of trans-acting ribozymes. Using Watson-Crick base pairing, the hammerhead ribozyme can be designed to cleave any target RNA. The requirements at the cleavage site are relatively simple, and virtually any UH sequence motif (where H is U, C or A) can be targeted.

A second plant-derived, self-cleavage motif, initially identified in the negative strand of the tobacco ringspot satellite RNA, has been termed the 'hairpin' or "paperclip." The hairpin ribozymes cleave RNA substrates in a reversible reaction that generates 2", Y-cyclic phosphate and 5"-hydroxT1 termini-engineered versions of this catalytic motif also cleave and turn over multiple copies of a variety of targets in trans. Substrate requirements for the hairpin include a GUC, with cleavage occurring immediately upstream of the G. The hairpin ribozyme also catalyzes a ligation reaction, although it is more frequently used for cleavage reactions.

There have been numerous applications of both hammerhead and hairpin ribozymes in cells for downregulating specific cellular and viral targets. Haseloff and Gerlach designed a hammerhead motif (Haseloff and Gerlach; Nature. 1988 Aug. 18; 334(6183):585-91) that can be engineered to cleave any target by modifying the arms that base pair with right target. Ramemzani et al. demonstrated that this hammerhead ribozyme motif had potential therapeutic applications in a study in which there was a virtual complete inhibition of viral gene expression and replication using cells engineered to express an anti-human immunodeficiency virus (HIV) gag ribozyme (Ramezani A. et al., *Frontiers in Bioscience* 7:a, 29-36; 2002).

In another aspect, modulation of the connexin expression involves the use of catalytic DNAs (or DNAzymes). Small DNAs capable of site specifically cleaving RNA targets have been developed via in vitro evolution (as no known DNA enzymes occur in nature). Two different catalytic motifs, with different cleavage site specificities have been identified. The most commonly used 10-20 enzymes bind to their RNA substrates via Watson-Crick base pairing and site specifically cleave the target RNA, as do the hammerhead and hairpin ribozymes, resulting in 2; 3"-cyclic phosphate and 5"-OH termini. Cleavage of the target mRNAs results in their destruction and the DNAzymes recycle and cleave multiple substrates. Catalytic DNAs are relatively inexpensive to synthesize and have good catalytic properties, making them useful substitutes for either antisense DNA or ribozymes.

Several applications of DNAzymes in cell culture have been published including the inhibition of veg FmRNA and consequent prevention of angiogenesis, and inhibition of expression of the bcr/abl fusion transcript characteristic of chronic myelogenous leukemia. Catalytic DNAs can be delivered exogenously, and they can be backbone-modified to in order to optimize systemic delivery in the absence of a carrier.

In another aspect of the present invention, the modulation of the constitutive connexin gene involves the use of oligonucleotides having morpholino backbone structures. Summerton, J. E. and Weller, D. D. U.S. Pat. No. 5,034,506.

In another aspect of the invention, the antisense polynucleotides may be chemically modified in order to enhance their resistance to nucleases and increase the efficacy of cell entry. For example, mixed backbone oligonucleotides (MBOs) containing segments of phosphothioate oligodeoxynucleotides and appropriately placed segments of modified oligodeoxyor oligoribonucleotides may be used. MBOs have segments of phosphorothioate linkages and other segments of other modified oligonucleotides, such as methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates, which are non-ionic, and very resistant to nucleases or 2'-O-alkyloligoribonucleotides.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

The antisense compounds useful in this invention may include oligonucleotides containing modified backbones or non-natural internucleoside linkages. Oligonucleotides having modified backbones include those that retain a phosphorus atom in the backbone and those that do not have a phosphorus atom in the backbone. In the context of this invention, modified oligonucleotides that do not have a phosphorus atom in their internucleoside backbone can also be considered to be oligonucleosides.

The antisense compounds with modified oligonucleotide backbones useful in this invention may include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In one aspect, it is contemplated that modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In one aspect, it is contemplated that oligonucleotide mimetics, both the sugar and the internucleoside linkage, i. e. the backbone of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Further teaching of PNA compounds can be found in Nielsen et al. (Science, 1991, 254, 1497-1500).

In one aspect, oligonucleotides with phosphorothioate backbones and oligonucleosides with heteroatom backbones, and in particular —CH2-NH—O—CH2-, —CH-2N(CH)3-O—CH-2 [known as a methylene (methylimino) or MMI backbone], —CH2-O—N(CH3)-CH2-, —CH2-N(CH3)-N(CH3)-CH2- and —O—N(CH3)-CH2-CH2- [wherein the native phosphodiester backbone is represented as —O—P—O—CH2-] are contemplated. In yet another aspect, oligonucleotides having morpholino and amide backbone structures are also contemplated.

In another aspect, it is contemplated that the modified oligonucleotides may also contain one or more substituted sugar moieties. For example, oligonucleotides comprising one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted C1 to C10 alkyl or C2 to C10 alkenyl and alkynyl. Particularly preferred are O[(CH2)n O]mCH3, O(CH2)n OCH3, O(CH2)2ON(CH3)2, O(CH2)n NH2, O(CH2)n CH3, O(CH2)n ONH2, and O(CH2)n ON[(CH2)n CH3)]2, where n and m are from 1 to about 10. Other preferred oligonucleotides may comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2CH2OCH, 3 also known as 2'-O-(2-methoxyethyl) or 2'-MOE) (Martin et al. Helv. Chim. Acta 1995, 78, 486-504) i.e. an alkoxyalkoxy group. Other modification includes 2'-dimethylaminooxyethoxy, i.e., a O(CH2)2ON(CH3). 2 group, also known as 2'-DMAOE, and 2'-dimethylamino-ethoxyethoxy (2'-DMAEOE), i.e., 2'-O—CH2-O—CH2-N(CH2)2.

It is further contemplated that the modifications may include 2'-methoxy (2'-O—CH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

In another aspect, it is contemplated that the oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-amincadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858-859, Kroschwitz, J. John Wiley & Sons, those disclosed by Englisch et al. (Angewandte Chemie, International Edition 1991, 30, 613-722), and those disclosed by Sanghvi, Y. S., Chapter 15, Antisense Research and Applications 1993, pages 289-302, Crooke, S. T. and Lebleu, B., ed., CRC Press. Certain of these nucleobases are particularly useful for increasing the binding affinity of the oligomeric compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications 1993, CRC Press, Boca Raton, pages 276-278) and are presently preferred base substitutions, even more particularly when combined with 2'-O-methoxyethyl sugar modifications.

In another aspect, it is contemplated that the modification of the oligonucleotides involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 1989, 86, 6553-6556), cholic acid (Manoharan et al., Bioorg. Med. Chem. Lett. 1994, 4, 1053-1059), a thioether, e.g., hexyl-S-tritylthiol (Manoharan et al., Ann. N.Y. Acad. Sci. 1992, 660, 306-309; Manoharan et al., Bioorg. Med. Chem. Let. 1993, 3, 2765-2770), a thiocholesterol (Oberhauser et al., Nucl. Acids Res. 1992, 20, 533-538), an aliphatic chain, e.g., dodecandiol or undecyl residues (Saison-Behmoaras et al., EMBO J. 1991, 10, 1111-1118; Kabanov et al., FEBS Lett. 1990, 259, 327-330; Svinarchuk et al., Biochimie 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651-3654; Shea et al., Nucl. Acids Res. 1990, 18, 3777-3783), a polyamine or a polyethylene glycol chain (Manoharan et al., Nucleosides & Nucleotides 1995, 14, 969-973), or adamantane acetic acid (Manoharan et al., Tetrahedron Lett. 1995, 36, 3651-3654), a palmityl moiety (Mishra et al., Biochim. Biophys. Acta 1995, 1264, 229-237), or an octadecylamine or hexylamino-carbonyl-oxycholesterol moiety (Crooke et al., J. Pharmacol. Exp. Ther. 1996, 277, 923-937).

Also contemplated are the use of oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g. fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P═S) and phosphodiester (P═O) backbone linkages or with regions of MMI and P═S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—CH2CH2OCH3) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides may bear a 2'-O-methoxyethyl (—O—CH2CH2 OCH3) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 21-O-methoxyethyl modifications, oligonucleotides containing other modifications which enhance antisense efficacy, potency or target affinity are also contemplated.

The present invention also provides polynucleotides (for example, DNA, RNA, PNA or the like) that bind to double-stranded or duplex connexin nucleic acids (for example, in a folded region of the connexin RNA or in the connexin gene), forming a triple helix-containing, or "triplex" nucleic acid. Triple helix formation results in inhibition of connexin expression by, for example, preventing transcription of the connexin gene, thus reducing or eliminating connexin activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides are constructed using the base-pairing rules of triple helix formation (see, for example, Cheng et al., J. Biol. Chem. 263: 15110 (1988); Ferrin and Camerini-Otero, Science 354:1494 (1991); Ramdas et al., J. Biol. Chem. 264:17395 (1989); Strobel et al., Science 254:1639 (1991); and Rigas et al., Proc. Natl. Acad. Sci. U.S.A. 83: 9591 (1986)) and the connexin mRNA and/or gene sequence. Typically, the triplex-forming oligonucleotides comprise a specific sequence of from about 10 to about 25 nucleotides or longer "complementary" to a specific sequence in the connexin RNA or gene (i.e., large enough to form a stable triple helix, but small enough, depending on the mode of delivery, to administer in vivo, if desired). In this context, "complementary" means able to form a stable triple helix. In one embodiment, oligonucleotides are designed to bind specifically to the regulatory regions of the connexin gene (for example, the connexin 5'-flanking sequence, promoters, and enhancers) or to the transcription initiation site, (for example, between −10 and +10 from the transcription initiation site). For a review of recent therapeutic advances using triplex DNA, see Gee et al., in Huber and Carr, 1994, Molecular and Immunologic Approaches, Futura Publishing Co, Mt Kisco N.Y. and Rininsland et al., 1997, *Proc. Natl. Acad. Sci. USA* 94:5854.

The present invention also provides ribozymes useful for inhibition of connexin activity. The ribozymes bind and specifically cleave and inactivate connexin mRNA. Useful ribozymes can comprise 5'- and 3'-terminal sequences complementary to the connexin mRNA and can be engineered by one of skill on the basis of the connexin mRNA sequence. It is contemplated that ribozymes provided herein include those having characteristics of group I intron ribozymes (Cech, *Biotechnology* 13:323 (1995)) and others of hammerhead ribozymes (Edgington, *Biotechnology* 10:256 (1992)).

Ribozymes include those having cleavage sites such as GUA, GUU and GUC. Short RNA oligonucleotides between 15 and 20 ribonucleotides in length corresponding to the region of the target connexin gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assays, or by testing for in vitro ribozyme activity in accordance with standard procedures known in the art.

Further contemplated are antisense compounds in which antisense and ribozyme functions can be combined in a single oligonucleotide. Moreover, ribozymes can comprise one or more modified nucleotides or modified linkages between nucleotides, as described above in conjunction with the description of illustrative antisense oligonucleotides provided herein.

The present invention also provides polynucleotides useful for inhibition of connexin activity by methods such as RNA interference (RNAi) This and other techniques of gene suppression are well known in the art. A review of this technique is found in *Science* 288:1370-1372 (2000). RNAi operates on a post-transcriptional level and is sequence specific. The process comprises introduction of RNA with partial or fully double-stranded character, or precursors of or able to encode such RNA into the cell or into the extracellular environment.

As described by Fire et al., U.S. Pat. No. 6,506,559, the RNA may comprise one or more strands of polymerized ribonucleotide. The double-stranded structure may be formed by a single self-complementary RNA strand or two complementary RNA strands. The RNA may include modifications to either the phosphate-sugar backbone or the nucleosides. RNA duplex formation may be initiated either inside or outside the cell.

Studies have demonstrated that one or more ribonucleases specifically bind to and cleave double-stranded RNA into short fragments. The ribonuclease(s) remains associated with these fragments, which in turn specifically bind to complementary mRNA, i.e., specifically bind to the transcribed mRNA strand for the connexin gene. The mRNA for the connexin gene is also degraded by the ribonuclease(s) into short fragments, thereby obviating translation and expression of the connexin gene, and so inhibiting connexin activity. Additionally, an RNA polymerase may act to facilitate the synthesis of numerous copies of the short fragments, which exponentially increases the efficiency of the system. A unique feature of this gene suppression pathway is that silencing is not limited to the cells where it is initiated. The gene-silencing effects may be disseminated to other parts of an organism and even transmitted through the germ line to several generations.

In one aspect, the double-stranded (ds)RNA-dependent gene specific post transcriptional silencing strategy of RNAi involves the use of short interfering RNAs (siRNA). The use of the general RNAi approach is subject to certain limitations, including the nonspecific antiviral defense mechanism in mammalian cells activated in response to long dsRNA molecules (Gil J, Esteban M, "Induction of apoptosis by the dsRNA-dependent protein kinase (PKR): Mechanisms of action". Apoptosis 2000, 5:107-114). Advances in the field have been made with the demonstration that synthetic duplexes of 21 nucleotide RNAs could mediate gene specific RNAi in mammalian cells without invoking generic antiviral defense mechanisms (Elbashir S, et al., "Duplexes of 21-nucleotide RNAs mediate RNA interference in cultured mammalian cells". Nature 2001, 411:494-498; Caplen N. et al., Proc Natl Acad Sci 2001, 98:9742-9747). Thus, siRNAs are increasingly being recognized as powerful tools for gene-specific modulation.

As described herein, RNAi includes to a group of related gene-silencing mechanisms sharing many common biochemical components in which the terminal effector molecule is for example, but not limited to, a small 21-23-nucleotide antisense RNA. One mechanism uses a relatively long, dsRNA 'trigger; which is processed by the cellular enzyme Dicer into short, for example, but not limited to, 21-23-nucleotide dsRNAs, referred to as siRNAs. The strand of the siRNA complementary to the target RNA becomes incorporated into a multi-protein complex termed the RNA-induced silencing complex (RISC), where it serves as a guide for endonucleolytic cleavage of the mRNA strand within the target site. This leads to degradation of the entire mRNA; the antisense siRNA can then be recycled. In lower organisms, RNA-dependent RNA polymerase also uses the annealed guide siRNA as a primer, generating more dsRNA front the target, which serves in turn as a Dicer substrate, generating more siRNAs and amplifying the siRNA signal. This pathway is commonly used as a viral defense mechanism in plants.

As described herein, the siRNA may consist of two separate, annealed single strands of for example, but not limited to, 21-23 nucleotides, where the terminal two 3"-nucleotides are unpaired (3" overhang). Alternatively, the siRNA may be in the form of a single stem-loop, often referred to as a short hairpin RNA (shRNA). Typically, but not always, the antisense strand of shRNAs is also completely complementary to the sense partner strand of the si/shRNA.

In mammalian cells, long dsRNAs (usually greater than 30 nucleotides in length) trigger the interferon pathway, activating protein kinase R and 2; 5"-oligoadenylate synthetase. Activation of the interferon pathway can lead to global downregulation of translation as well as global RNA degradation. However, shorter siRNAs exogenously introduced into mammalian cells have been reported to bypass the interferon pathway.

The siRNA antisense product can also be derived from endogenous microRNAs. In human cells, regardless of the initial form (siRNAs and microRNAs) or processing pathway, a final mature for example, but not limited to, 21-23-nucleotide antisense RNA that is completely homologous to the mRNA will direct mRNA cleavage. In general, the effect of mismatches between siRNAs and target sites can vary from almost none to complete abrogation of activity, for reasons that are only partially understood; however, in at least one case, partial homology resulted in mRNA translation inhibition. In general, siRNA with target mismatches designed to mimic a prototypical microRNA-target interaction can mediate varying degrees of translational repression, depending on both the specific interaction and the number of target sites in the mRNA. RNAi can be activated by either exogenous delivery of preformed siRNAs or via promoter-based expression of siRNAs or shRNAs.

Short interfering RNAs (siRNA) can be chemically synthesized or generated by DNA-based vectors systems. In general, this involves transcription of short hairpin (sh) RNAs that are efficiently processed to form siRNAs within cells (Paddison P, Caudy A, Hannon G: Stable suppression of gene expression by RNAi in mammalian cells. *Proc Natl Acad Sci U.S.A* 2002, 99:1443-1448; Paddison P, Caudy A, Bernstein E, Hannon G, Conklin D: Short hairpin RNAs (shRNAs) induce sequence-specific silencing in mammalian cells. *Genes & Dev* 2002, 16:948-958; Sui G, et al., *Proc Natl Acad Sci* 2002, 8:5515-5520; Brummelkamp T, et al., *Science* 2002, 296:550-553). Therefore, in the context, siRNAs can be employed as an effective strategy for the tissue-specific targeting and modulation of gene expression.

The oligonucleotides used in accordance with this invention may be conveniently and routinely made through the well-known technique of solid phase synthesis. Equipment for such synthesis is sold by several vendors known in the art. Any other means for such synthesis may also be employed; the actual synthesis of the oligonucleotides is well recognized in the art. It is well known to use similar techniques to prepare oligonucleotides such as the phosphorothioates and 2'-alkoxy or 21-alkoxyalkoxy derivatives, including 2'-O-methoxyethyl oligonucleotides (Martin, P. Helv. Chim. Acta 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

Methods

In another aspect, the invention includes methods of treating a subject (e.g. patient) by administering antisense compounds to the subject. Generally, these methods include methods for tissue engineering and methods for reducing tissue damage associated with medical procedures, including but not limited to ophthalmic procedures.

The method may comprise, for example, administering an antisense compound to the eye of said subject in an amount sufficient to inhibit the expression of a human connexin protein in the eye or in cells associated with the eye of the subject. While it is preferred that the expression of human connexin protein is inhibited, it is envisioned that other proteins may be targets for modulation by the antisense compounds, either alone of in combination with antisense compounds which inhibit the expression of human connexins.

In certain embodiments, the ophthalmic procedure is an ophthalmic surgery, including but not limited to an excimer laser photorefractive keratectomy, a cataract extraction, corneal transplant, a surgery to correct refraction, a radial keratotomy, a glaucoma filtration surgery, a keratoplasty, an excimer laser photorefractive keratectomy, a corneal transplant, a surgery to correct refraction, a ocular surface neoplasm excision, a conjunctival or amniotic membrane graft, a pterygium and pingeculae excision, a ocular plastic surgery, a lid tumour excision, a reconstructive lid procedures for congenital abnormalities, an ectropian and entropian eyelid repair, a strabismus surgery (occular muscle), a penetrating eye trauma.

In certain embodiments, antisense compounds provided herein are administered by local or topical administration. Antisense compounds provided herein can also be administered, for example, systemically or by intraocular injection.

Antisense compounds provided herein can be administered to a subject at a predetermined time, for example, relative to the formation of a wound, such as that occurs in an ophthalmic procedure (e.g. surgical). For example, antisense compounds can be administered before an ophthalmic procedure is performed, during an ophthalmic procedure, or after an ophthalmic procedure. For example, antisense compounds may be administered to a subject within minutes or hours before or after an ophthalmic procedure is performed.

In certain embodiments, an antisense compound is administered after an ophthalmic procedure is performed, and for example the antisense compound is administered within about 4 hours of the procedure, within about 3 hours of the procedure, and more typically within about 2 hours of the ophthalmic procedure, or within about 1 hour of an ophthalmic procedure. Alternatively, an antisense compound may be administered within minutes of an ophthalmic procedure, for example within 5, 10, 15, 20, 30, 45, minutes of an ophthalmic procedure. Antisense compounds may also be administered after 4 hours of an ophthalmic procedure.

In another aspect, antisense compounds provided herein may be administered in a methods to effect tissue engineering. In these embodiments, and some others provided herein, antisense compounds are typically administered over a longer periods of time, for example over the course of days, weeks, months, or even longer, and can be administered independent of a particular procedure performed on a patient, such as one performed on an eye.

Antisense compounds provided herein may be administered in conjunction with a method that increases the thickness of cornea tissue in a subject, including in methods that are not associated with an ophthalmic procedure, and in methods in which antisense compounds are administered in association with an ophthalmic procedure (e.g. surgery). Antisense compounds provided herein may be administered in conjunction with a method that promotes healing or prevents tissue damage, for example in cells associated with the cornea of the subject (e.g. corneal cells). Antisense compounds provided herein may be administered in conjunction with a method that reduces scarring in the eye of a subject.

Antisense compounds provided herein may be administered in conjunction with a method that reduces hazing in the eye of a subject. Antisense compounds provided herein may be administered in conjunction with a method that modulates hypercellularity associated with myofibroblast differentiation associated with a site of a laser induced lesion, preferably in the 24 hr to 48 hr post-surgery period. Antisense compounds provided herein may be administered in conjunction with a method that modulates stromal remodeling and reduces haze associated with a site of a laser-induced lesion, preferably in the 24 hr to 72 hr post-surgery period. Antisense compounds provided herein may be administered in conjunction with a method that increases epithelial cell movement in the eye of a subject. Antisense compounds provided herein may be administered in conjunction with a method that results in an increase in epithelial cell movement within 12 hours of administering an antisense compound to the eye of the subject. Antisense compounds provided herein may be administered in conjunction with a method that results in an increase in epithelial cell movement within 24 hours of administering the antisense compound to the eye of the subject. Antisense compounds provided herein may be administered in conjunction with a method that prevents an increase in stromal cell density. Antisense compounds provided herein may be administered in conjunction with a method that inhibits stromal edema associated with a site of a laser-induced lesion in the 24 hr to 72 hr post-surgery period. Antisense compounds provided herein may be administered in conjunction with a method that reduces epithelial hyperplasia in the 24 hr to 72 hr post-surgery. Antisense compounds provided herein may be administered in conjunction with a method that reduces myofibroblast activation up to 1 week post-surgery. Antisense compounds provided herein may be administered in conjunction with a method that modulates cell differentiation that modifies the extracellular matrix. Antisense compounds provided herein may be administered in conjunction with a method that reduces cell proliferation.

In certain embodiments, the antisense compound decreases scar formation. In certain embodiments, the antisense compound reduces inflammation. In certain embodiments, the antisense compound promotes wound healing. In certain preferred embodiments, the antisense compound is used in association with a surgical implantation procedure. In certain preferred embodiments, the antisense compound is directed to connexin 43 and is administered to regulate epithelial basal cell division and growth. In certain embodiments, the antisense compound is directed to connexin 31.1 and is administered to regulate outer layer keratinisation.

In other embodiments, the method promotes healing or prevents tissue damage in cells associated with the cornea of the subject. According to certain embodiment, antisense compounds are used in methods that increase the thickness of cornea tissue in a subject, or in a method that results in the reduction of tissue damage in corneal cells of a subject, or in a method that results in the reduction of tissue damage in cells associated with the cornea of a subject, or in a method performed in association with an excimer laser photorefractive keratectomy procedure in a subject, or in a method that modulates hypercellularity associated with myofibroblast differentiation associated with a site of a laser induced lesion, preferably in the 24 hr to 48 hr post-surgery period, or in a method that modulates stromal remodeling and reduces haze associated with a site of a laser-induced lesion, preferably in the 24 hr to 72 hr post-surgery period, or in a method that inhibits stromal edema associated with a site of a laser induced lesion in the 24 hr to 72 hr post-surgery period, or in a method that reduces epithelial hyperplasia, preferably in the 24 hr to 72 hr post-surgery, or in a method that reduces myofibroblast activation up to 1 week post-surgery, or in a method that modulates cell differentiation that modifies the extracellular matrix, or in a method that reduces cell proliferation.

In certain embodiments, the ophthalmic procedure is cataract extraction. In a other embodiments, the ophthalmic procedure is a corneal transplant. In other embodiments, the ophthalmic surgical procedure is surgery to correct refraction. In a other embodiments, the ophthalmic procedure is radial keratotomy. In a other embodiments, the ophthalmic procedure is glaucoma filtration surgery. In still other embodiments, the ophthalmic procedure is keratoplasty.

In certain embodiments, the antisense compound or composition is administered by local or topical administration. In certain embodiments, the antisense compound or composition is administered by direct application in the surgical wound. In certain embodiments, the antisense compound or composition is administered by intraocular injection. In certain embodiments, the antisense compound or composition is administered before the surgical procedure is performed. In certain embodiments, the antisense compound or composition is administered during the surgical procedure. In certain non-limiting embodiments, the antisense compound or composition is administered within about 15 minutes before an ophthalmic procedure is performed or up to about 2 hours after an ophthalmic procedure is performed. In certain other embodiments, for example for tissue engineering, antisense compounds provided herein may be administered for days or even months.

In certain further embodiments, compounds and compositions are used to promote healing or to prevent tissue damage in cells associated with cornea, where the cells associated with the cornea may be any cell in the eye, including but not limited to corneal cells. The agents provided herein, including antisense compounds, may increase the thickness of cornea tissue in a subject. In certain embodiments, the antisense compound is used in combination with another compound useful for reducing tissue damage or promoting healing. For example, the antisense compounds may be coadministered with a growth factor, cytokine, or the like, including but not limited to FGF, NGF, NT3, PDGF, TGF, VEGF, BDGF, EGF, KGF, integrins, interleukins, plasmin, and semaphorins.

In another aspect, a pharmaceutical composition for reducing tissue damage associated with ophthalmic surgery is provided. The pharmaceutical composition is suitably formulated for topical or local administration to the eye of a subject comprising an antisense compound present in an amount sufficient to inhibit the expression of a human connexin protein in cells associated with the eye of the subject. The antisense compound is preferably targeted to at least about 8 nucleobases of a nucleic acid molecule encoding a connexin having a nucleobase sequence selected from SEQ ID NO:12-31. In certain embodiments, the antisense compounds are in the form of a pharmaceutical composition comprising a pharmaceutically acceptable carrier or vehicle and the agent or antisense compound is present in an amount effective to promote wound healing in a subject. In certain embodiments, the pharmaceutical compositions may be, for example, in a form suitable for topical administration, including in a form suitable for topical or local administration to the eye of a subject. In certain further embodiments, the compositions and formulations may be in the form of a gel, a cream, or any of the forms described herein.

In another aspect, methods of treating an injury to the central nervous system are provided. The method comprising administering an antisense compound to a site proximal to a preexisting wound of the central nervous system in association with a surgical procedure performed on a patient to treat said injury to the central nervous system, wherein said antisense compound is targeted to at least about 8 nucleobases of a nucleic acid molecule encoding a connexin having a nucleobase sequence selected from SEQ ID NO:12-31. In certain embodiments of the method, the antisense compound is administered to reduce neuronal loss due to physical trauma to the spinal cord. In certain embodiments of the method, the antisense compound is administered to a site adjacent to a wound that is the result of trauma. In certain embodiments of the method, the antisense compound is administered to a site adjacent to a wound that is the result of a surgery. In certain embodiments of the method, the antisense compound is administered to a site adjacent to a spinal cord injury. In certain embodiments of the method, the antisense compound is directed to connexin 43 and is administered to regulate epithelial basal cell division and growth. In certain embodiments of the method, the antisense compound promotes wound healing. In certain embodiments of the method, the antisense compound reduces inflammation. In certain embodiments of the method, the antisense compound decreases scar formation. In certain embodiments of the method, the injury to the central nervous system is a spinal cord injury. In certain embodiments of the method, the antisense compound is administered to a patient at least about 24 hours after a physical trauma to the spinal cord. In certain embodiments of the method, the antisense compound is used in association with a surgical implantation procedure. In certain further embodiments of the method, the surgical implantation procedure is associated with an implant pre-treated with antisense-compound to promote wound healing. In another aspect, antisense compounds capable of promoting the regeneration of neurons in association with a procedure for the treatment of a preexisting wound in a patient characterized by neuronal loss are provided. In certain embodiments, the agents are antisense compounds up to 40 nucleobases in length that are targeted to at least about 8 nucleobases of a nucleic acid molecule encoding a human connexin and the antisense compound inhibits the expression of one or more human connexin in association with a procedure to promote the regeneration neurons for the treatment of a preexisting wound in a patient. The wound includes those characterized by neuronal loss. Connexins that may be targeted include connexins having a nucleobase sequence selected from SEQ ID NO:12-31. In these embodiments, the antisense compounds may be administered to a patient at least 24 hours after a physical trauma to the spinal cord of said patient that resulted in a neuronal loss. The antisense compounds may be administered to a patient at more than 24 hours after a physical trauma to the spinal cord for times periods of weeks, months, or years after the physical trauma that resulted in a neuronal loss.

In certain embodiments of pharmaceutical compositions and methods, the antisense compound is targeted to at least about 8 nucleobases of a nucleic acid molecule encoding human connexin 30 or human connexin 37. Preferably, the antisense compound inhibits the expression of a human connexin 30 or 37 protein in cells associated with the eye of a patient. Other pharmaceutical compositions comprise an antisense compound targeted to at least about 8 nucleobases of a nucleic acid molecule encoding a connexin (e.g. human) having a nucleobase sequence selected from SEQ ID NO:12-31, and preferably the antisense compound inhibits the expression of a human connexin in association with a procedure to promote the regeneration neurons for the treatment of a preexisting wound in a patient that is characterized by neuronal loss.

Pharmaceutical Compositions

In another aspect, the invention includes pharmaceutical compositions comprising antisense compounds. In one embodiment, a pharmaceutical composition is provided for reducing tissue damage associated with an ophthalmic procedure (e.g. surgery), such that the pharmaceutical composition is formulated for topical or local administration to the eye of a subject and it comprises an antisense compound present in an amount sufficient to inhibit the expression of a human connexin protein in cells associated with the eye of the subject. In certain embodiments, the antisense compound is targeted to at least about 8 nucleobases of a nucleic acid molecule encoding a connexin (e.g. human) having a nucleobase sequence selected from SEQ ID NO:12-31. In certain embodiments, the pharmaceutical composition includes a pharmaceutically acceptable carrier comprising a buffered pluronic acid or gel, for example up to about 30% pluronic acid in phosphate buffered saline. Antisense composition may comprise different amounts of pluronic acid or gel, including without limitation in amounts up to about 5% pluronic acid in phosphate buffered saline, up to about 10% pluronic acid in phosphate buffered saline, up to about 15% pluronic acid in phosphate buffered saline, up to about 20% pluronic acid in phosphate buffered saline, up to about 25% pluronic acid in phosphate buffered saline, and up to about 30% pluronic acid in phosphate buffered saline.

The antisense compounds provided herein may also include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids and prodrugs of such nucleic acids. "Pharmaceutically acceptable salts" are physiologically and pharmaceutically acceptable salts of the nucleic acids provided herein: i.e., salts that retain the desired biological activity of the parent compound and do not impart undesired toxicological effects thereto (see, for example, Berge et al., J. of Pharma Sci. 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides provided herein may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides may be prepared as SATE [(S-acetyl-2-thioethyl) phosphate] derivatives according to the methods disclosed in WO 93/24510 to Gosselin et al., published Dec. 9, 1993.

Antisense compounds may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide.

Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives. Pharmaceutical compositions comprising the oligonucleotides provided herein may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 1991, 8, 91-192; Muranishi, Critical Reviews in Therapeutic Drug Carrier Systems 1990, 7, 1-33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Lee et al., Critical Reviews in Therapeutic Drug Carrier Systems 1991, page 92; Muranishi, Critical Reviews in Therapeutic Drug Carrier Systems 1990, 7, 1; El-Hariri et al., J. Pharm. Pharmacol. 1992 44, 651-654).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al. McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems 1991, page 92; Muranishi, Critical Reviews in Therapeutic Drug Carrier Systems 1990, 7, 1-33; Buur et al., J. Control Rel. 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems 1991, page 92); and perfluorochemical emulsions, such as FC-43 (Takahashi et al., J. Pharm. Phamacol. 1988, 40, 252-257). Non-surfactants include, for example, unsaturated cyclic ureas, 1-alkyl- and 1-alkenylazacyclo-alkanone derivatives (Lee et al., Critical Reviews in Therapeutic Drug Carrier Systems 1991, page 92); and non-steroidal anti-inflammatory agents such as diclofenac sodium, indomethacin and phenylbutazone (Yamashita et al., J. Pharm. Pharmacol. 1987, 39, 621-626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions provided herein.

Regardless of the method by which the oligonucleotides are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708).

The antisense polynucleotides may be present in a substantially isolated form. It will be understood that the product may be mixed with carriers or diluents which will not interfere with the intended purpose of the product and still be regarded as substantially isolated. A product may also be in a substantially purified form, in which case it will generally comprise 90%, e.g. at least about 95%, 98% or 99% of the polynucleotide or dry mass of the preparation.

The antisense polynucleotides may be administered topically (at the site to be treated). Preferably the antisense polynucleotides are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration. Uptake of nucleic acids by mammalian cells is enhanced by several known transfection techniques, for example, those that use transfection agents. The formulation which is administered may contain such agents. Example of these agents include cationic agents (for example calcium phosphate and DEAE-dextran) and lipofectants (for example Lipofectam™ and Transfectam™).

In one aspect, the oligonucleotides may require site-specific delivery. They also require delivery over an extended period of time. While clearly the delivery period will be dependent upon both the site at which the down-regulation is to be induced and the therapeutic effect which is desired, continuous delivery for 24 hours or longer will often be required. In on aspect of the present invention, this is achieved by inclusion of the antisense compounds in a formulation together with a pharmaceutically acceptable carrier or vehicle, particularly in the form of a formulation for topical administration. In particular, topical formulations such as creams, drops, and other described herein can be employed to regulate epithelial basal cell division and growth (using antisense compounds targeted to connexin 43) and outer layer keratinization (using antisense compounds targeted to connexin31.1).

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral administration may include sterile aqueous solutions which may also contain buffers, diluents and other suitable additives. In some cases it may be more effective to treat a patient with an oligonucleotide in conjunction with other traditional therapeutic modalities in order to increase the efficacy of a treatment regimen. As used herein, the term “treatment regimen” is meant to encompass therapeutic, palliative and prophylactic modalities.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50 s found to be effective in vitro and in in vivo animal models. In general, dosage is from 0.01 mg/kg to 100 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 mg/kg to 100 mg per kg of body weight, once or more daily, to once every 20 years. In the treatment or prevention of conditions which require connexin modulation an appropriate dosage level will generally be about 0.001 to 100 mg per kg patient body weight per day which can be administered in single or multiple doses. Preferably, the dosage level will be about 1 to about 40 mg/kg per day.

The oligonucleotides of this invention can be used in diagnostics, therapeutics, prophylaxis, and as research reagents and in kits. Since the oligonucleotides of this invention hybridize to nucleic acids encoding connexin, sandwich, calorimetric and other assays can easily be constructed to exploit this fact. Provision of means for detecting hybridization of oligonucleotide with the connexin genes or mRNA can routinely be accomplished. Such provision may include enzyme conjugation, radiolabel ling or any other suitable detection systems. Kits for detecting the presence or absence of connexin may also be prepared.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

Exemplary connexins that may be targeted in certain embodiments described herein include, but are not limited to the following.

```
Human Cx 43, α1 (SEQ ID NO: 12)
LOCUS       NM_000165   3088 bp   mRNA   linear
            PRI 26-OCT-2004
DEFINITION  Homo sapiens gap junction protein,
            alpha 1, 43kDa (connexin 43) (GJA1),
            mRNA.
     1  acaaaaaagc ttttacgagg tatcagcact tttctttcat
        tagggggaag gcgtgaggaa
    61  agtaccaaac agcagcggag ttttaaactt taaatagaca
        ggtctgagtg cctgaacttg
   121  ccttttcatt ttacttcatc ctccaaggag ttcaatcact
        tggcgtgact tcactacttt
   181  taagcaaaag agtggtgccc aggcaacatg ggtgactgga
        gcgccttagg caaactcctt
   241  gacaaggttc aagcctactc aactgctgga gggaaggtgt
        ggctgtcagt acttttcatt
   301  ttccgaatcc tgctgctggg gacagcggtt gagtcagcct
        ggggagatga gcagtctgcc
   361  tttcgttgta acactcagca acctggttgt gaaaatgtct
        gctatgacaa gtctttccca
   421  atctctcatg tgcgcttctg ggtcctgcag atcatatttg
        tgtctgtacc cacactcttg
   481  tacctggctc atgtgttcta tgtgatgcga aaggaagaga
        aactgaacaa gaaagaggaa
   541  gaactcaagg ttgcccaaac tgatggtgtc aatgtggaca
        tgcacttgaa gcagattgag
   601  ataaagaagt tcaagtacgg tattgaagag catggtaagg
        tgaaaatgcg aggggggttg
   661  ctgcgaacct acatcatcag tatcctcttc aagtctatct
        ttgaggtggc cttcttgctg
   721  atccagtggt acatctatgg attcagcttg agtgctgttt
        acacttgcaa aagagatccc
   781  tgcccacatc aggtggactg tttcctctct cgccccacgg
        agaaaaccat cttcatcatc
```

-continued

```
   841  ttcatgctgg tggtgtcctt ggtgtccctg gccttgaata
        tcattgaact cttctatgtt
   901  ttcttcaagg gcgttaagga tcgggttaag ggaaagagcg
        acccttacca tgcgaccagt
   961  ggtgcgctga gccctgccaa agactgtggg tctcaaaaat
        atgcttattt caatggctgc
  1021  tcctcaccaa ccgctcccct ctcgcctatg tctcctcctg
        ggtacaagct ggttactggc
  1081  gacagaaaca attcttcttg ccgcaattac aacaagcaag
        caagtgagca aaactgggct
  1141  aattacagtg cagaacaaaa tcgaatgggg caggcgggaa
        gcaccatctc taactcccat
  1201  gcacagcctt ttgatttccc cgatgataac cagaattcta
        aaaaactagc tgctggacat
  1261  gaattacagc cactagccat tgtggaccag cgaccttcaa
        gcagagccag cagtcgtgcc
  1321  agcagcagac ctcggcctga tgacctggag atctagatac
        aggcttgaaa gcatcaagat
  1381  tccactcaat tgtggagaag aaaaaaggtg ctgtagaaag
        tgcaccaggt gttaattttg
  1441  atccggtgga ggtggtactc aacagcctta ttcatgaggc
        ttagaaaaca caaagacatt
  1501  agaataccta ggttcactgg gggtgtatgg ggtagatggg
        tggagaggga ggggataaga
  1561  gaggtgcatg ttggtattta aagtagtgga ttcaaagaac
        ttagattata aataagagtt
  1621  ccattaggtg atacatagat aagggctttt tctccccgca
        aacaccccta agaatggttc
  1681  tgtgtatgtg aatgagcggg tggtaattgt ggctaaatat
        ttttgtttta ccaagaaact
  1741  gaaataattc tggccaggaa taaatacttc ctgaacatct
        taggtctttt caacaagaaa
  1801  aagacagagg attgtcctta agtccctgct aaaacattcc
        attgttaaaa tttgcacttt
  1861  gaaggtaagc tttctaggcc tgaccctcca ggtgtcaatg
        gacttgtgct actatatttt
  1921  tttattcttg gtatcagttt aaaattcaga caaggcccac
        agaataagat tttccatgca
  1981  tttgcaaata cgtatattct tttccatcc acttgcacaa
        tatcattacc atcacttttt
```

-continued

```
2041 catcattcct cagctactac tcacattcat ttaatggttt
     ctgtaaacat ttttaagaca
2101 gttgggatgt cacttaacat tttttttttt tgagctaaag
     tcagggaatc aagccatgct
2161 taatatttaa caatcactta tatgtgtgtc gaagagtttg
     ttttgtttgt catgtattgg
2221 tacaagcaga tacagtataa actcacaaac acagatttga
     aaataatgca catatggtgt
2281 tcaaatttga acctttctca tggatttttg tggtgtgggc
     caatatggtg tttacattat
2341 ataattcctg ctgtggcaag taaagcacac tttttttttc
     tcctaaaatg tttttccctg
2401 tgtatcctat tatggatact ggttttgtta attatgattc
     tttattttct ctccttttt
2461 taggatatag cagtaatgct attactgaaa tgaatttcct
     ttttctgaaa tgtaatcatt
2521 gatgcttgaa tgatagaatt ttagtactgt aaacaggctt
     tagtcattaa tgtgagagac
2581 ttagaaaaaa tgcttagagt ggactattaa atgtgcctaa
     atgaattttg cagtaactgg
2641 tattcttggg ttttcctact taatacacag taattcagaa
     cttgtattct attatgagtt
2701 tagcagtctt ttggagtgac cagcaacttt gatgtttgca
     ctaagatttt atttggaatg
2761 caagagaggt tgaaagagga ttcagtagta cacatacaac
     taatttattt gaactatatg
2821 ttgaagacat ctaccagttt ctccaaatgc cttttttaaa
     actcatcaca gaagattggt
2881 gaaaatgctg agtatgacac ttttcttctt gcatgcatgt
     cagctacata aacagttttg
2941 tacaatgaaa attactaatt tgtttgacat tccatgttaa
     actacggtca tgttcagctt
3001 cattgcatgt aatgtagacc tagtccatca gatcatgtgt
     tctggagagt gttctttatt
3061 caataaagtt ttaatttagt ataaacat
```

Human Cx 46, α3 (SEQ ID NO: 13)

```
LOCUS       NM_021954   1308 bp   mRNA   linear
            PRI 27-OCT-2004
DEFINITION  Homo sapiens gap junction protein,
            alpha 3, 46kDa (connexin 46) (GJA3),
            mRNA.
   1 atgggcgact ggagctttct gggaagactc ttagaaaatg
     cacaggagca ctccacggtc
```

-continued

```
  61 atcggcaagg tttggctgac cgtgctgttc atcttccgca
     tcttggtgct gggggccgcg
 121 gcggaggacg tgtggggcga tgagcagtca gacttcacct
     gcaacaccca gcagccgggc
 181 tgcgagaacg tctgctacga cagggccttc cccatctccc
     acatccgctt ctgggcgctg
 241 cagatcatct tcgtgtccac gcccaccctc atctacctgg
     gccacgtgct gcacatcgtg
 301 cgcatggaag agaagaagaa agagagggag gaggaggagc
     agctgaagag agagagcccc
 361 agccccaagg agccaccgca ggacaatccc tcgtcgcggg
     acgaccgcgg cagggtgcgc
 421 atggccgggg cgctgctgcg gacctacgtc ttcaacatca
     tcttcaagac gctgttcgag
 481 gtgggcttca tcgccggcca gtactttctg tacggcttcg
     agctgaagcc gctctaccgc
 541 tgcgaccgct ggccctgccc caacacggtg gactgcttca
     tctccaggcc cacggagaag
 601 accatcttca tcatcttcat gctggcggtg gcctgcgcgt
     ccctgctgct caacatgctg
 661 gagatctacc acctgggctg gaagaagctc aagcagggcg
     tgaccagccg cctcggcccg
 721 gacgcctccg aggccccgct ggggacagcc gatcccccgc
     ccctgccccc cagctcccgg
 781 ccgcccgccg ttgccatcgg gttcccaccc tactatgcgc
     acaccgctgc gcccctggga
 841 caggcccgcg ccgtgggcta ccccggggcc ccgccaccag
     ccgcggactt caaactgcta
 901 gccctgaccg aggcgcgcgg aaagggccag tccgccaagc
     tctacaacgg ccaccaccac
 961 ctgctgatga ctgagcagaa ctgggccaac caggcggccg
     agcggcagcc cccggcgctc
1021 aaggcttacc cggcagcgtc cacgcctgca gcccccagcc
     ccgtcggcag cagctccccg
1081 ccactcgcgc acgaggctga ggcgggcgcg gcgcccctgc
     tgctggatgg gagcggcagc
1141 agtctggagg ggagcgccct ggcagggacc cccgaggagg
     aggagcaggc cgtgaccacc
1201 gcggcccaga tgcaccagcc gcccttgccc ctcggagacc
     caggtcgggc cagcaaggcc
```

-continued 1261 agcagggcca gcagcgggcg ggccagaccg gaggacttgg
ccatctag

Human Cx 37, α4 (SEQ ID NO: 14)
LOCUS NM_002060 1601 bp mRNA linear PRI 26-OCT-2004
DEFINITION Homo sapiens gap junction protein, alpha 4, 37kDa (connexin 37) (GJA4), mRNA.

1 ctccggccat cgtccccacc tccacctggg ccgcccgcga
ggcagcggac ggaggccggg
61 agccatgggt gactggggct tcctggagaa gttgctggac
caggtccgag agcactcgac
121 cgtggtgggt aagatctggc tgacggtgct cttcatcttc
cgcatcctca tcctgggcct
181 ggccggcgag tcagtgtggg gtgacgagca gtcagatttc
gagtgtaaca cggcccagcc
241 aggctgcacc aacgtctgct atgaccaggc cttccccatc
tcccacatcc gctactgggt
301 gctgcagttc ctcttcgtca gcacacccac cctggtctac
ctgggccatg tcatttacct
361 gtctcggcga gaagagcggc tggcgcagaa ggagggggag
ctgcgggcac tgccggccaa
421 ggacccacag gtggagcggg cgctggccgg catagagctt
cagatggcca agatctcggt
481 ggcagaagat ggtcgcctgc gcattccgcg agcactgatg
ggcacctatg tcgccagtgt
541 gctctgcaag agtgtgctag aggcaggctt cctctatggc
cagtggcgcc tgtacggctg
601 gaccatggag cccgtgtttg tgtgccagcg agcaccctgc
ccctacctcg tggactgctt
661 tgtctctcgc cccacggaga agaccatctt catcatcttc
atgttggtgg ttggactcat
721 ctccctggtg cttaacctgc tggagttggt gcacctgctg
tgtcgctgcc tcagccgggg
781 gatgagggca cggcaaggcc aagacgcacc cccgacccag
ggcacctcct cagaccctta
841 cacggaccag ggtcttcttc tacctccccg tggccagggg
ccctcatccc caccatgccc
901 cacctacaat gggctctcat ccagtgagca gaactgggcc
aacctgacca cagaggagag
961 gctggcgtct tccaggcccc ctctcttcct ggacccaccc
cctcagaatg gccaaaaacc
1021 cccaagtcgt cccagcagct ctgcttctaa gaagcagtat
gtatagaggc ctgtggctta -continued 1081 tgtcacccaa cagaggggtc ctgagaagtc tggctgcctg
ggatgccccc tgcccctcc
1141 tggaaggctc tgcagagatg actgggctgg ggaagcagat
gcttgctggc catggagcct
1201 cattgcaagt tgttcttgaa cacctgaggc cttcctgtgg
cccaccaggc actacggctt
1261 cctctccaga tgtgctttgc ctgagcacag acagtcagca
tggaatgctc ttggccaagg
1321 gtactggggc cctctggcct tttgcagctg atccagagga
acccagagcc aacttacccc
1381 aacctcaccc tatggaacag tcacctgtgc gcaggttgtc
ctcaaaccct ctcctcacag
1441 gaaaaggcgg attgaggctg ctgggtcagc cttgatcgca
cagacagagc ttgtgccgga
1501 tttggccctg tcaaggggac tggtgccttg ttttcatcac
tccttcctag ttctactgtt
1561 caagcttctg aaataaacag gacttgatca caaaaaaaaa
a Human Cx 40, α5 (SEQ ID NO: 15)
LOCUS NM_005266 2574 bp mRNA linear PRI 27-OCT-2004
DEFINITION Homo sapiens gap junction protein, alpha 5, 40kDa (connexin 40) (GJA5), transcript variant A, mRNA.

1 gcaaaaagcg tgggcagttg gagaagaagc agccagagtg
tgaagaagcc cacggaagga
61 aagtccaggg aggaggaaaa gaagcagaag ttttggcatc
tgttccctgg ctgtgccaag
121 atgggcgatt ggagcttcct gggaaatttc ctggaggaag
tacacaagca ctcgaccgtg
181 gtaggcaagg tctggctcac tgtcctcttc atattccgta
tgctcgtgct gggcacagct
241 gctgagtctt cctgggggga tgagcaggct gatttccggt
gtgatacgat tcagcctggc
301 tgccagaatg tctgctacga ccaggctttc cccatctccc
acattcgcta ctgggtgctg
361 cagatcatct tcgtctccac gccctctctg gtgtacatgg
gccacgccat gcacactgtg
421 cgcatgcagg agaagcgcaa gctacgggag gccgagaggg
ccaaagaggt ccggggctct
481 ggctcttacg agtacccggt ggcagagaag gcagaactgt
cctgctggga ggaagggaat -continued 541 ggaaggattg ccctccaggg cactctgctc aacacctatg
tgtgcagcat cctgatccgc
601 accaccatgg aggtgggctt cattgtgggc cagtacttca
tctacggaat cttcctgacc
661 accctgcatg tctgccgcag gagtccctgt ccccacccgg
tcaactgtta cgtatcccgg
721 cccacagaga agaatgtctt cattgtcttt atgctggctg
tggctgcact gtccctcctc
781 cttagcctgg ctgaactcta ccacctgggc tggaagaaga
tcagacagcg atttgtcaaa
841 ccgcggcagc acatggctaa gtgccagctt tctggcccct
ctgtgggcat agtccagagc
901 tgcacaccac cccccgactt taatcagtgc ctggagaatg
gccctggggg aaaattcttc
961 aatcccttca gcaataatat ggcctcccaa caaaacacag
acaacctggt caccgagcaa
1021 gtacgaggtc aggagcagac tcctggggaa ggtttcatcc
aggttcgtta tggccagaag
1081 cctgaggtgc ccaatggagt ctcaccaggt caccgccttc
cccatggcta tcatagtgac
1141 aagcgacgtc ttagtaaggc cagcagcaag gcaaggtcag
atgacctatc agtgtgaccc
1201 tcctttatgg gaggatcagg accaggtggg aacaaaggag
gctcagagaa gaaagacgtg
1261 tcccttctga actgatgctt tctcactgtc atcactgctt
ggctcctttg agccccgggt
1321 ctcaatgacg ttgctcatta attctagaaa ctataaccag
ggctctggga tagtaagaga
1381 ggtgacaacc cacccagact gcagttccct ccccaccctc
tacccagtat acgaagcctt
1441 tcagattact catgaaacag ggtagaggga aagaagggaa
gcatggcaaa agctggcctg
1501 gaagggatag ccagagggat agaatgactc tctctctaca
taccagcagc ataccaaatg
1561 cgttctctaa gttcctacct ccttgacctg atcaccctcc
ctcctccaag gaagagctca
1621 aagttcccag ccaatagaca gcatgaatca aggaacttgc
attatatgtg ctcttgaatc
1681 tgttgtctcc atggaccatt cctcggagta gtggtgagat
ggccttgggt tgcccttggc -continued 1741 ttctcctccc tctactcagc cttaaaaagg gcttcttgga
actttaccag cagcctcagc
1801 tttacaaatg ccttggtatg tacctctggc aaatgcccca
ccttggtgat gttgcaacct
1861 ttccttctgc tagggtgtac acctagcctg tgcaggtgtc
agccctgcta gggagtcact
1921 gtacacacaa actctactgg aattcctgcc aacatctgtc
accctgcagc tcctttacag
1981 ttcaatccaa tgatagaaac catcccttcc ctttctccct
tggctgttca cccagccatt
2041 ccctgaaggc cttaccaaca ggaatatcca agaagctgtt
gtcccctctc gaaccctgac
2101 cagatcatca gccactgagg ccagtggaat ttccccaggc
cttgttaaaa caaagaaagc
2161 attgtacctc tcagattccc cttgtggaaa aaaaaattct
gctgtgaaga tgaaaataaa
2221 aatggagaga aaacactgga aaactatttt cccctcctat
ttacttcctt tgctgactgc
2281 caacttagtg ccaagaggag gtgtgatgac agctatggag
gcccccagat ctctctctcc
2341 tggaggcttt agcaggggca aggaaatagt aggggaatct
ccagctctct tggcagggcc
2401 tttatttaaa gagcgcagag attcctatgt ctccctagtg
cccctaatga gactgccaag
2461 tgggggctgt agaaaagcct tgccttcccc agggattggc
ctggtctctg tattcactgg
2521 atccataatg ggttgctgtt gttttggatg aaggtaaacg
atgcttggaa ttgg Human Cx 45, α7 (SEQ ID NO: 16)
LOCUS NM_005497 1191 bp mRNA linear
PRI 23-DEC-2003
DEFINITION Homo sapiens gap junction protein,
alpha 7, 45kDa (connexin 45) (GJA7),
mRNA.

1 atgagttgga gctttctgac tcgcctgcta gaggagattc
acaaccattc cacatttgtg
61 gggaagatct ggctcactgt tctgattgtc ttccggatcg
tccttacagc tgtaggagga
121 gaatccatct attacgatga gcaaagcaaa tttgtgtgca
acacagaaca gccgggctgt
181 gagaatgtct gttatgatgc gtttgcacct ctctcccatg
tacgcttctg ggtgttccag
241 atcatcctgg tggcaactcc ctctgtgatg tacctgggct
atgctatcca caagattgcc -continued

```
 301 aaaatggagc acggtgaagc agacaagaag gcagctcgga
     gcaagcccta tgcaatgcgc
 361 tggaaacaac accgggctct ggaagaaacg gaggaggaca
     acgaagagga tcctatgatg
 421 tatccagaga tggagttaga aagtgataag gaaaataaag
     agcagagcca acccaaacct
 481 aagcatgatg gccgacgacg gattcgggaa gatgggctca
     tgaaaatcta tgtgctgcag
 541 ttgctggcaa ggaccgtgtt tgaggtgggt tttctgatag
     ggcagtattt tctgtatggc
 601 ttccaagtcc acccgtttta tgtgtgcagc agacttcctt
     gtcctcataa gatagactgc
 661 tttatttcta gacccactga aaagaccatc ttccttctga
     taatgtatgg tgttacaggc
 721 ctttgcctct tgcttaacat ttgggagatg cttcatttag
     ggtttgggac cattcgagac
 781 tcactaaaca gtaaaaggag ggaacttgag gatccgggtg
     cttataatta tcctttcact
 841 tggaatacac catctgctcc ccctggctat aacattgctg
     tcaaaccaga tcaaatccag
 901 tacaccgaac tgtccaatgc taagatcgcc tacaagcaaa
     acaaggccaa cacagcccag
 961 gaacagcagt atggcagcca tgaggagaac ctcccagctg
     acctggaggc tctgcagcgg
1021 gagatcagga tggctcagga acgcttggat ctggcagttc
     aggcctacag tcaccaaaac
1081 aaccctcatg gtccccggga gaagaaggcc aaagtggggt
     ccaaagctgg gtccaacaaa
1141 agcactgcca gtagcaaatc aggggatggg aagaactctg
     tctggattta a
```

Human Cx 50, α8 (SEQ ID NO: 17)

```
LOCUS       NM_005267   1362 bp   mRNA   linear
            PRI 26-OCT-2004
DEFINITION  Homo sapiens gap junction protein,
            alpha 8, 50kDa (connexin 50) (GJA8),
            mRNA.
   1 agcgccaaga gagaaagagc acatatttct ccgtgggaca
     ctccttgtat tggtgggtga
  61 gaaatgggcg actggagttt cctggggaac atcttggagg
     aggtgaatga gcactccacc
 121 gtcatcggca gagtctggct caccgtgctt ttcatcttcc
     ggatcctcat ccttggcacg
 181 gccgcagagt tcgtgtgggg ggatgagcaa tccgacttcg
     tgtgcaacac ccagcagcct
```

-continued

```
 241 ggctgcgaga acgtctgcta cgacgaggcc tttcccatct
     cccacattcg cctctgggtg
 301 ctgcagatca tcttcgtctc caccccgtcc ctgatgtacg
     tggggcacgc ggtgcactac
 361 gtccgcatgg aggagaagcg caaaagccgc gacgaggagc
     tgggccagca ggcggggact
 421 aacggcggcc cggaccaggg cagcgtcaag aagagcagcg
     gcagcaaagg cactaagaag
 481 ttccggctgg aggggaccct gctgaggacc tacatctgcc
     acatcatctt caagaccctc
 541 tttgaagtgg gcttcatcgt gggccactac ttcctgtacg
     ggttccggat cctgcctctg
 601 taccgctgca gccggtggcc ctgccccaat gtggtggact
     gcttcgtgtc ccggcccacg
 661 gagaaaacca tcttcatcct gttcatgttg tctgtggcct
     ctgtgtccct attcctcaac
 721 gtgatggagt tgagccacct gggcctgaag gggatccggt
     ctgccttgaa gaggcctgta
 781 gagcagcccc tgggggagat tcctgagaaa tccctccact
     ccattgctgt ctcctccatc
 841 cagaaagcca agggctatca gcttctagaa gaagagaaaa
     tcgtttccca ctatttcccc
 901 ttgaccgagg ttgggatggt ggagaccagc ccactgcctg
     ccaagccttt caatcagttc
 961 gaggagaaga tcagcacagg acccctgggg gacttgtccc
     ggggctacca agagacactg
1021 ccttcctacg ctcaggtggg ggcacaagaa gtggagggcg
     aggggccgcc tgcagaggag
1081 ggagccgaac ccgaggtggg agagaagaag gaggaagcag
     agaggctgac cacggaggag
1141 caggagaagg tggccgtgcc agagggggag aaagtagaga
     cccccggagt ggataaggag
1201 ggtgaaaaag aagagccgca gtcggagaag gtgtcaaagc
     aagggctgcc agctgagaag
1261 acaccttcac tctgtccaga gctgacaaca gatgatgcca
     gacccctgag caggctaagc
1321 aaagccagca gccgagccag gtcagacgat ctaaccgtat
     ga
```

-continued

Human Cx 36, α9, γ1 (SEQ ID NO: 18)
LOCUS NM_020660 966 bp mRNA linear
PRI 03-SEP-2004
DEFINITION Homo sapiens connexin-36 (CX36), mRNA.

```
  1 atgggggaat ggaccatctt ggagaggctg ctagaagccg
    cggtgcagca gcactccact
 61 atgatcggaa ggatcctgtt gactgtggtg gtgatcttcc
    ggatcctcat tgtggccatt
121 gtgggggaga cggtgtacga tgatgagcag accatgtttg
    tgtgcaacac cctgcagccc
181 ggctgtaacc aggcctgcta tgaccgggcc ttccccatct
    cccacatacg ttactgggtc
241 ttccagatca taatggtgtg tacccccagt ctttgcttca
    tcacctactc tgtgcaccag
301 tccgccaagc agcgagaacg ccgctactct acagtcttcc
    tagccctgga cagagacccc
361 cctgagtcca taggaggtcc tggaggaact gggggtgggg
    gcagtggtgg gggcaaacga
421 gaagataaga agttgcaaaa tgctattgtg aatggggtgc
    tgcagaacac agagaacacc
481 agtaaggaga cagagccaga ttgtttagag gttaaggagc
    tgactccaca cccatcaggt
541 ctacgcactg catcaaaatc caagctcaga aggcaggaag
    gcatctcccg cttctacatt
601 atccaagtgg tgttccgaaa tgccctggaa attgggttcc
    tggttggcca atattttctc
661 tatggcttta gtgtcccagg gttgtatgag tgtaaccgct
    accccctgcat caaggaggtg
721 gaatgttatg tgtcccggcc aactgagaag actgtctttc
    tagtgttcat gtttgctgta
781 agtggcatct gtgttgtgct caacctggct gaactcaacc
    acctgggatg gcgcaagatc
841 aagctggctg tgcgaggggc tcaggccaag agaaagtcaa
    tctatgagat tcgtaacaag
901 gacctgccaa gggtcagtgt tcccaatttt ggcaggactc
    agtccagtga ctctgcctat
961 gtgtga
```

Human Cx 59/58, α10 (SEQ ID NO: 19)
LOCUS NM_030772 1901 bp mRNA linear
PRI 27-OCT-2004
DEFINITION Homo sapiens gap junction protein,
alpha 10, 59kDa (GJA10), mRNA.

```
   1 cagggagttg tggttgcaac actgtactcc agcctgggca
     acagagggag actctgtctc
```

-continued

```
  61 aacaaacaaa caaacaaaga aaaaacccca cagctatcta
     gggaaaaagt aaagcaacca
 121 gcatatagaa gtgacatatt gttatatttt caccataggt
     ttgctttaag aaatagtgct
 181 cccttcagaa tggaagaatt tatctgcctc ttatttgatg
     tggatcagag ctaagatggc
 241 tgactaaata aacatggggg actggaatct ccttggagat
     actctggagg aagttcacat
 301 ccactccacc atgattggaa agatctggct caccatcctg
     ttcatatttc gaatgcttgt
 361 tctgggtgta gcagctgaag atgtctggaa tgatgagcag
     tctggcttca tctgcaatac
 421 agaacaacca ggctgcagaa atgtatgcta cgaccaggcc
     tttcctatct ccctcattag
 481 atactgggtt ctgcaggtga tatttgtgtc ttcaccatcc
     ctggtctaca tgggccatgc
 541 attgtaccga ctgagagttc ttgaggaaga gaggcaaagg
     atgaaagctc agttaagagt
 601 agaactggag gaggtagagt ttgaaatgcc tagggatcgg
     aggagattgg agcaagagct
 661 ttgtcagctg gagaaaagga aactaaataa agctccactc
     agaggaacct tgctttgcac
 721 ttatgtgata cacattttca ctcgctctgt ggttgaagtt
     ggattcatga ttggacagta
 781 ccttttatat ggatttcact tagagccgct atttaagtgc
     catggccacc cgtgtccaaa
 841 tataatcgac tgttttgtct caagaccaac agaaaagaca
     atattcctat tatttatgca
 901 atctatagcc actatttcac ttttcttaaa cattcttgaa
     attttccacc taggttttaa
 961 aaagattaaa agagggcttt ggggaaaata caagttgaag
     aaggaacata atgaattcca
1021 tgcaaacaag gcaaaacaaa atgtagccaa ataccagagc
     acatctgcaa attcactgaa
1081 gcgactccct tctgcccctg attataatct gttagtggaa
     aagcaaacac acactgcagt
1141 gtaccctagt ttaaattcat cttctgtatt ccagccaaat
     cctgacaatc atagtgtaaa
1201 tgatgagaaa tgcattttgg atgaacagga aactgtactt
     tctaatgaga tttccacact
```

-continued 1261 tagtactagt tgtagtcatt ttcaacacat cagttcaaac
aataacaaag acactcataa
1321 aatatttgga aaagaactta atggtaacca gttaatggaa
aaaagagaaa ctgaaggcaa
1381 agacagcaaa aggaactact actctagagg tcaccgttct
attccaggtg ttgctataga
1441 tggagagaac aacatgaggc agtcacccca aacagttttc
tccttgccag ctaactgcga
1501 ttggaaaccg cggtggctta gagctacatg ggttcctct
acagaacatg aaaaccgggg
1561 gtcacctcct aaaggtaacc tcaagggcca gttcagaaag
ggcacagtca gaacccttcc
1621 tccttcacaa ggagattctc aatcacttga cattccaaac
actgctgatt ctttgggagg
1681 gctgtccttt gagccagggt tggtcagaac ctgtaataat
cctgtttgtc ctccaaatca
1741 cgtagtgtcc ctaacgaaca atctcattgg taggcgggtt
cccacagatc ttcagatcta
1801 aacagcggtt ggcttttaga cattatatat attatcagag
aagtagccta gtggtcgtgg
1861 ggcacagaaa aaatagatag gggcagctct aaagaccagc
t Human Cx 46.6/47, α12 (SEQ ID NO: 20)
LOCUS AY285161 1311 bp mRNA linear
PRI 19-MAY-2003
DEFINITION Homo sapiens connexin47 mRNA, complete cds.

1 atgagctgga gcttcctgac gcggctgctg gaggagatcc
acaaccactc caccttcgtg
61 ggcaaggtgt ggctcacggt gctggtggtc ttccgcatcg
tgctgacggc tgtgggcggc
121 gaggccatct actcggacga gcaggccaag ttcacttgca
acacgcggca gccaggctgc
181 gacaacgtct gctatgacgc cttcgcgccc ctgtcgcacg
tgcgcttctg ggtcttccag
241 attgtggtca tctccacgcc ctcggtcatg tacctgggct
acgccgtgca ccgcctggcc
301 cgtgcgtctg agcaggagcg gcgccgcgcc ctccgccgcc
gcccggggcc acgccgcgcg
361 ccccgagcgc acctgccgcc cccgcacgcc ggctggcctg
agcccgccga cctgggcgag
421 gaggagccca tgctgggcct gggcgaggag gaggaggagg
aggagacggg ggcagccgag
481 ggcgccggcg aggaagcgga ggaggcaggc gcggaggagg
cgtgcactaa ggcggtcggc
541 gctgacggca aggcggcagg gaccccgggc ccgaccgggc
aacacgatgg gcggaggcgc
601 atccagcggg agggcctgat gcgcgtgtac gtggcccagc
tggtggccag ggcagctttc
661 gaggtggcct tcctggtggg ccagtacctg ctgtacggct
tcgaggtgcg accgttcttt
721 ccctgcagcc gccagccctg cccgcacgtg gtggactgct
tcgtgtcgcg ccctactgaa
781 aagacggtct tcctgctggt tatgtacgtg gtcagctgcc
tgtgcctgct gctcaacctc
841 tgtgagatgg cccacctggg cttgggcagc gcgcaggacg
cggtgcgcgg ccgccgcggc
901 cccccggcct ccgccccgc ccccgcgccg cggcccccgc
cctgcgcctt ccctgcggcg
961 gccgctggct tggcctgccc gcccgactac agcctggtgg
tgcgggcggc cgagcgcgct
1021 cgggcgcatg accagaacct ggcaaacctg gccctgcagg
cgctgcgcga cggggcagcg
1081 gctggggacc gcgaccggga cagttcgccg tgcgtcggcc
tccctgcggc ctcccggggg
1141 ccccccagag caggcgcccc cgcgtcccgg acgggcagtg
ctacctctgc gggcactgtc
1201 ggggagcagg gccggcccgg cacccacgag cggccaggag
ccaagcccag ggctggctcc
1261 gagaagggca gtgccagcag cagggacggg aagaccaccg
tgtggatctg a Human Cx 32, β1 (SEQ ID NO: 21)
LOCUS BC039198 1588 bp mRNA linear
PRI 07-OCT-2003
DEFINITION Homo sapiens gap junction protein, beta 1, 32kDa (connexin 32, Charcot-Marie-Tooth neuropathy, X-linked), mRNA (cDNA clone MGC: 22506 IMAGE: 4710239), complete cds.

1 agacattctc tgggaaaggg cagcagcagc caggtgtggc
agtgacaggg aggtgtgaat
61 gaggcaggat gaactggaca ggtttgtaca ccttgctcag
tggcgtgaac cggcattcta
121 ctgccattgg ccgagtatgg ctctcggtca tcttcatctt
cagaatcatg gtgctggtgg
181 tggctgcaga gagtgtgtgg ggtgatgaga aatcttcctt
catctgcaac acactccagc -continued

```
241 ctggctgcaa cagcgtttgc tatgaccaat tcttccccat
    ctcccatgtg cggctgtggt
301 ccctgcagct catcctagtt tccaccccag ctctcctcgt
    ggccatgcac gtggctcacc
361 agcaacacat agagaagaaa atgctacggc ttgagggcca
    tggggacccc ctacacctgg
421 aggaggtgaa gaggcacaag gtccacatct cagggacact
    gtggtggacc tatgtcatca
481 gcgtggtgtt ccggctgttg tttgaggccg tcttcatgta
    tgtcttttat ctgctctacc
541 ctggctatgc catggtgcgg ctggtcaagt gcgacgtcta
    cccctgcccc aacacagtgg
601 actgcttcgt gtcccgcccc accgagaaaa ccgtcttcac
    cgtcttcatg ctagctgcct
661 ctggcatctg catcatcctc aatgtggccg aggtggtgta
    cctcatcatc cgggcctgtg
721 cccgccgagc ccagcgccgc tccaatccac cttcccgcaa
    gggctcgggc ttcggccacc
781 gcctctcacc tgaatacaag cagaatgaga tcaacaagct
    gctgagtgag caggatggct
841 ccctgaaaga catactgcgc cgcagccctg gcaccggggc
    tgggctggct gaaaagagcg
901 accgctgctc ggcctgctga tgccacatac caggcaacct
    cccatcccac cccgaccct
961 gccctgggcg agcccctcct tctcccctgc cggtgcacag
    gcctctgcct gctggggatt
1021 actcgatcaa aaccttcctt ccctggctac ttcccttcct
     cccggggcct tcctttgag
1081 gagctggagg ggtggggagc tagaggccac ctatgccagt
     gctcaaggtt actgggagtg
1141 tgggctgccc ttgttgcctg caccettccc tcttccctct
     ccctctctct gggaccactg
1201 ggtacaagag atgggatgct ccgacagcgt ctccaattat
     gaaactaatc ttaaccctgt
1261 gctgtcagat accctgtttc tggagtcaca tcagtgagga
     gggatgtggg taagaggagc
1321 agagggcagg ggtgctgtgg acatgtgggt ggagaaggga
     gggtggccag cactagtaaa
1381 ggaggaatag tgcttgctgg ccacaaggaa aaggaggagg
     tgtctggggt gagggagtta
```

-continued

```
1441 gggagagaga agcaggcaga taagttggag caggggttgg
     tcaaggccac ctctgcctct
1501 agtccccaag gcctctctct gcctgaaatg ttacacatta
     aacaggattt tacagcaaaa
1561 aaaaaaaaaa aaaaaaaaaa aaaaaaaa
```

Human Cx 26, β2 (SEQ ID NO: 22)

```
LOCUS       NM_004004   2263 bp   mRNA   linear
            PRI 28-OCT-2004
DEFINITION  Homo sapiens gap junction protein,
            beta 2, 26kDa (connexin 26) (GJB2),
            mRNA.
  1 cggagcccct cggcggcgcc cggcccagga cccgcctagg
    agcgcaggag ccccagcgca
 61 gagaccccaa cgccgagacc cccgccccgg ccccgccgcg
    cttcctcccg acgcagagca
121 aaccgcccag agtagaagat ggattggggc acgctgcaga
    cgatcctggg gggtgtgaac
181 aaacactcca ccagcattgg aaagatctgg ctcaccgtcc
    tcttcatttt tcgcattatg
241 atcctcgttg tggctgcaaa ggaggtgtgg ggagatgagc
    aggccgactt tgtctgcaac
301 accctgcagc caggctgcaa gaacgtgtgc tacgatcact
    acttccccat ctcccacatc
361 cggctatggg ccctgcagct gatcttcgtg tccacgccag
    cgctcctagt ggccatgcac
421 gtggcctacc ggagacatga gaagaagagg aagttcatca
    agggggagat aaagagtgaa
481 tttaaggaca tcgaggagat caaaacccag aaggtccgca
    tcgaaggctc cctgtggtgg
541 acctacacaa gcagcatctt cttccgggtc atcttcgaag
    ccgccttcat gtacgtcttc
601 tatgtcatgt acgacggctt ctccatgcag cggctggtga
    agtgcaacgc ctggccttgt
661 cccaacactg tggactgctt tgtgtcccgg cccacggaga
    agactgtctt cacagtgttc
721 atgattgcag tgtctggaat ttgcatcctg ctgaatgtca
    ctgaattgtg ttatttgcta
781 attagatatt gttctgggaa gtcaaaaaag ccagtttaac
    gcattgccca gttgttagat
841 taagaaatag acagcatgag agggatgagg caacccgtgc
    tcagctgtca aggctcagtc
901 gccagcattt cccaacacaa agattctgac cttaaatgca
    accatttgaa acccctgtag
```

```
 961 gcctcaggtg aaactccaga tgccacaatg gagctctgct
     cccctaaagc ctcaaaacaa
1021 aggcctaatt ctatgcctgt cttaattttc tttcacttaa
     gttagttcca ctgagacccc
1081 aggctgttag ggttattgg tgtaaggtac tttcatattt
     taaacagagg atatcggcat
1141 ttgtttcttt ctctgaggac aagagaaaaa agccaggttc
     cacagaggac acagagaagg
1201 tttgggtgtc ctcctggggt tctttttgcc aactttcccc
     acgttaaagg tgaacattgg
1261 ttctttcatt tgctttggaa gttttaatct ctaacagtgg
     acaaagttac cagtgcctta
1321 aactctgtta cactttttgg aagtgaaaac tttgtagtat
     gataggttat tttgatgtaa
1381 agatgttctg gataccatta tatgttcccc ctgtttcaga
     ggctcagatt gtaatatgta
1441 aatggtatgt cattcgctac tatgatttaa tttgaaatat
     ggtcttttgg ttatgaatac
1501 tttgcagcac agctgagagg ctgtctgttg tattcattgt
     ggtcatagca cctaacaaca
1561 ttgtagcctc aatcgagtga gacagactag aagttcctag
     tgatggctta tgatagcaaa
1621 tggcctcatg tcaaatattt agatgtaatt ttgtgtaaga
     aatacagact ggatgtacca
1681 ccaactacta cctgtaatga caggcctgtc caacacatct
     cccttttcca tgactgtggt
1741 agccagcatc ggaaagaacg ctgatttaaa gaggtcgctt
     gggaatttta ttgacacagt
1801 accatttaat ggggaggaca aaatggggca ggggagggag
     aagtttctgt cgttaaaaac
1861 agatttggaa agactggact ctaaattctg ttgattaaag
     atgagctttg tctacttcaa
1921 aagtttgttt gcttacccct tcagcctcca atttttaag
     tgaaaatata actaataaca
1981 tgtgaaaaga atagaagcta aggtttagat aaatattgag
     cagatctata ggaagattga
2041 acctgaatat tgccattatg cttgacatgg tttccaaaaa
     atggtactcc acatacttca
```

```
2101 gtgagggtaa gtattttcct gttgtcaaga atagcattgt
     aaaagcattt tgtaataata
2161 aagaatagct ttaatgatat gcttgtaact aaaataattt
     tgtaatgtat caaatacatt
2221 taaaacatta aaatataatc tctataataa aaaaaaaaaa
     aaa
```

Human Cx 31, β3 (SEQ ID NO: 23)

```
LOCUS      NM_024009   2220 bp   mRNA   linear
           PRI 28-OCT-2004
DEFINITION Homo sapiens gap junction protein,
           beta 3, 31kDa (connexin 31) (GJB3),
           transcript variant 1, mRNA.
   1 gaacttcttt cctggcacag gactcactgt gccccttccc
     gctgtgggta caaggtctgc
  61 cccccacccc agctctccaa agcccaccgg cctccctgga
     ggccgaggtc gacggcccgt
 121 cgcaccggga gggggggctc ccaggggtgc cccacgcacg
     gtcaaggtcc cgcgccaagc
 181 ggggaccggg ctgggccgga agcgggcacg gtactcgcgg
     caaactagcg tgggcgagtc
 241 ctgattgcag tcggacctgc cgccgcggca cttaacagtt
     tgcagagtgc ttcccgcccc
 301 tgatctcatt ggagccttcg gacagcccag cccatggcca
     ccgatgcccc catttcacgc
 361 ctgaggaagc ggaggctcag acgggccacc agcccctccg
     gaggctggcc cgggagcgcc
 421 tggcagcgtc gggtctagga gccggctccc tcctgctccc
     tcctccgcgc cgcccggggt
 481 gtgcccgccg tctgtgtgca ccactgctga gcccagctcc
     ggcgccctcg cctctgctgt
 541 gggccccggg gacgcggggt caggccaccg cgttggccag
     gccgctgcag gtaggcacgg
 601 cccccaccag gcgccatgga ctggaagaca ctccaggccc
     tactgagcgg tgtgaacaag
 661 tactccacag cgttcgggcg catctggctg tccgtggtgt
     tcgtcttccg ggtgctggta
 721 tacgtggtgg ctgcagagcg cgtgtggggg gatgagcaga
     aggactttga ctgcaacacc
 781 aagcagcccg gctgcaccaa cgtctgctac gacaactact
     tccccatctc caacatccgc
 841 ctctgggccc tgcagctcat cttcgtcaca tgcccctcgc
     tgctggtcat cctgcacgtg
 901 gcctaccgtg aggagcggga gcgccggcac cgccagaaac
     acggggacca gtgcgccaag
```

-continued

```
 961 ctgtacgaca acgcaggcaa gaagcacgga ggcctgtggt
     ggacctacct gttcagcctc
1021 atcttcaagc tcatcattga gttcctcttc ctctacctgc
     tgcacactct ctggcatggc
1081 ttcaatatgc cgcgcctggt gcagtgtgcc aacgtggccc
     cctgccccaa catcgtggac
1141 tgctacattg cccgacctac cgagaagaaa atcttcacct
     acttcatggt gggcgcctcc
1201 gccgtctgca tcgtactcac catctgtgag ctctgctacc
     tcatctgcca cagggtcctg
1261 cgaggcctgc acaaggacaa gcctcgaggg ggttgcagcc
     cctcgtcctc cgccagccga
1321 gcttccacct gccgctgcca ccacaagctg gtggaggctg
     gggaggtgga tccagaccca
1381 ggcaataaca agctgcaggc ttcagcaccc aacctgaccc
     ccatctgacc acagggcagg
1441 ggtggggcaa catgcgggct gccaatggga catgcagggc
     ggtgtggcag gtggagaggt
1501 cctacagggg ctgagtgacc ccactctgag ttcactaagt
     tatgcaactt tcgttttggc
1561 agatattttt tgacactggg aactgggctg tctagccggg
     tataggtaac ccacaggccc
1621 agtgccagcc ctcaaaggac atagactttg aaacaagcga
     attaactatc tacgctgcct
1681 gcaaggggcc acttagggca ctgctagcag ggcttcaacc
     aggaagggat caacccagga
1741 agggatgatc aggagaggct tccctgagga cataatgtgt
     aagagaggtg agaagtgctc
1801 ccaagcagac acaacagcag cacagaggtc tggaggccac
     acaaaaaagtg atgctcgccc
1861 tgggctagcc tcagcagacc taaggcatct ctactccetc
     cagaggagcc gcccagattc
1921 ctgcagtgga gaggaggtct tccagcagca gcaggtctgg
     agggctgaga atgaacctga
1981 ctagaggttc tggagatacc cagaggtccc ccaggtcatc
     acttggctca gtggaagccc
2041 tctttcccca aatectactc cctcagcctc aggcagtggt
     gctcccatct tectecccac
2101 aactgtgctc aggctggtgc cagcctttca gaccctgetc
     ccagggactt gggtggatgc
2161 gctgatagaa catcctcaag acagtttcct tgaaatcaat
     aaatactgtg ttttataaaa
```

Human Cx30.3, β4 (SEQ ID NO: 24)

```
LOCUS       NM_153212   1243 bp   mRNA   linear
            PRI 27-OCT-2004
DEFINITION  Homo sapiens gap junction protein,
            beta 4 (connexin 30.3) (GJB4), mRNA.
   1 caaggctccc aaggcctgag tgggcaggta gcacccaggt
     atagaccttc cacgtgcagc
  61 acccaggaca cagccagcat gaactgggca tttctgcagg
     gcctgctgag tggcgtgaac
 121 aagtactcca cagtgctgag ccgcatctgg ctgtctgtgg
     tgttcatctt tcgtgtgctg
 181 gtgtacgtgg tggcagcgga ggaggtgtgg gacgatgagc
     agaaggactt tgtctgcaac
 241 accaagcagc ccggctgccc caacgtctgc tatgacgagt
     tcttccccgt gtcccacgtg
 301 cgcctctggg ccctacagct catcctggtc acgtgcccct
     cactgctcgt ggtcatgcac
 361 gtggcctacc gcgaggaacg cgagcgcaag caccacctga
     aacacgggcc caatgccccg
 421 tccctgtacg acaacctgag caagaagcgg ggcggactgt
     ggtggacgta cttgctgagc
 481 ctcatcttca aggccgccgt ggatgctggc ttcctctata
     tcttccaccg cctctacaag
 541 gattatgaca tgccccgcgt ggtggcctgc tccgtggagc
     cttgccccca cactgtggac
 601 tgttacatct cccggcccac ggagaagaag gtcttcacct
     acttcatggt gaccacagct
 661 gccatctgca tcctgctcaa cctcagtgaa gtcttctacc
     tggtgggcaa gaggtgcatg
 721 gagatcttcg gccccaggca ccggcggcct cggtgccggg
     aatgcctacc cgatacgtgc
 781 ccaccatatg tcctctccca gggagggcac cctgaggatg
     ggaactctgt cctaatgaag
 841 gctgggtcgg ccccagtgga tgcaggtggg tatccataac
     ctgcgagatc agcagataag
 901 atcaacaggt cccccccaca tgaggccacc caggaaaaaa
     ggcaggggca gtggcatcct
 961 tgccgtagca gggtggtgag gagggtggct gtgggggctc
     aggaagctcg cccaggggcc
1021 aatgtgggag gttgggggta gtttggtccc tgggtcctga
     gcctcagggg agggaggttg
```

-continued

```
1081 atagctactg gggattttgt atatggcaac agtatatgtc
     aaacctctta ttaaatatga
1141 ttttcccagt aaaaaaaaaa aaaaaaaaaa aaaaaaaaaa
     aaaaaaaaaa aaaaaaaaaa
1201 aaaaaaaaaa aaaaaaaaaa aaaaaaaaaa aaaaaaaaaa
     aaa
```

Human Cx31.1, 135 (SEQ ID NO: 25)

```
LOCUS       NM_005268   1299 bp   mRNA   linear
            PRI 23-AUG-2004
DEFINITION  Homo sapiens gap junction protein,
            beta 5 (connexin 31.1) (GJB5), mRNA.
   1 atgaaattca agctgcttgc tgagtcctat tgccggctgc
     tgggagccag gagagccctg
  61 aggagtagtc actcagtagc agctgacgcg tgggtccacc
     atgaactgga gtatctttga
 121 gggactcctg agtggggtca acaagtactc cacagccttt
     gggcgcatct ggctgtctct
 181 ggtcttcatc ttccgcgtgc tggtgtacct ggtgacggcc
     gagcgtgtgt ggagtgatga
 241 ccacaaggac ttcgactgca atactcgcca gcccggctgc
     tccaacgtct gctttgatga
 301 gttcttccct gtgtcccatg tgcgcctctg ggccctgcag
     cttatcctgg tgacatgccc
 361 ctcactgctc gtggtcatgc acgtggccta ccgggaggtt
     caggagaaga ggcaccgaga
 421 agcccatggg gagaacagtg ggcgcctcta cctgaacccc
     ggcaagaagc ggggtgggct
 481 ctggtggaca tatgtctgca gcctagtgtt caaggcgagc
     gtggacatcg cctttctcta
 541 tgtgttccac tcattctacc ccaaatatat cctccctcct
     gtggtcaagt gccacgcaga
 601 tccatgtccc aatatagtgg actgcttcat ctccaagccc
     tcagagaaga acattttcac
 661 cctcttcatg gtggccacag ctgccatctg catcctgctc
     aacctcgtgg agctcatcta
 721 cctggtgagc aagagatgcc acgagtgcct ggcagcaagg
     aaagctcaag ccatgtgcac
 781 aggtcatcac ccccacggta ccacctcttc ctgcaaacaa
     gacgacctcc tttcgggtga
 841 cctcatcttt ctgggctcag acagtcatcc tcctctctta
     ccagaccgcc cccgagacca
 901 tgtgaagaaa accatcttgt gaggggctgc ctggactggt
     ctggcaggtt gggcctggat
```

-continued

```
 961 ggggaggctc tagcatctct cataggtgca acctgagagt
     gggggagcta agccatgagg
1021 taggggcagg caagagagag gattcagacg ctctgggagc
     cagttcctag tcctcaactc
1081 cagccacctg ccccagctcg acggcactgg gccagttccc
     cctctgctct gcagctcggt
1141 ttccttttct agaatggaaa tagtgagggc caatgcccag
     ggttggaggg aggagggcgt
1201 tcatagaaga acacacatgc gggcaccttc atcgtgtgtg
     gcccactgtc agaacttaat
1261 aaaagtcaac tcatttgctg gaaaaaaaaa aaaaaaaaa
```

Human Cx 30, β6 (SEQ ID NO: 26)

```
LOCUS       BC038934   1805 bp   mRNA   linear
            PRI 30-JUN-2004
DEFINITION  Homo sapiens gap junction protein,
            beta 6 (connexin 30), mRNA (cDNA
            clone MGC: 45195 IMAGE: 5196769),
            complete cds.
   1 ctgggaagac gctggtcagt tcacctgccc cactggttgt
     tttttaaaca aattctgata
  61 caggcgacat cctcactgac cgagcaaaga ttgacattcg
     tatcatcact gtgcaccatt
 121 ggcttctagg cactccagtg ggtaggagaa aggaggtctg
     aaaccctcgc agagggatct
 181 tgccctcatt ctttgggtct gaaacactgg cagtcgttgg
     aaacaggact cagggataaa
 241 ccagcgcaat ggattggggg acgctgcaca ctttcatcgg
     gggtgtcaac aaacactcca
 301 ccagcatcgg gaaggtgtgg atcacagtca tctttatttt
     ccgagtcatg atcctcgtgg
 361 tggctgccca ggaagtgtgg ggtgacgagc aagaggactt
     cgtctgcaac acactgcaac
 421 cgggatgcaa aaatgtgtgc tatgaccact ttttcccggt
     gtcccacatc cggctgtggg
 481 ccctccagct gatcttcgtc tccaccccag cgctgctggt
     ggccatgcat gtggcctact
 541 acaggcacga aaccactcgc aagttcaggc gaggagagaa
     gaggaatgat ttcaaagaca
 601 tagaggacat taaaaagcag aaggttcgga tagaggggtc
     gctgtggtgg acgtacacca
 661 gcagcatctt tttccgaatc atctttgaag cagcctttat
     gtatgtgttt tacttccttt
 721 acaatgggta ccacctgccc tgggtgttga aatgtgggat
     tgacccctgc cccaaccttg
```

-continued

```
781 ttgactgctt tatttctagg ccaacagaga agaccgtgtt
    taccattttt atgatttctg
841 cgtctgtgat ttgcatgctg cttaacgtgg cagagttgtg
    ctacctgctg ctgaaagtgt
901 gttttaggag atcaaagaga gcacagacgc aaaaaaatca
    ccccaatcat gccctaaagg
961 agagtaagca gaatgaaatg aatgagctga tttcagatag
    tggtcaaaat gcaatcacag
1021 gtttcccaag ctaaacattt caaggtaaaa tgtagctgcg
    tcataaggag acttctgtct
1081 tctccagaag gcaataccaa cctgaaagtt ccttctgtag
    cctgaagagt ttgtaaatga
1141 ctttcataat aaatagacac ttgagttaac tttttgtagg
    atacttgctc cattcataca
1201 caacgtaatc aaatatgtgg tccatctctg aaaacaagag
    actgcttgac aaaggagcat
1261 tgcagtcact ttgacaggtt ccttttaagt ggactctctg
    acaaagtggg tactttctga
1321 aaatttatat aactgttgtt gataaggaac atttatccag
    gaattgatac ttttattagg
1381 aaaagatatt tttataggct tggatgtttt tagttctgac
    tttgaattta tataaagtat
1441 ttttataatg actggtcttc cttacctgga aaaacatgcg
    atgttagttt tagaattaca
1501 ccacaagtat ctaaatttgg aacttacaaa gggtctatct
    tgtaaatatt gttttgcatt
1561 gtctgttggc aaatttgtga actgtcatga tacgcttaag
    gtggaaagtg ttcattgcac
1621 aatatatttt tactgctttc tgaatgtaga cggaacagtg
    tggaagcaga aggctttttt
1681 aactcatccg tttgccaatc attgcaaaca actgaaatgt
    ggatgtgatt gcctcaataa
1741 agctcgtccc cattgcttaa gccttcaaaa aaaaaaaaaa
    aaaaaaaaaa aaaaaaaaaa
1801 aaaaa
```

Human Cx31.9, c1 (SEQ ID NO: 27)

```
LOCUS       NM_152219   2094 bp   mRNA   linear
            PRI 23-AUG-2004
DEFINITION  Homo sapiens gap junction protein,
            chi 1, 31.9kDa (connexin 31.9) (GJC1),
            mRNA.
   1 aaatgaaaga gggagcagga ggcgccggtc ccagccacct
     cccaaggtcc ctggctcagc
```

-continued

```
  61 tctgacaccc cagtcccggc cccagggtga gtggggttgg
     gtggcggttt aggggcacca
 121 ggggcgtgtg ggacctgtg taagtgtggg gtggggagga
     tctcaggaga tgtggaggct
 181 ggaggcacag gaggccaggg aggagggaga agcctggtgc
     cgcactccca ccacgctggg
 241 gtaggagggc agggacacct ccgacaaagg accctgtgag
     agttatgaaa gcggagttgc
 301 ctctgtacca gccccccacc ctgagaggag ttcactgcag
     taaaaatggt gagagaaatg
 361 gtgggccaag aaaggagtgg tctcgctgcc tctgccactc
     ccactcctcc catgggcacc
 421 aaattgggtc tagcgtctcg ggttcgaggc tccactcttc
     ccacagcatc cttgacagct
 481 aagggcaccg ctgggtttcc gcttccgaaa ccaggcaagt
     caggggctgg tccagctgat
 541 ctccaaggtc cttcctaaga atctgggatc tggaggatcc
     cagggtcgaa cggagacggc
 601 tcagggggtg cggctaaaat gcaaatgggg gatcctcccc
     agcacccatc ggtcccaaag
 661 agaaggtaac ccatagctga gcgtcgcctg ctcccctcgg
     gccctcccgt ggccctccgt
 721 ttcatactgg tctcatcgct aaacccgggc ctctcctacc
     tcacgactca ccctgaagtc
 781 agagaaggtc caacggaccc caccccgata ggcttggaag
     gggcaggggt ccctgacttg
 841 ccccatcccc tgactccccg ccccgcgtcc ccagcgccat
     gggggagtgg gcgttcctgg
 901 gctcgctgct ggacgccgtg cagctgcagt cgccgctcgt
     gggccgcctc tggctggtgg
 961 tcatgctgat cttccgcatc ctggtgctgg ccacggtggg
     cggcgccgtg ttcgaggacg
1021 agcaagagga gttcgtgtgc aacacgctgc agccgggctg
     tcgccagacc tgctacgacc
1081 gcgccttccc ggtctcccac taccgcttct ggctcttcca
     catcctgctg ctctcggcgc
1141 ccccggtgct gttcgtcgtc tactccatgc accgggcagg
     caaggaggcg ggcggcgctg
1201 aggcggcggc gcagtgcgcc cccggactgc ccgaggccca
     gtgcgcgccg tgcgccctgc
```

-continued

```
1261 gcgcccgccg cgcgcgccgc tgctacctgc tgagcgtggc
     gctgcgcctg ctggccgagc
1321 tgaccttcct gggcggccag gcgctgctct acggettccg
     cgtggccccg cacttcgcgt
1381 gcgccggtcc gccctgcccg cacacggtcg actgcttcgt
     gagccggccc accgagaaga
1441 ccgtcttcgt gctcttctat ttcgcggtgg ggctgctgtc
     ggcgctgctc agcgtagccg
1501 agctgggcca cctgctctgg aagggccgcc cgcgcgccgg
     ggagcgtgac aaccgctgca
1561 accgtgcaca cgaagaggcg cagaagctgc tcccgccgcc
     gccgccgcca cctattgttg
1621 tcacttggga agaaaacaga caccttcaag gagagggctc
     ccctggtagc ccccacccca
1681 agacagagct ggatgcccct cgcttccgta gggaaagcac
     ttctcctgca ggatggcatt
1741 gctctctccc cttccatggc acgtagtatg tgctcagtaa
     atatgtgttg gatgagaaac
1801 tgaaggtgtc cccaggccta caccactgcc atgcccgaac
     actatccatg ctatggtggg
1861 caccatctct ctgatgacag ttctgtgtcc acaacccaga
     cccctccaca caaacccaga
1921 tggggctgtg ccgctgtttt ccagatgtat tcattcaaca
     aatatttgta gggtacctac
1981 tgtgtgtcag aagatgttca agatcagcat catccgatgg
     aaatagcata tgagccatgt
2041 atgtagtttc aagtttttca ttagccgcat taaaaaagta
     aaaggaaaca aatg
```

Human Cx 29/31.3, e1 (SEQ ID NO: 28)
LOCUS AF503615 840 bp mRNA linear
PRI 07-AUG-2002
DEFINITION Homo sapiens connexin 31.3 mRNA, complete cds.

```
  1 atgtgtggca ggttcctgcg gcggctgctg gcggaggaga
    gccggcgctc cacccccgtg
 61 gggcgcctct tgcttcccgt gctcctggga ttccgccttg
    tgctgctggc tgccagtggg
121 cctggagtct atggtgatga gcagagtgaa ttcgtgtgtc
    acacccagca gccgggctgc
181 aaggctgcct gcttcgatgc cttccacccc ctctccccgc
    tgcgtttctg ggtcttccag
241 gtcatcttgg tggctgtacc cagcgccctc tatatgggtt
    tcactctgta tcacgtgatc
```

-continued

```
301 tggcactggg aattatcagg aaaggggaag gaggaggaga
    ccctgatcca gggacgggag
361 ggcaacacag atgtcccagg ggctggaagc ctcaggctgc
    tctgggctta tgtggctcag
421 ctgggggctc ggcttgtcct ggagggggca gccctggggt
    tgcagtacca cctgtatggg
481 ttccagatgc ccagctcctt tgcatgtcgc cgagaacctt
    gccttggtag tataacctgc
541 aatctgtccc gcccctctga gaagaccatt ttcctaaaga
    ccatgtttgg agtcagcggt
601 ttctgtctct tgtttacttt tttggagctt gtgcttctgg
    gtttggggag atggtggagg
661 acctggaagc acaaatcttc ctcttctaaa tacttcctaa
    cttcagagag caccagaaga
721 cacaagaaag caaccgatag cctcccagtg gtggaaacca
    aagagcaatt tcaagaagca
781 gttccaggaa gaagcttagc ccaggaaaaa caaagaccag
    ttggacccag agatgcctga
```

Human Cx 25 (SEQ ID NO: 29)
LOCUS HSA414563 672 bp DNA linear
PRI 30-NOV-2001
DEFINITION Homo sapiens CX25 gene for connexin25.

```
  1 atgagttgga tgttcctcag agatctcctg agtggagtaa
    ataaatactc cactgggact
 61 ggatggattt ggctggctgt cgtgtttgtc ttccgtttgc
    tggtctacat ggtggcagca
121 gagcacatgt ggaaagatga gcagaaagag tttgagtgca
    acagtagaca gcccggttgc
181 aaaaatgtgt gttttgatga cttcttcccc atttcccaag
    tcagactttg ggccttacaa
241 ctgataatgg tctccacacc ttcacttctg gtggttttac
    atgtagccta tcatgagggt
301 agagagaaaa ggcacagaaa gaaactctat gtcagcccag
    gtacaatgga tgggggccta
361 tggtacgctt atcttatcag cctcattgtt aaaactggtt
    ttgaaattgg cttccttgtt
421 ttattttata agctatatga tggctttagt gttccctacc
    ttataaagtg tgatttgaag
481 ccttgtccca acactgtgga ctgcttcatc tccaaaccca
    ctgagaagac gatcttcatc
541 ctcttcttgg tcatcacctc atgcttgtgt attgtgttga
    atttcattga actgagtttt
```

-continued 601 ttggttctca agtgctttat taagtgctgt ctccaaaaat atttaaaaaa acctcaagtc 661 ctcagtgtgt ga Human Cx40.1 (SEQ ID NO: 30)
LOCUS HSA414564 1113 bp mRNA linear PRI 30-NOV-2001
DEFINITION Homo sapiens mRNA for connexin40.1 (CX40.1 gene).

1 atggaaggcg tggacttgct agggtttctc atcatcacat taaactgcaa cgtgaccatg 61 gtaggaaagc tctggttcgt cctcacgatg ctgctgcgga tgctggtgat tgtcttggcg 121 gggcgacccg tctaccagga cgagcaggag aggtttgtct gcaacacgct gcagccggga 181 tgcgccaatg tttgctacga cgtcttctcc cccgtgtctc acctgcggtt ctggctgatc 241 cagggcgtgt gcgtcctcct cccctccgcc gtcttcagcg tctatgtcct gcaccgagga 301 gccacgctcg ccgcgctggg cccccgccgc tgccccgacc cccgggagcc ggcctccggg 361 cagagacgct gcccgcggcc attcggggag cgcggcggcc tccaggtgcc cgacttttcg 421 gccggctaca tcatccacct cctcctccgg accctgctgg aggcagcctt cggggccttg 481 cactactttc tctttggatt cctggccccg aagaagttcc cttgcacgcg ccctccgtgc 541 acgggcgtgg tggactgcta cgtgtcgcgg cccacagaga agtccctgct gatgctgttc 601 ctctgggcgg tcagcgcgct gtcttttctg ctgggcctcg ccgacctggt ctgcagcctg 661 cggcggcgga tgcgcaggag gccgggaccc cccacaagcc cctccatccg gaagcagagc 721 ggagcctcag gccacgcgga gggacgccgg actgacgagg agggtgggcg ggaggaagag 781 ggggcaccgg cgcccccggg tgcacgcgcc ggaggggagg gggctggcag ccccaggcgt 841 acatccaggg tgtcagggca cacgaagatt ccggatgagg atgagagtga ggtgacatcc 901 tccgccagcg aaaagctggg cagacagccc cggggcaggc cccaccgaga ggccgcccag -continued 961 gaccccaggg gctcaggatc cgaggagcag ccctcagcag cccccagccg cctggccgcg 1021 ccccccttcct gcagcagcct gcagcccccct gacccgcctg ccagctccag tggtgctccc 1081 cacctgagag ccaggaagtc tgagtgggtg tga Human Cx 62 (SEQ ID NO: 31)
LOCUS HSA414565 1632 bp DNA linear PRI 30-NOV-2001
DEFINITION Homo sapiens CX62 gene for connexin62.

1 atgggggact ggaacttatt gggtggcatc ctagaggaag ttcactccca ctcaaccata 61 gtggggaaaa tctggctgac catcctcttc atcttccgaa tgctggtact tcgtgtggct 121 gctgaggatg tctgggatga tgaacagtca gcatttgcct gcaacacccg gcagccaggt 181 tgcaacaata tctgttatga tgatgcattc cctatctctt tgatcaggtt ctgggtttta 241 cagatcatct ttgtgtcttc tccttctttg gtctatatgg gccatgcact ttataggctc 301 agggcctttg agaaagacag gcagaggaaa aagtcacacc ttagagccca gatggagaat 361 ccagatcttg acttggagga gcagcaaaga atagataggg aactgaggag gttagaggag 421 cagaagagga tccataaagt ccctctgaaa ggatgtctgc tgcgtactta tgtcttacac 481 atcttgacca gatctgtgct ggaagtagga ttcatgatag gccaatatat tctctatggg 541 tttcaaatgc acccccttta caaatgcact caacctcctt gccccaatgc ggtggattgc 601 tttgtatcca ggcccactga gaagacaatt ttcatgcttt ttatgcacag cattgcagcc 661 atttccttgt tactcaatat actggaaata tttcatctag gcatcagaaa aattatgagg 721 acactttata agaaatccag cagtgagggc attgaggatg aaacaggccc tccattccat 781 ttgaagaaat attctgtggc ccagcagtgt atgatttgct cttcattgcc tgaaagaatc 841 tctccacttc aagctaacaa tcaacagcaa gtcattcgag ttaatgtgcc aaagtctaaa 901 accatgtggc aaatcccaca gccaaggcaa cttgaagtag acccttccaa tgggaaaaag 961 gactggtctg agaaggatca gcatagcgga cagctccatg ttcacagccc gtgtccctgg -continued

```
1021 gctggcagtg ctggaaatca gcacctggga cagcaatcag
     accattcctc atttggcctg
1081 cagaatacaa tgtctcagtc ctggctaggt acaactacgg
     ctcctagaaa ctgtccatcc
1141 tttgcagtag gaacctggga gcagtcccag gacccagaac
     cctcaggtga gcctctcaca
1201 gatcttcata gtcactgcag agacagtgaa ggcagcatga
     gagagagtgg ggtctggata
1261 gacagatctc gcccaggcag tcgcaaggcc agctttctgt
     ccagattgtt gtctgaaaag
1321 cgacatctgc acagtgactc aggaagctct ggttctcgga
     atagctcctg cttggatttt
1381 cctcactggg aaaacagccc ctcacctctg ccttcagtca
     ctgggcacag aacatcaatg
1441 gtaagacagg cagccctacc gatcatggaa ctatcacaag
     agctgttcca ttctggatgc
1501 tttcttttc ctttctttct tcctggggtg tgtatgtatg
     tttgtgttga cagagaggca
1561 gatggagggg gagattattt atggagagat aaaattattc
     attcgataca ttcagttaaa
1621 ttcaattcat aa
```

Various aspects of the invention will now be described with reference to the following experimental section which will be understood to be provided by way of illustration only and not to constitute a limitation on the scope of the invention.

The following Examples are offered by way of illustration and not by way of limitation.

Example 1: In Vivo Analysis

Materials and Methods

Laser Treatment

Female Wistar rats (d32-34) were raised under conditions consistent with the ARVO Resolution on the Use of Animals in Research. Animals were anaesthetised by administrating a 1:1 mixture of Hypnorm™ (10 mg/ml, Jansen Pharmaceutica, Belgium) and Hypnovel® (5 mg/ml, Roche products Ltd, New Zealand) at a dose of 0.083 ml/100 g body weight in the peritoneum of the animal.

Excimer laser treatment was performed through the intact epithelium using a Technolas 217 Z excimer laser (Bausch & Lomb Surgical, USA). The eye was centered at the middle of the pupil and ablation was performed with the following parameters: treatment area was of 2.5 mm diameter and of 70 μm depth. This resulted in the removal of a small thickness of the anterior stroma and of the whole epithelium. Excimer laser treatment was preferentially used to produce reproducible lesions and investigate the effects of connexin43 AS ODNs on corneal remodeling and engineering after trauma.

Following surgery, all animals were placed in individual cages and closely monitored for any discomfort. Post-surgical in vivo evaluation was achieved using a slit lamp biomicroscope and/or a slit scanning in vivo confocal microscope.

Slit Scanning In Vivo Confocal Microscopy

Prior to, and following corneal laser treatment, each animal was observed clinically using a Confoscan 2 (Fortune Technologies America, USA) slit scanning in vivo confocal microscope. The Confoscan 2 is a variant of slit scanning technology with the distinct advantage of direct digitization of the images at the time of acquisition. Animals were anaesthetized and each of them was placed onto a specially designed platform that was adjusted at the level of the in vivo confocal microscope objective lens in front of the acquisition head.

The slit scanning in vivo confocal microscope allows optical dissection of the living cornea at different levels through the whole corneal thickness. The examination starts from the endothelium and the number of the antero-posterior sections depends upon the customized settings. The slit scanning technology utilizes an objective lens that moves back and forward along the axis perpendicular to the examined area. In brief, the hardware consists of a halogen lamp (100 W/12V), two slits, two tube lenses, a front objective lens, and a highly sensitive digital (CCD) camera. Prior to scanning, a drop of Viscotears (CIBAVision Ophthalmics) is placed on the tip of the objective lens as an immersion substance. During scanning, the eye of the animal is held wide open and orientated so that the corneal plane is always perpendicular to the optical axis of the magnification lens (40×, N.A 0.75). The image acquisition time is approximately 14 seconds. The gel, not the objective lens contacts the eye at all times. For the rat cornea, up to 250 sequential digital images were obtained per examination, and were directly saved to a hard disk drive. Acquisition parameters were adjusted during the preliminary experiments and were kept constant for all subsequent experiments. They were as follows: the light intensity was decreased to half the intensity generally used for human patients, four passes (one pass is considered as being a full back and forward movement) were used, and a 400 μm working distance was selected. For the rat cornea, centration is facilitated by clear visualization of the pupil, which provides very good topographical repeatability.

In Vivo Confocal Images

All images acquired with the slit scanning in vivo confocal microscope were stored onto the hard disc drive and subsequently analyzed by NAVIS proprietary software (Confoscan 2, Nidek Co Ltd).

Stromal dynamics were evaluated following stereological principles. Cell counts were recorded at the anterior and posterior stromal positions. The main stereological component was provided by the in vivo confocal microscope itself as it functions as an optical dissector (a probe that samples with equal probability particles in space). Indeed, the in vivo confocal microscope provides thin optical slices of specified volume, with each being a dissected tissue sample. As a result, counting stromal cells consists of choosing a pair of frames (consecutive pictures recorded by the in vivo confocal microscope), one frame having particles (stromal cells) in focus, and the co-frame showing a defocused but recognizable image of the same particles (optical shadows). The number of cells (n) is recorded from the clearest frame in a defined area A ($\mu m^2$). The distance d (μm) between the two frames is also recorded. The number of cells per unit volume (V) therefore equals to: V=Number of cells (n)/d (μm)×A ($\mu m^2$).

Ex Vivo Confocal Images

Appropriate corneal sections were immunohistochemically stained with different markers for different purposes. Staining with the nuclear stain Hoechst 33 258 was used to estimate the number of epithelial and stromal cells at the central or the peripheral cornea. For this purpose using AnalySIS® 3.2 software (Soft Imaging System, USA), the area of interest was first freehand drawn onto the TIFF file image of the appropriate region of the cornea and the value of the area was automatically given by the software. Using the manual count option, cells were then counted within that area and expressed per unit area.

Antisense Compound Application

30% Pluronic acid gel (BASF Corp) in phosphate buffered saline (molecular grade water) was used to deliver unmodified α1 connexin (connexin43) specific antisense ODNs to the subconjunctiva of anaesthetized rats following photorefractive keratectomy. In a pre-trial using an FITC tag, this formulation was shown to remain in the anterior chamber of the eye for up to 24 hours (not shown).

The antisense molecule used in these experiments was DB1 ((GTA ATT GCG GCA GGA GGA ATT GTT TCT GTC) (SEQ ID NO: 65). Addition of an FITC tag to DB1 ODN, viewed using confocal laser scanning microscopy, demonstrated intracellular penetration of the probe.

The ODN was applied at a 2 μM final concentration.

Monitoring Tissue Engineering or Remodeling Effects

After antisense application, the corneas were examined using a slit scanning in vivo confocal microscope at 2 h, 12 h, 24 h, 48 h, 72 hr, 1 week and 2 weeks post laser surgery. Control rats received laser surgery only.

Table 1 summarizes the number of corneas investigated at each time point.

TABLE 1

Number of control (C) and AS (ODN) treated corneas used for the in vivo follow-up using slit scanning in vivo confocal microscopy.

| | Within 2 hr surgery | 12 hr post-surgery | 24 hr post-surgery | 48 hr post-surgery | 72 hr post-surgery | 1 week post-surgery | 2 weeks post-surgery |
|---|---|---|---|---|---|---|---|
| Number of eyes (n) | 18 C<br>18 ODN | 10 C<br>10 ODN | 18 C<br>18 ODN | 10 C<br>6 ODN | 6 C<br>6 ODN | 4 C<br>4 ODN | 5 C<br>5 ODN |

ODN = AS ODN treated eyes (single administration after laser surgery)

Each cell layer of the cornea was analyzed and the cell type, number and appearance compared between the control and ODN treated groups.

Re-Epithelialization:

Treatment with anti-connexin43 ODNs promoted epithelial recovery. In 90% of AS ODN treated corneas, sliding epithelial cells were observed within 12 hours after PRK laser surgery, compared to none in controls (FIG. 1B). At this stage, only static endothelial cells were present in 30% control corneas (FIG. 1A) By 24 hours epithelial cells were seen in all controls and antisense treated corneas but 72% of treated versus 61% of controls showed actively sliding cells. This indicates that re-epithelialization is proceeding faster in the connexin43 specific AS ODN treated corneas than in controls.

Stromal Cell Densities:

Using a paired samples t-test with repeat measures to compare cell densities in the anterior and posterior stroma within each group as a function of time and a Mann Whitney non parametric statistical test to compare stromal cell counts between control and ODN treated corneas at the selected time points, the only statistically significant results were found at 24 hr post-laser surgery (Table 2). At this time point, in the control and ODN treated groups stromal cell density in the anterior stroma has increased considerably compared to the pre-surgery values (p value <0.05). In the posterior stroma of control corneas, stromal cell density has also increased compared to the pre-surgery value (p value <0.05) whilst in the posterior stroma of ODN treated corneas, stromal cell density is not statistically significantly different from the pre-surgery value (p value >0.05). When comparing stromal cell density between the two groups at the anterior and posterior stroma, the ODN treated corneas always showed lower stromal cell densities than the control corneas (p-value <0.05). This supports the idea that a smaller number of cells are involved in stromal re-modeling or engineering in the ODN treated corneas compared to the control corneas. This is the first report showing that application of anti-connexin43 ODNs reduces hypercellularity at the site of surgery. Ex vivo histochemical analysis (Example II) shows that this hypercellularity is associated with myofibroblasts which induce unwanted stromal matrix remodeling and scarring.

TABLE 2

Stromal cell counts in control and AS ODN treated corneas prior to and 24 hr following photorefractive keratectomy. Cell densities are given as means followed by standard deviations.

| Treatment | Time points | Anterior stromal cell count (#cells/mm$^3$) | Posterior stromal cell count (#cells/mm$^3$) |
|---|---|---|---|
| Control | Pre-surgery | 36469 ± 11122 (n = 17) | 33909 ± 8753 (n = 17) |
| ODN | Pre-surgery | 36769 ± 10932 (n = 17) | 34382 ± 8667 (n = 14) |
| Control | 24 hr post-surgery | 144643 ± 60989 (n = 17) | 46901 ± 26964 (n = 17) |
| ODN | 24 hr post-surgery | 93468 ± 53548 (n = 17) | 33510 ± 11350 (n = 14) |

Example II—Ex Vivo Analysis

Materials and Methods

Histology: Tissue Collection and Fixation

Appropriate numbers of animals (Wistar rats) were terminated at selected time points following photorefractive keratectomy and DB1 anti-connexin43 ODNs were administered to anaesthetized rats as described in experiment 1 above and corneal sections were prepared for histological analysis. Control rats had received laser surgery only. Whole eyes and control tissues were rinsed in Oxoid PBS prior to embedding in Tissue-Tek® OCT (Sakura Finetek, USA) and freezing in liquid nitrogen. When necessary (for the use of some antibodies), frozen tissues were later fixed in cold (−20° C.) acetone for 5 min after being cryocut.

Tissue Cutting

The procedure for cryosectioning was as follows: frozen blocks of unfixed tissue were removed from −80° C. storage and placed in the Leica CM 3050S cryostat for about 20 min to equilibrate to the same temperature as the cryostat (i.e. −20° C.). When equilibration of the tissue was achieved, the specimen was mounted onto a specimen disc with Tissue Tek® OCT. Sections of 12 μm (for H/E staining) or 25 μm thick (for immunolabeling) were cut and placed on Superfrost®Plus slides (Menzel-Gleser, Germany). Immediately following cryocutting, tissue blocks were placed back to −80° C. storage and slides supporting cryosections were either used immediately or stored at −80° C. Sectioning occurred parallel to the optical axis of the eye.

Haematoxylin/Eosin (H/E) Staining and Nuclear Staining

Slides were placed in glass racks to facilitate immersion in a series of different staining reagents. Racks were agitated when placing them into reagents to break surface tension and to drain them between each solution change. Prior to Gill's II Haematoxylin/Eosin staining, slides that were stored at −80° C. were first warmed up to room temperature for 1-2 min, then either fixed in cold acetone first and/or immediately hydrated with a quick dip in tap water. Slides were stained in Gill's II Haematoxylin for 2 min, after which excess stain was rinsed off in tap water. Stain differentiation was achieved by dipping in Scott's tap water substitute (STWS) for 4 sec. A rinse in running tap water for 1 min was then performed before staining in 1% eosin for 30 consecutive dips. Finally, sections were quickly rinsed in tap water, dehydrated through 95%, 100% EtOH, cleared in xylene, and mounted with DPX mounting medium (Sigma). For nuclear counter staining (in parallel with H/E or immunohistochemical analysis) Hoechst 33 258 (Sigma) was used. Measurement of cornea thickness was carried out on H/E stained sections.

Immunohistochemistry

Sections were immunolabeled for connexin43 using a site-specific monoclonal antibody, for myofibroblasts using an antibody recognizing alpha smooth muscle actin, for basal lamina deposition with an anti-laminin-1 antibody. In addition anti-vimentin antibodies were used to differentiate stromal keratocytes from myofibroblasts and a Ki-67 antibody was used to show cell proliferation.

Ex Vivo Histological Analysis

Figure 2:
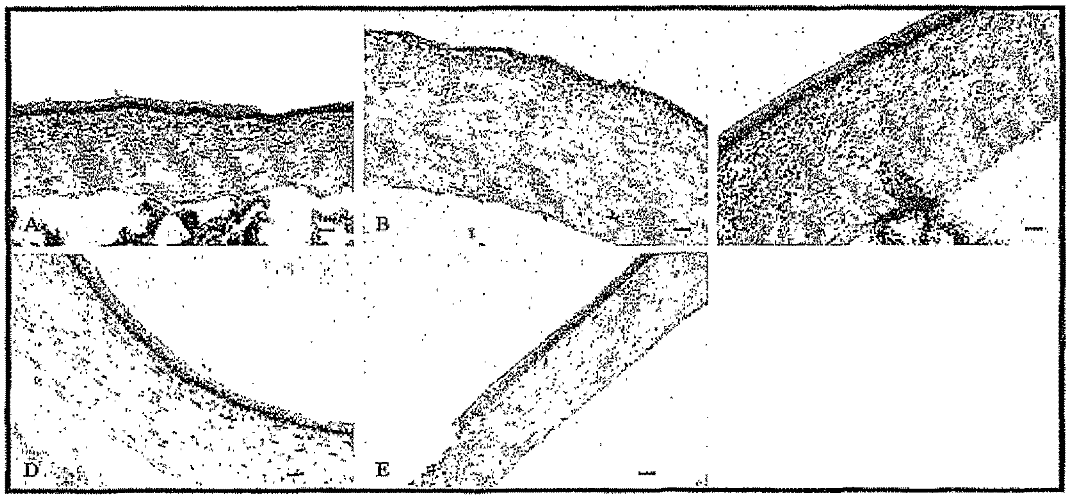
FIG. 2 shows histological examination of corneal remodeling in control (2A, 2B, 2C) and antisense oligodeoxynucleotide treated rat corneas (2D, 2E) 24 hours after excimer laser photoablation.

Results showed that lesions made by excimer photoablation had closed by 24 hr post-surgery (FIG. 2). The typical invasion of the stroma by mononucleated/multinucleated and/or round, ovoid cells at the periphery and at the center of the cornea was observed in both groups, most pronounced at 24 hr post-surgery, but with the antisense ODN treated group showing a significantly smaller number of these cells than the control group (FIG. 2A,B,C). This parallels the findings from the in vivo confocal photomicrographs shown in Example 1. The epithelium thickness was variable in control corneas as seen in FIG. 2 at the site of laser induced lesion (Figure A, B), and in the stoma beneath the ablated area (Figure A,B) and in the peripheral stroma (Figure C) there was an extensive invasion by round cells (hypercellularity) in control corneas. Also observed was a pronounced stromal edema in Figure B and Figure C. In the antisense ODN treated corneas the epithelium was of even thickness (Figure D,E) and in the central region (Figure D) and in the peripheral stroma (Figure E) there was little sign of stromal edema. Moreover, in the stroma there were few round cells present. Scales bars in FIG. 2 represent 20 microns.

Changes in stromal thickness following treatment with connexin43 ODNs after laser treatment are shown in Table 3, which compares changes in stromal thickness between control and ODN treated corneas. Stromal thicknesses were measured from appropriate histological stained sections. Statistical analysis of the data obtained for the ODN treated group using a paired samples t-test showed that at all three time points investigated (24 hr, 48 hr and 72 hr post-surgery) central stromal thickness is statistically significantly thinner than pre-surgery value ($p$ values $<0.05$) and peripheral stromal thickness is not significantly different from pre-surgery values. In contrast, control corneas show significant stromal swelling (edema) (FIG. 2 A, B, C) in both central and peripheral cornea (where the stroma doubles in thickness compared to pre-surgery values).

TABLE 3

Changes in stromal thickness following excimer laser surgery in control and AS treated corneas.

| Treatment | Time points | mean central stromal thickness (μm) | mean peripheral stromal thickness (μm) |
|---|---|---|---|
| Normal (no surgery) | Pre-surgery | 250 (n = 6)* | 110 (n = 10) |
| Control | 24 hr post- | 318 (n = 6) | 290 (n = 6) |
| ODN treated | surgery | 190 (n = 5) | 132 (n = 5) |
| Control | 48 hr post- | 307 (n = 6) | 206 (n = 5) |
| ODN treated | surgery | 158 (n = 5) | 105 (n = 5) |
| Control | 72 hr post- | 292 (n = 6) | 201 (n = 6) |
| ODN treated | surgery | 142 (n = 5) | 99 (n = 5) |

Cornea which is not subjected to surgery had a central stromal thickness of 250 μm, but excimer laser surgery was used to remove 70 μm of corneal tissue (including the epithelium and part of the stroma). The normal corneal epithelium is 50 μm thick (on average) and therefore 20 μm of stromal tissue was removed by laser surgery. Therefore, to statistically compare the central stromal thickness at 24 hr, 48 hr and 72 hr post-wounding to the pre-surgery central stromal thickness, an adjusted thickness loss and a central pre-surgery stromal thickness of 250−20=230 μm was used.

Figure 3:
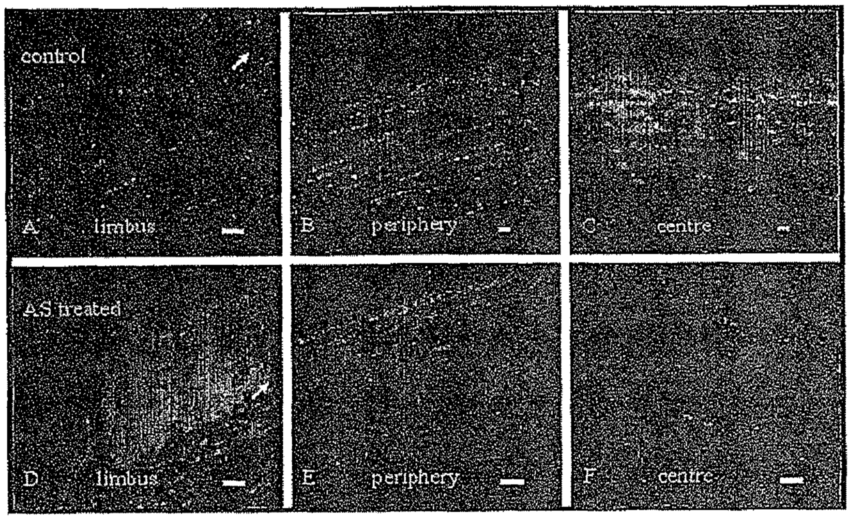
FIG. 3 provides micrograph images showing expression of connexin 43 protein in control (3A, 3B, 3C) and antisense oligodeoxynucleotide treated corneas (3D, 3E, 3F) at 24 hours after excimer laser ablation. The results demonstrate that connexin43 protein levels are reduced following treatment with anti-connexin43 ODNs and results in a smaller degree of cell recruitment in the stroma.

Reduction in Connexin43 Expression is Associated with Reduced Stromal Invasion and Reduced Epithelial Hyperplasia Microscopial observations showed a reduced level of connexin43 present in ODN treated corneas compared to control corneas. FIG. 3 shows combined micrograph images. Top row shows control corneas, the bottom row shows antisense ODN treated corneas. The typical invasion of the stroma by round cells was seen in both groups within 24 hours at the limbal, peripheral and central areas. However, a smaller density of round cells was exhibited in ODN treated corneas. At the limbus in both groups anti-connexin43 was evenly distributed throughout the stroma (3A, D) but the treated groups had less label in the periphery (3E) compared to controls (3B). By this stage connexin43 levels had returned to normal in the epithelium of both groups but control groups showed a scar like stroma (3C) or hyperplasia (see FIG. 4 below) whereas in antisense treated corneas a normal epithelium with normal levels of connexin43 was seen (3F). Scale bars A, D, E, F represent 10 microns; B and C represent 20 microns. In these figures connexin43 appears as white punctate labeling with cell nuclei appearing grey. The results shown in FIG. 3 suggest that connexin43 protein levels are reduced following treatment with anti-connexin43 ODNs and results in a smaller degree of cell recruitment in the stroma. In addition, only 7% of ODN treated corneas (0% at 24 hr post-surgery, 0% at 48 hr post-surgery, 20% at 72 hr post-surgery) show signs of epithelial hyperplasia compared to 31% control corneas (25% at 24 hr post-surgery, 67% at 48 hr post-surgery, 0% at 72 hr post-surgery). This was assessed on H/E stained and Ki-67 labeled sections.

Myofibroblast Labeling

Figure 4:
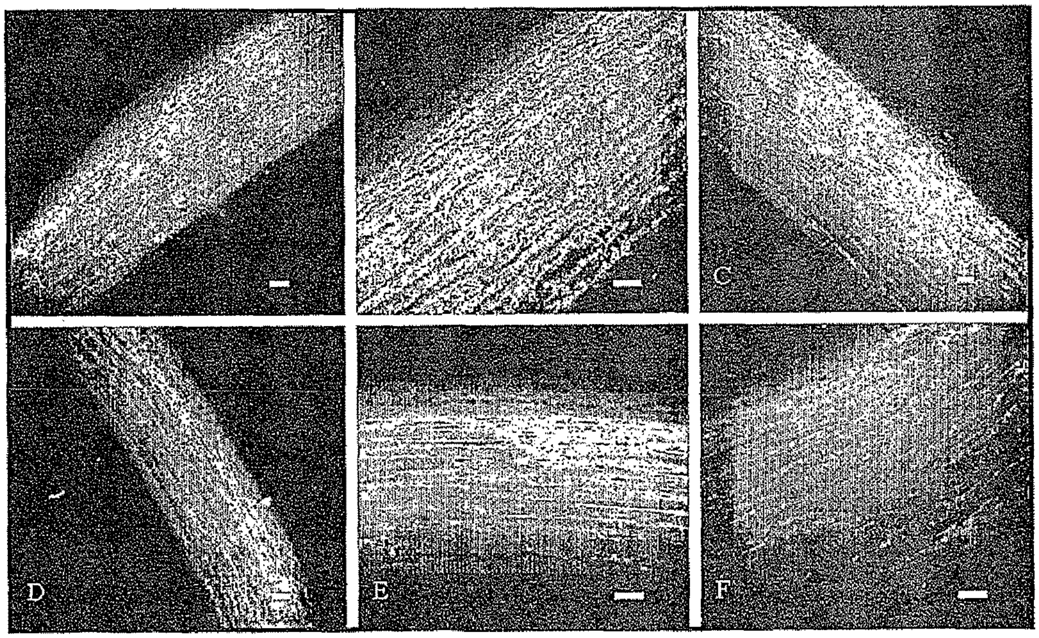
FIG. 4 shows myofibroblast labeling 1 week after surgery using alpha smooth muscle actin antibodies.

Labeling with vimentin antibodies indicated that the increased cell numbers in the stroma of control corneas compared with AS ODN treated corneas were not of undifferentiated keratocyte origin and labeling was therefore carried out with alpha-smooth muscle actin antibodies. This labeling showed that control corneas had a higher number of myofibroblasts beneath the site of surgery, but also in the surrounding peripheral stroma. This increase in myofibroblast numbers and area affected was evident at 24 hours and persisted over 48 and 72 hours through to at least one week after surgery (Table 4). FIG. 4 shows myofibroblast labeling (anti-alpha smooth muscle actin) at 1 week post-laser surgery. FIGS. 4A, B, and C are controls; and FIGS. 4D, E, and F are antisense treated corneas. By one week post-wounding, in the control corneas, low to moderate numbers of myofibroblasts are present in the anterior half of the peripheral stroma (4A), moderate to dense levels are present in the mid-peripheral stromal regions (4B), and moderate levels are seen in the anterior half of the stroma in central regions (4C). In contrast, in the treated corneas, very low numbers of myofibroblasts are present in peripheral (4D) or mid peripheral (4E) stroma and moderate to low numbers in central stroma (4F). In some cases in the central stroma, myofibroblasts are concentrated in the area just under the epithelium (not shown). Thus, the increased cell numbers seen in Example 1 (hyerpcellularity) and FIG. 2 above appears to be due to myofibroblast differentiation and invasion. Myofibroblasts are known to be responsible for scar tissue deposition in the stoma, with reduced crystalline deposition and increased secretion of wound collagen III (Ahmadi A. J. and Jakobiec F. A.; 2002; Int Ophthalmol Clin. Summer; 42(3):13-22).

TABLE 4

Summary of alpha smooth muscle actin labeling for myofibroblast in control and antisense ODN treated corneas.

| Time | Locations | Control corneas | AS treated corneas |
|---|---|---|---|
| 24 hr post-surgery | Periphery | 80% D in whole st<br>**20% M in whole st** | **100% M in anterior**<br>+B1⅓ st |
| | Mid-periphery | **100% D in whole st** | **100% M in anterior**<br>+B1⅓ st |
| | Centre | **100% L in anterior ¾ st** | **80% L in anterior ⅓ st**<br>**20% L below epi** |
| 48 hr post-surgery | Periphery | **83% M in whole st**<br>17% L in whole | **40% M in half anterior st**<br>60% L in half anterior st |
| | Mid-periphery | **50% D in whole st**<br>50% M in whole st | **100% D in half anterior st** |
| | Centre | **17% L under epi**<br>(hyperplasia)<br>50% D in whole st<br>**33% M in whole st** | 20% absent<br>**80% M in anterior ¾ st** |
| 72 hr post-surgery | Periphery | **33% L in anterior half st**<br>67% M in anterior half st | **40% L in anterior half st**<br>60% M in anterior half st |
| | Mid-periphery | **33% L in whole st**<br>67% Din whole st | **20% L in anterior half st**<br>80% M in anterior half st |
| | Centre | 17% absent<br>50% D in whole st<br>**33% M in whole st** | 20% absent<br>40% L in anterior half st<br>**40% M in anterior ¾ st** |
| 1 week post-surgery | Periphery | 60% M in half anterior st<br>**40% L in half anterior st** | **100% L in anterior**<br>+B1⅓ st |
| | Mid-periphery | **60% D in whole st**<br>40% M in whole st | **100% L in anterior half st** |
| | Centre | **60% M in anterior half st**<br>40% L in anterior half st | **60% M in anterior half st**<br>20% L in anterior half st<br>20% M under epi |

Numbers of myofibroblasts are quantified as dense (D), moderate (M), low (L) or absent.
Percentages refer to proportions of animals affected at the specified levels.
st = stroma,
epi = epithelium.
Significant differences between control and antisense treated corneas are highlighted in bold.

Basal Lamina Deposition

Figure 5:
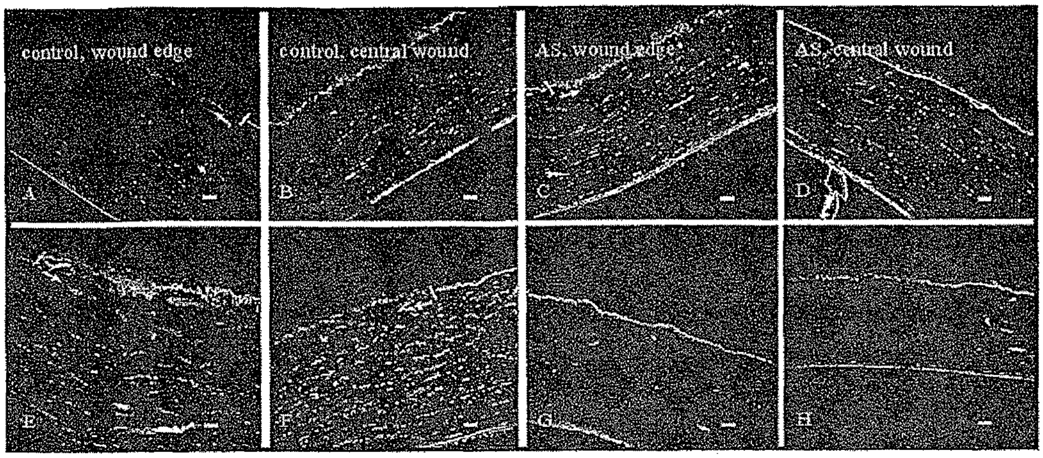
FIG. 5 shows laminin-1 labeling of control (5A, 5B) and connexin 43 antisense oligodeoxynucleotide treated corneas 24 hours (5A-5D) and 48 hours (5E-5H) after photorefractive keratectomy. At 24 hours controls had little and/or uneven laminin deposition at the edge of the ablated area (5A) and more centrally (5B) whereas antisense treated corneas showed a more regular deposition of laminin at both of these regions (5C, 5D). At 48 hours controls still do not have a continuous laminin deposition (5E—edge of the ablated area.

Following photorefractive keratectomy the basal lamina reforms along with the regrowing epithelium. Labeling with antibodies to laminin-1 shows that the reforming basal lamina is discontinuous and with an irregular epithelial-stromal attachment (FIG. 5). At 24 hours controls had little and/or uneven laminin deposition at the edge of the ablated area (FIG. 5A) and more centrally (FIG. 5B) whereas antisense treated corneas showed a more regular deposition of laminin at both of these regions (FIG. 5C, FIG. 5D). At 48 hours controls still do not have a continuous laminin deposition (FIG. 5E—edge of the ablated area; FIG. 5F—central) and it was very uneven (FIG. 5E). In contrast antisense ODN treated corneas had a continuous and relatively even basal lamina at the wound edge (FIG. 5G) and centrally (FIG. 5H). All scale bars in FIG. 5 represent 20 microns. Connexin43 antisense treated corneas formed a denser, more continuous basal lamina within 24 hours with less irregularity.

Figure 6:
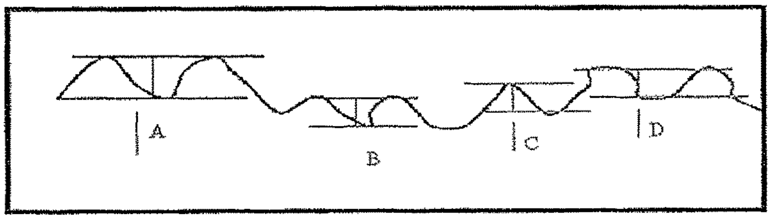
FIG. 6 shows a schematic diagram of laminin-1 irregularity quantification.

The laminin irregularity was quantified as shown in FIG. 6. The black solid line in FIG. 6 represents laminin-1 deposition. For each region the variance was measured as the difference between the top of a hill and the bottom of a valley (FIG. 6A, B, C, D). Control corneas had a mean variance of 6.98 microns compared with 4.74 microns in antisense ODN treated corneas. The difference between the two groups was statistically significant ($p<0.0001$).

Example III—Ex Vivo Tissue Engineering

Corneas were placed into an ex vivo organ culture model and specific connexin modulated using antisense ODNs. Two connexins were targeted in these experiments, connexin43 and connexin31.1. Connexin43 downregulation is used to demonstrate that connexins can be regulated in vitro, and connexin31.1 was targeted because this connexin is expressed in the outer epithelial layers of the cornea in cells about to be shed from the cornea. The aim was to engineer a thickening of epithelial tissue by reducing connexin31.1 expression.

Materials and Methods 30-34 day old Wistar rats were euthanized with Nembutal or carbon dioxide and whole rat eyes dissected. The ocular surface was dissected, disinfected with 0.1 mg/ml penicillin-streptomycin for 5 minutes and rinsed in sterile PBS. The whole eye was then transferred onto a sterile holder in a 60 mm culture dish with the cornea facing up. The eyes were mounted with the corneal epithelium exposed at the air-medium interface and cultured at 34° C. in a humidified 5% $CO_2$ incubator in serum free medium (Opti-MEM, Invitrogen) for up to 48 hours. 100 μl of medium was added drop wise to the surface every eight to twelve hours to moisten the epithelium. Medium levels were maintained to the level of limbal conjunctiva.

Antisense oligomers were mixed with 30% (w/w) Pluronic F127 gel (Sigma) on ice to a final 2 μM concentration and 10 μl applied onto the corneas. Each treatment had a sample size of 3 to 4 corneas per experiment. Preliminary experiments showed that double treatments of our positive control, DB1, for 8 hours had little effect on connexin43 protein expression in our corneal culture. Corneas were therefore cultured for 24 hours and connexin specific oligomers applied every 8 hours.

Immunohistochemical labeling was carried out as in Experiment 2 above using antibodies to connexins43, 26 (control) and 31.1. Tissue was also stained with H/E as above. Nuclei were counterstained with 0.2 μM propidium iodide. Images were collected on a Leica TCS 4D or TCS SP2 confocal laser scanning microscope with voltage and offset settings maintained within experimental groups to allow quantification of connexin levels. For quantification four optical slices through 3 microns were processed into a single extended focus optical image using the center of mass topographical projection option on the TCS 4D. Connexin label was quantified using NIH Image (Scion Corp. USA) after thresholding at 90-100 pixel intensity on the 256 grey scale image.

Figure 7:
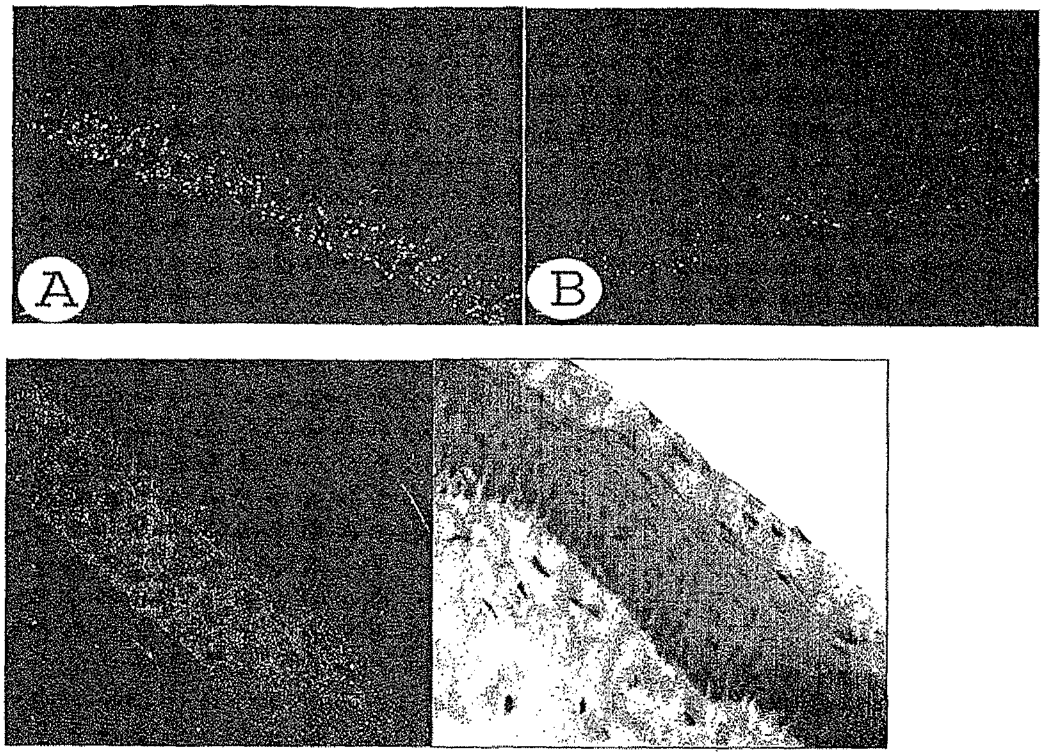
FIG. 7 shows immunohistochemical labeling for connexins 26 and 43 in control cultures (7A) and following three treatments with anti-connexin 43 oligodeoxynucleotides over a 24 hour period (7B), and after connexin31.1 specific antisense treatment (7C, 7D).

In corneas that have not undergone surgery, in vitro connexin turnover rates were relatively low compared to tissue remodeling processes in the excimer laser ablated corneas described in Examples 1 and 2 herein above. Nonetheless, after three treatments with antisense ODNs connexin levels were reduced by over 50% compared with controls (FIG. 7A, B shows connexin43 reduction in AS ODN treated corneas compared with controls). Connexin26 levels remained constant when the connexin43 specific antisense ODNs were applied (indicating that the reduction in connexin levels was specific, not a side effect of the treatment. In these images connexin43 appears as heavier spots in the basal two layers of the epithelium, connexin26 as finer punctate labeling predominantly in layers 2-6. Connexin31.1 antisense ODNs reduced levels of connexin31.1 but preliminary results also showed that the epithelial thickness (number of layers) increased within 24 hours (FIG. 7C, D). This increase in thickness was seen using H/E staining (FIG. 7D) and in the immunohistochemically (FIG. 7C) labeled sections.

The results described in this work form a basis for the use of connexin specific antisense ODNs in tissue-engineering, including specifically after excimer laser surgery of the cornea, or for in vitro organ culture for tissue engineering and transplantation. The experimental results provided herein demonstrate that a single treatment with connexin43 specific antisense ODNs following excimer laser photorefractive keratectomy has many beneficial uses, some of which are described hereinbelow.

Administration of connexin specific antisense ODNs promote epithelial cell movement. At 12 hr post-surgery 90% antisense treated corneas but no control corneas show the presence of sliding epithelial cells at the site of a laser induced lesion. Epithelial cells were present in 30% of control corneas but were static/non-sliding. Regulation of direct cell-cell communication by connexins can therefore be used to engineer changes in epithelial cell patterning.

Administration of connexin specific antisense ODNs promote controls hypercellularity associated with myofibroblast differentiation at the site of a laser induced lesion in the 24 hr to 48 hr post-surgery period. During this period, more control corneas (63%) than antisense ODN treated corneas (39%) show intense hypercellularity in the whole stroma. Regulation of direct cell-cell communication can therefore be used to modulate cell differentiation leading to modification of extracellular matrix.

Administration of connexin specific antisense ODNs controls stromal remodeling reducing haze at the site of a laser induced lesion in the 24 hr to 72 hr post-surgery period. In this period, more control corneas (64%) than antisense treated corneas (39%) show intense haze in the whole stroma.

Administration of connexin specific antisense ODNs inhibits stromal edema during the early stages of re-modelling. Regulation of direct cell-cell communication therefore improves outcomes from laser surgery.

Administration of connexin specific antisense ODNs reduces cell proliferation in the early stages of re-modelling. Regulation of direct cell-cell communication can therefore be used to regulate cell proliferation during tissue remodeling.

Administration of connexin specific antisense ODNs reduces epithelial hyperplasia by 78% (assessed from 24 hr to 72 hr post-surgery) enabling engineering of an even epithelium.

Administration of connexin specific antisense ODNs reduces myofibroblast activation up to 1 week post-surgery (and earlier loss of keratocytes). Regulation of direct cell-cell communication enables more precise control of tissue damage during surgical remodeling, providing improved predictability of outcome and fewer visual defects.

Administration of connexin specific antisense ODNs results in a more regular and denser epithelial-stromal adhesion matrix during tissue re-modelling. Regulation of direct cell-cell communication can therefore be used to engineer tissue basal laminae.

In addition, the ex vivo corneal culture model used herein indicates that regulation of direct cell-cell communication can be used to engineer tissue in vitro, for example increasing epithelial thickness using connexin31.1 antisense ODNs. This treatment also has implications in vivo, for example in the engineering a thicker cornea for the relief of corneal diseases such as keratoconus (a thinning of the epithelium).

The results show that active molecules which interfere with cell-cell communication can be used in tissue engineering and remodeling. Specifically, it is shown that antisense deoxynucleotides targeted at connexin proteins can be used in corneal re-modeling especially following corrective laser surgery, as well as for in vivo and in vitro tissue engineering.

The antisense compounds and methods described herein therefore have significant potential for improving the outcome of surgical interventions and ameliorating disease processes in the eye, and for tissue engineering.

Example IV

Ex Vivo Culture Model

Application of antisense oligodeoxynucleotides specific to the gap junction protein Connexin43 following brain or spinal cord injury in adult animal models blocks lesion spread, and reduces the inflammatory response and subsequent scar formation. We have taken our antisense approach even further and developed an ex vivo culture model for spinal cord segments and intact cords in order to elaborate repair strategies for established lesions.

Figure 8:
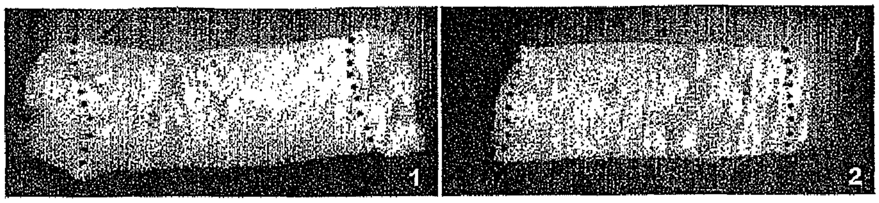
FIG. 8 shows spinal cord segments from P7 rat pups 24 hours after placing into culture. The control segment (1) is swollen (arrows) with tissue extruding from cut ends. Dotted lines mark the original excisions. Histological examination shows that cells are vacuolated and edemic. By day 5 these segments have activated microglia throughout and few surviving neurons. In contrast, the antisense treated segment (2) has significantly reduced swelling compared to controls ($p<0.001$) with minimal cellular edema and vacuolation. Even after 20 days in culture, neurons in the grey matter remain viable with activated microglia restricted to the outer edges.
Figure 9:
FIG. 9 shows neurons from a control treated segment (9A) and a Connexin43 antisense treated segment (9B). Neurons in a control segment are vacuolated and edematous and the surrounding tissue is disrupted, but neurons in the treated segment appear healthy and viable.

Spinal cords are excised from P7-P14 rat pups and divided into caudal, thoracic and rostral segments. Antisense oligodeoxynucleotides were applied in a Pluronic gel to the cut ends of the spinal cord segments during placement in culture, this results in a reduction of Connexin43 protein levels for 24-48 hours, significantly improving viability of the tissue. The most immediate and notable observation is that swelling does not occur (FIG. 8A-B, showing cord segments 24 hours after placing into culture). This treatment blocks the spread from the spinal cord cuts ends. Increased neuron survival in the grey matter of treated samples are clearly evident in the toluidine blue-stained resin sections (FIG. 9A). In sharp contrast, edema and vacuolation of neurons is seen throughout control tissue (untreated, gel only or gel with random oligodeoxynucleotides) in FIG. 9B.

Figure 10:
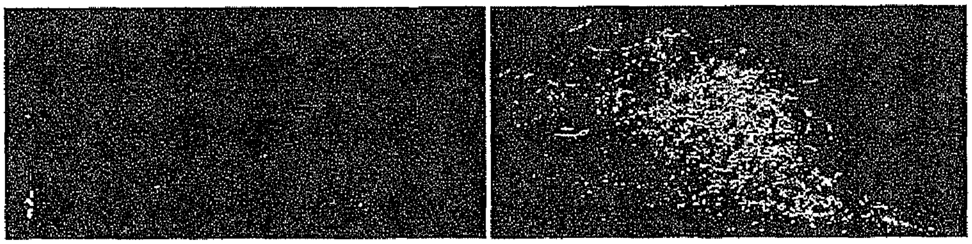
FIG. 10 illustrates MAP-2 immunolabeling near the ends of cultured spinal cord segments five days after placing into culture. Control segments have few viable neurons and little MAP-2 labeling (16% show any MAP-2 label) (10A) while 66% of treated segments have areas of MAP-2 expression at the cuts ends exposed to the medium and/or adjacent to remaining white matter material.

Subsequent labeling and immunohistochemical studies up to day 20 show that neurons in the treated cord segments (Neuronal-N labeling) survive for this period whereas few remain viable after as little as 3 days in the control segments. Isolectin-B4 labeling shows extensive activated (macrophagic phenotype) microglial invasion of control segments within five days in culture. In treated samples, activated microglial cells are restricted to the outer edges (where the white matter axon tracts were previously, and at the very cut ends). Notably, MAP-2 labeling, a marker for neuronal processes, indicates significant potential for regrowth in treated cord segments compared to control segments, which show no MAP-2 labeling at all (FIG. 10A-B).

Example V

Grafting of Peripheral Nerves Across Spinal Cord Lesions

For peripheral nerve grafting, we will retreat the tissue with Connexin43 specific antisense oligodeoxynucleotides at the time of grafting to prevent lesion spread from the graft site and microglial activation which leads to isolation of the graft from the host tissue neural population, restricting neuronal repair.

Peripheral Nerve Grafts:

Spinal cord segments are placed onto culture inserts (Millipore Millicell) in 35 mm dishes and the level of the culture medium raised until a miniscus forms over the segments. Connexin43 specific antisense oligodeoxynucleotides (30mers, 1 μM concentration) in a 30% Pluronic gel are placed immediately over the cord tissue. The gel sets as it warms to physiological temperatures and provides sustained release of the antisense oligomers. This treatment will reduce connexin43 protein levels for between 24 and 48 hours, with maximum reduction at 6-8 hours post-treatment. Such cord segments, stabilized in culture, and then re-exposed to incision trauma, shows the same symptoms as surgical intervention in vivo, including lesions expansion and tissue swelling into the cut area. This effect can be prevented by treatment with Connexin43 specific antisense oligomers at the time of the incision; and accordingly, the cut edges remain sharply defined with no obvious signs of edema or tissue swelling.

The segments are placed end to end but separated by a gap of 1-5 mm. After a one to three day stabilization period in culture, a graft of a sciatic nerve from a P7-P14 rat pup is placed across the gap. Previous studies have indicated that both sciatic nerve (or its saphenous branch) (Yick, L. W. et al., 1999, *Exp Neurol.* 159: 131-138; Aguayo, A. J. et al., 1981, *J. Exp. Biol.* 95: 231-240) or intercostal nerve (Cheng, H., et al., 1996, *Science,* 273: 510-513) grafting has considerable potential to induce axon elongation and the survival of neurons.

Immediately after grafting, re-treatment will commence with the Connexin43 antisense oligomers accompanied by neuronal behavior assessment over the subsequent days. Since the culture period after grafting are relatively short (up to 15 days) compared with in vivo studies (15 days to 7 months after surgery) a variety of markers to assess repair response as detailed below (Measuring outcomes) are used. Experiments are conducted with and without the addition of exogenous growth factors (such as acidic FGF or NGF) which might play a role in inducing neuronal proliferation and/or migration.

Example VI

Insertion of Schwann-Cell-Seeded Implants Between Segments Placed End to End

For implants between treated segments, Schwann cells have been selected as they have been shown to be strong promotors of axonal regeneration (Xu, X. M. et al., 1999, *J. Neurosci.* 11: 1723-1740; Keirstead, H. S. et al., 1999, *Exp. Neurol.* 159: 225-236).

Implanted cells can provide a permissive environment for central nervous system axon regeneration and have proven to be effective for inducing regrowth of axons. Schwann-cell-seeded mini-channel implants or matrigel placed between cord segments placed end to end are to be used for this application. The principle here is that for spinal repair interventions, one would ultimately wish to excise scar tissue and fill the space with implant material. The methods used are described by Morrissey et al. and Xu et al. (Morrissey, T. K. et al., 1991, *J. Neurosci.* 11: 2433-2442; Xu, X. M. et al., 1995, *J. Comp. Neurol.* 351: 145-160). Essentially, sciatic nerves are obtained from adult rats, the epineurium and connective tissue are then removed and 1 mm long explants are placed into culture with Dulbecco's Modified Eagle's Medium (DMEM-Gibco, USA). Outgrowth of migratory cells are predominantly fibroblasts and the explants are moved to a new dish as these reach confluency. This is repeated over three to five passages until the cells that emerge are primarily Schwann cells. These are dissociated and grown up for seeding into copolymer or matrigel guidance channels (Schmidt, C. E. and Baier Leach, J., 2003, *Ann. Rev. Biomed. Eng.* 5: 293-347). Once implant material is prepared, cultured segments will have their ends recut to mimic scar excision, and placed end to end with implant material wedged between. Immediately after grafting, samples are re-treated with the Connexin43 antisense oligomers and the neuron behavior is monitored over subsequent days.

Measuring Outcomes

Time course experiments are carried out for both peripheral grafts and implants to establish whether there is immediate, late or continuous response to the graft tissues. Several markers are used to assess neuronal response and repair potential. These include: Neuronal (antibodies to Neuronal-N), neurofilament (antibodies to MAP-2 and SMI-31) and cytoplasmic markers (CMFDA) and membrane dyes (Di-I or Axon grease-Molecular Probes, Oregon, USA). Increased neural sprouting, increased axon migration distance (bridge length to distance migrated ratio) and increased numbers of axons growing toward or across the graft are specifically monitored. Cell specific markers (GFAP for astrocytes, Isolectin-B4 for microglial cells, and S-100 for Schwann cells). Glial cell distribution and density, and levels of myelination are assessed. Anti-CGRP (a peripheral nerve marker) are used to distinguish between axons of peripheral nerve origin as opposed to those regenerating from the cord segments. GAP-43 (growth associated protein) antibodies are used to identify neuronal growth cones. Toluidine blue stained semithin sections and electron microscopy of graft cross sections are used for morphological analysis.

Secondary antibodies are conjugated with Alexa dye. For double or triple labeling, we use Zenon probes (Molecular Probes, Oregon, USA) where appropriate. All antibody and dye labels are analysed using The University of Auckland's Biomedical Imaging Research Unit Leica TCS 4D and SP2 confocal laser scanning microscopes. Electron microscopy is performed on a Hitachi H-7000 electron microscope. Image analysis programmes (AnalySIS or NIH Image J) are used to quantify differences between control and treated grafts.

Example 7: Antisense Oligodeoxynucleotide Design

Materials

Materials used herein include art-recognized antibodies and plasmids; such as, for example, plasmids for rat connexin 43 (T7291),) and connexin 26; plasmids for mouse connexin 43 and connexin 26 (Invivogen, USA), mouse anti rat connexin 43 and rabbit anti rat connexin 26 from Zymed (51-2800); and goat anti mouse Alexa 488 and goat anti rabbit Alexa 568 secondary antibodies from Molecular Probes, Eugene Oreg. Nuclei were stained using Hoechst 33258 dye (Sigma). All deoxyribozymes and oligodeoxynucleotides were purchased from Sigma Genosys, Australia, as desalted oligomers. TaqMan labeled oligomers were purchased from Applied Biosystems, USA. All oligodeoxynucleotides were purchased as unmodified phosphodiester oligodeoxynucleotides.

Deoxyribozyme Design

The deoxyribozyme design and testing was similar to that described in previous studies (Santoro, S. W. and Joyce, G. F. *Proc. Natl Acad. Sci. USA*, (1997), 94, 4262-4266 and Cairns, M. J. et al., (1999) Nat. Biotech 17, 480-486). In brief, all AU and GU sites in the mRNA sequence of the target connexin were selected with 8 or 9 nucleotides on each side of the A or G. The deoxyribozymes are the complement of this sense coding sequence with the "A" or "G" replaced with the "10-23" catalytic core "ggctagctacaacga" (SEQ ID NO: 66). Control deoxyribozymes had a defective catalytic core of "ggctaActacaacga" (SEQ ID NO: 67) with a single point mutation (g→A) Santoro, S. W. and Joyce, G. F. Biochem 37, 13330-13342). We also designed GC and AC specific deoxyribozymes to cover gaps left by AU and GU deoxyribozymes not meeting the three requirements below. Each deoxyribozyme was named according to the position of "A" or "G" nucleotides from the start ATG codon. Those deoxyribozymes selected for in vitro assay had to fulfill three requirements:

1. Thermo stability: the chosen deoxyribozymes should not form stable secondary structures, either hairpin looping or homodimers. Any deoxyribozyme with a hairpin or homodimer melting temperature greater than 37° C. was discarded as presumptively unable to bind to the target sequence at physiological temperatures.

2. Affinity: The total ΔG values of both binding arms should not be greater than 30 Kcal. Each individual binding arm is between −10 to −15 kcal. This is a compromise between the specificity of binding/miss priming (due to higher CG content) and an effective binding/turnover rate requirement for deoxyribozymes. The binding arm length either side of the cleavage site is adjusted to find the ideal ΔG value and step (1) repeated to check.

3. Specificity: All target binding sequences were BLASTn searched with Gene Bank to check for specificity (http://www.ncbi.nlm.nih.gov/BLAST/). Deoxyribozymes with homology to other connexin genes or other known rodent genes were discarded.

In Vitro Testing of Deoxyribozymes

The mouse connexin43 and connexin26 cDNAs were excised from the pORF vector (Invivogen) with NcoI and NheI and subcloned into pGEM-T (Promega) prior to in vitro transcription. Both the full-length 2.4 kb rat connexin43 cDNA and the full coding 1.4 kb rat connexin43 cDNA including 200 nucleotides of 5'-untranslated regions were used for in vitro transcription. Full length mRNA was transcribed from linearized plasmid DNA using a Promega Riboprobe Kit. The resulting mRNA was purified with a PCR spin column (Qiagen). Concentration was determined by spectrophotometer reading of OD at 260 nm. Deoxyribozymes (40 μM final concentration) and mRNA (0.01 to 0.05 μg/μl total mRNA) were then separately pre-equilibrated with a 2× cleavage buffer (100 mM Tris 7.5; 20 mM $MgCl_2$; 300 mM NaCl; 0.02% SDS) for 5-10 minutes at 37° C. mRNA and deoxyribozyme mix were then incubated for one hour at 37° C., following which, 10× Bluejuice (Invitrogen) was added to stop the cleavage reaction and the mixture kept on ice. The reaction mixture was then loaded onto a pre-run 4% polyacrylamide gel (19:1 acryl:bis ratio, BioRad) in 1×TBE buffer and 7M Urea and run for up to 2 hours. Gels were stained with a 1:10 000 dilution of SYBR green II (Mol Probes, USA) in TBE buffer and imaged using a BioRad Chemi Doc system.

Design of Antisense Oligomers

Antisense sequences were chosen based on the twenty-nucleotide sequences of the deoxyribozyme binding arms that were successful in cleaving the mRNA in vitro. Selected sequences were chosen for use in the design of 30-mer oligos (Brysch, W. (1999). Antisense Technology in the Ventral Nervous System, ed. H. A. Robertson; Oxford University Press 21-41) and (Walton S., et al., (2002) Biophysical Journal 82, 366-377). In brief, sequence related side effects such as partial sequence homology of 8-10 CG base pairings to unrelated genes, GGGG and CpG motifs were avoided. Antisense sequences with the 3'-end ending with a Thymidine or more than three C or Gs in the last five nucleotides are also avoided if possible to prevent miss priming. Oligomers that form stable secondary structures such as homodimers, palindrome motifs or secondary hairpin structures will impede oligomers binding to the target mRNA. Control oligomers, including sense, scrambled, reverse and mismatch oligomers were also designed to assess possible chemistry related side effects due to cross hybridization, non specific protein binding, and toxicity.

Corneal Organ Culture and Treatment with Antisense Oligonucleotides 30-34 day old Wistar rats were euthanized with carbon dioxide and whole rat eyes dissected. The ocular surface was dissected, disinfected with 0.1 mg/ml penicillin-streptomycin for 5 minutes and rinsed in sterile PBS. The whole eye was then transferred onto a sterile holder in a 60 mm culture dish with the cornea facing up. The eyes were mounted with the corneal epithelium exposed at the air-medium interface and cultured at 34° C. in a humidified 5% $CO_2$ incubator in serum free medium (Opti-MEM, Invitrogen) for up to 48 hours. 100 μl of medium was added drop wise to the surface every eight to twelve hours to moisten the epithelium. Medium levels were maintained to the level of the limbal conjunctiva.

Antisense oligomers were mixed with 30% (w/w) Pluronic F127 gel (Sigma) on ice to a final 2 μM concentration and 10 μl applied onto the corneas as previously described. (See Becker, D. L., et al.; (1999b) *Dev. Genet.* 24:33-42; Green, C. R., et al.; (2001), Methods Mol Biol 154, 175-185). Each treatment had a sample size of 3 to 4 corneas per experiment. Preliminary experiments showed that double treatments of our positive control, DB1, for 8 hours had little effect on connexin43 protein expression in our corneal culture. Corneas were therefore cultured for 24 hours and connexin43 specific oligomers applied every 8 hours. However, we found that endogenous connexin26 expression is affected if the culture was maintained for 24 hours. Hence, we reduced the culture period for connexin26 specific oligomers treated corneas to 12 hours, with application of antisense oligomers every 4 hours. Medium was changed ten minutes prior to every repeat application of antisense or control oligomers. At defined times, corneas were rinsed with PBS, immersed in OCT (Tissue Tek, Japan) and snap-frozen in liquid nitrogen. 25 μm cryosections were subsequently cut with a Leica cryostat (CM3050s) and mounted on SuperFrost Plus slides (Menzel, Germany). For both Cx43 and Cx26 mRNA analysis corneas were collected 8 hours after a single antisense treatment.

RNA Isolation and Real-Time PCR

Total RNA was extracted from isolated rat corneas using TRIzol reagent (GIBCO, Invitrogen, USA) according to the manufacturer's protocols. The quality of RNA samples was assessed by electrophoresis through ethidium bromide stained agarose gels and the 18S and 28S rRNA bands visualized under UV illumination. The extraction yield was quantified spectrophotometrically at 260 nm. For real-time PCR, cDNA was prepared from 5 ug of total RNA by using oligo dT and superscript II Rnase H-reverse transcriptase (Life Technologies, Invitrogen, USA) in a final reaction volume of 20 μl. Quantitative PCR reaction was carried out in 96-well optical reaction plates using a cDNA equivalent of 100 ng total RNA for each sample in a volume of 50 μl using the TaqMan Universal PCR Master Mix (Applied Biosystems, USA) according to the manufacturer's instructions. PCR was developed on the ABI PRISM 7700 Sequence Detection system instrument (Applied Biosystems, USA). The thermal cycling conditions comprised an initial denaturation step at 95° C. for 10 minutes and 50 cycles of two-step PCR, including 15 seconds of denaturation at 95° C. and 1 minute of annealing-elongation at 60° C., using the standard protocol of the manufacturer. All experiments were repeated in triplicate. The monitoring of negative control for each target showed an absence of carryover.

Amplification of 18S rRNA was performed as an internal reference against which other RNA values can be normalized. If the efficiencies of the target and 18S rRNA amplifications were approximately equal, then the formula $2^{-\Delta\Delta Ct}$ was used to calculate relative levels of mRNA without the need for a standard curve. If the efficiency of amplification of the target and 18SrRNA were significantly different, a relative standard curve method was used to calculate absolute quantities of mRNA and 18S rRNA for each experiment from the measured Ct, and then the relative mRNA levels of the target gene compared with control quantified after normalization to 18S rRNA.

All calculations were performed by using PRISM 3.02 software (GraphPad, San Diego). Statistical difference between groups was determined by using the Student's t test. Comparisons among several groups were performed by ANOVA, and significance was calculated by using Dunnett's multiple comparison test.

Assessment of Antisense Oligomers Efficiency on Blocking Translation

Cy3 and TaqMan (Fam, Tamra) labeled oligomers were used to assess penetration and stability. Cy3-labeled oligomers (Sigma Genosys) and TaqMan (FAM, TAMRA) labeled oligomers (Applied Biosystems) were applied with Pluronic gel to measure both the stability and the penetration of oligomers into the corneal epithelium. The treated corneas were fixed in 4% paraformaldehyde for 20 minutes, mounted in 1% agar and viewed under a 40× water immersion lens as whole mount. The depth of oligomer penetration was measured using the Z-scan option on a Leica SP2 confocal microscope and plots of intensity versus z-distance measured. The breakdown of TaqMan oligomers was measured using the Lamdba scan option on the confocal. Fluorescence resonance energy transfer (or FRET) between the FAM (donor) and TAMRA (receptor) molecule occurs in intact 30mer oligomers. When the oligomer is broken down FAM and TAMRA are no longer in close proximity and FRET no longer occurs.

Immunofluorescent Labelling

Immunolabeling of connexins on corneal sections were performed as previously described. In brief, sections were blocked in 10% goat serum and incubated with primary antibody at 1:250 (mouse anti rat connexin43) or 1:500 (rabbit anti rat connexin26) at 4° C. overnight. The sections were then washed with PBS, incubated with 1:400 dilution of Alexa 488 labeled secondary antibody at room temperature for 2 hours and then fixed in 4% paraformaldehyde and counterstained with 0.2 μM Propidium Iodide or a 1:50 dilution of Hoechst 33258 for 10 min. Sections were mounted in Citifluor antifade medium (Agarscientific UK). All images were collected using either a Leica TCS-4D or Leica SP2 confocal laser scanning microscope and stored as TIF files. All images were collected using consistent voltage (520-540 V) and offset (−2) settings. The voltage and offset were set using the glow-over-under display option to maximize the gray scale for images of control tissue. The same settings were then used for all samples within the same experiment.

For quantification, four optical slices through three micrometers were processed into a single extended focus optical image by using the center of mass topographic projection option on the TCS-4D. Spots of connexin label were counted using NIH image (Scion Corp.) after thresholding at 90 to 100 pixel intensity on the 256 grey scale image. The area of corneal epithelium was also measured and a connexin density per unit area was calculated. An average of four extended focus images were used to calculate the absolute connexin density of each cornea. This number was then normalized with the medium connexin density of either sense control treated or gel treated corneas. We have represented the data as percentage knock down when comparing different treatments.

Deoxyribozymes Selectively Cleave mRNA In Vitro

Figure 11:
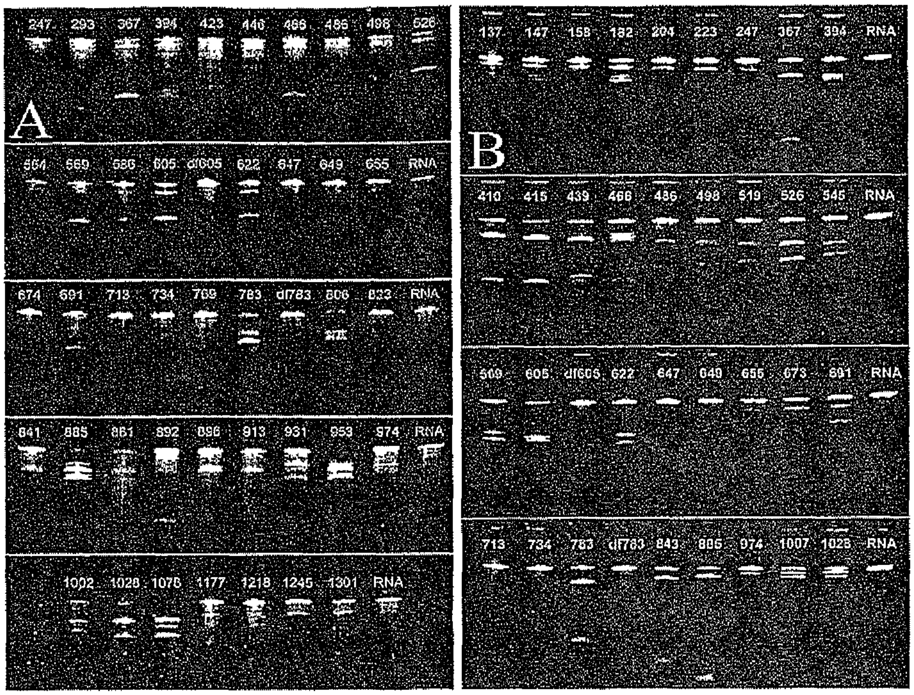
FIG. 11 illustrates that deoxyribozymes selectively cleave specific regions of target connexin-43 mRNA in vitro. A 2.4 kb rat connexin-43 mRNA (11A) and 1.2 kb mouse connexin-43 mRNA (11B) were transcribed in vitro from plasmid and incubated with various deoxyribozymes for 1 hour. Region 896-953 of rat mRNA (11A) was inconclusive because no deoxyribozymes were designed for corresponding region in mouse. Deoxyribozymes cleavage of region 367-466 in mouse mRNA (11B), does not match results from rat connexin-43 mRNA, probably due to the presence of 200 base pair of 5' untranslated region in rat mRNA. Defective control deoxyribozymes with single point mutation, df605 and df783, showed that such cleavages were specific. Some non-specific miss priming by deoxyribozymes against mouse mRNA were also observed by mouse dz1007 and dz1028. Overall, deoxyribozymes targeting the 526-622, 783-885, and 1007-1076 base regions showed significantly cleavage in both rat and mouse mRNA species.

Sixty six deoxyribozymes were designed specifically against rodent connexin43 mRNA (Table 5). Twenty two of these deoxyribozymes were designed to recognize both mouse and rat connexin43 mRNA. We also purchased two defective deoxyribozymes with a single point mutation in the "10-23" catalytic core as negative controls. The deoxyribozyme cleavage results were similar for the rat connexin43 mRNA 1.1 Kb in length (not shown) and the rat connexin43 mRNA 2.4 Kb in length (FIG. 11A). Both rat (FIG. 11A) and mouse (FIG. 11B) connexin43 mRNA appear to have similar regions accessible to the deoxyribozymes. The results indicate four regions on the rodent connexin43 mRNA that are exposed and available for deoxyribozyme cleavage. These regions are around 367-466, 526-622, 783-885, and 1007-1076 bases from the start ATG codon. The two defective deoxyribozymes, a1df605 and a1df783, showed no cleavage of rodent connexin43 mRNA. Deoxyribozymes designed against the 200 base pair 5' untranslated region of rat connexin43 mRNA also did not show any cleavage activity.

TABLE 5

Summary of deoxyribozyme (dz) and antisense (as) oligodeoxynucleotide sequences showing various degrees of in vitro and in vivo activity against rat connexin43.

| | Name | ODN Sequence 5' to 3' | in vitro | in vivo protein | In vivo mRNA |
|---|---|---|---|---|---|
| SEQ ID NO: 32 | r43dz14 | CCAAGGCA ggctagctacaacga TCCAGTCA | − | | |
| SEQ ID NO: 33 | a1dz605 | CCGTGGGA ggctagctacaacga GTGAGAGG | + | | |
| SEQ ID NO: 34 | a1df605 | CCGTGGGA ggctaActacaacga GTGAGAGG | − | | |
| SEQ ID NO: 35 | r43dz769 | AGTCTTTTG ggctagctacaacga TGGGCTCA | − | | |
| SEQ ID NO: 36 | a1dz783 | TTTGGAGA ggctagctacaacga CCGCAGTC | ++ | | |
| SEQ ID NO: 37 | a1df783 | TTTGGAGA ggctaActacaacga CCGCAGTC | − | | |
| SEQ ID NO: 38 | r43dz885DB1 | ACGAGGAA ggctagctacaacga TGTTTCTG | +++ | | |
| SEQ ID NO: 39 | r43dz892 | TTGCGGC ggctagctacaacga CGAGGAAT | − | | |
| SEQ ID NO: 40 | r43dz953 | CCATGCGA ggctagctacaacga TTTGCTCT | +++ | | |
| SEQ ID NO: 41 | r43dz1076 | TTGGTCCA ggctagctacaacga GATGGCTA | +++ | | |
| SEQ ID NO: 42 | DB1 | GTA ATT GCG GCA GGA GGA ATT GTT TCT GTC | | + | ++ |
| SEQ ID NO: 43 | DB1s | GACAGAAACAATTCCTCCTGCCGCAATTAC | | − | − |
| SEQ ID NO: 44 | r43as14 | CCAAGGCACTCCAGTCAC | | − | |
| SEQ ID NO: 45 | a1as605 | TCCGTGGGACGTGAGAGGA | | ++ | ++ |
| SEQ ID NO: 46 | r43as769 | AGTCTTTTGATGGGCTCA | | up | up |
| SEQ ID NO: 47 | a1as783 | TTTTGGAGATCCGCAGTCT | | + | ++ |
| SEQ ID NO: 48 | r43as885 | CACGAGGAATTGTTTCTGT | | + | |
| SEQ ID NO: 49 | r43as892 | TTTGCGGCACGAGGAATT | | − | |
| SEQ ID NO: 50 | a1as953 | CCCATGCGATTTTGCTCTG | | + | |
| SEQ ID NO: 51 | a1as1076 | GTTGGTCCACGATGGCTAA | | + | |

Table 5 shows those ribozyme and antisense sequences selected on the basis of in vitro ribozyme cleavage studies for in vivo analysis (mRNA and/or protein levels) or where defective ribozyme controls (SEQ ID NO:56 and SEQ ID NO:59) are compared with normal ribozymes.

b2df379) showed no cleavage of rodent connexin26 mRNA. The deoxyribozymes cx26dz341, dz351, dz375, dz379 consistently cleave rat connexin26 mRNA at a higher rate compared to mouse connexin26 mRNA. On the other hand, mcx26dz153 and dz567 appear to be superior connexin26 deoxyribozymes in mouse when compared to rat.

TABLE 6

Deoxyribozyme (dz) and antisense (as) oligodeoxynucleotide sequences showing various degrees of in vitro and in vivo activity against rodent connexin26.

| | Name | ODN Sequence 5' to 3' | in vitro | in vivo protein | In vivo mRNA |
|---|---|---|---|---|---|
| SEQ ID NO: 52 | m26dz153 | GTTGCAGA ggctagctacaacga AAAATCGG | +++ | | |
| SEQ ID NO: 53 | b2dz330 | GTTCTTTA ggctagctacaacga CTCTCCCT | +++ | | |
| SEQ ID NO: 54 | b2dz341 | GTCCTTAAA ggctagctacaacga TCGTTCTTT | +++ | | |
| SEQ ID NO: 55 | b2dz351 | TCTCTTCGA ggctagctacaacga GTCCTTAAA | +++ | | |
| SEQ ID NO: 56 | b2df351 | TCTCTTCGA ggctaActacaacga GTCCTTAAA | – | | |
| SEQ ID NO: 57 | b2dz375 | GATACGGA ggctagctacaacga CTTCTGGG | +++ | | |
| SEQ ID NO: 58 | b2dz379 | CTTCGATA ggctagctacaacga GGACCTTC | +++ | | |
| SEQ ID NO: 59 | b2df379 | CTTCGATA ggctaActacaacga GGACCTTC | – | | |
| SEQ ID NO: 60 | m26dz567 | GGTGAAGA ggctagctacaacga AGTCTTTTCT | +++ | | |
| SEQ ID NO: 61 | b2as330n | CCTTAAACTCGTTCTTTATCTCTCCCTTCA | | – | ++ |
| SEQ ID NO: 62 | b2rv330n | ACTTCCCTCTCTATTTCTTGCTCAAATTCC | | – | – |
| SEQ ID NO: 63 | r26as375n | TACGGACCTTCTGGGTTTTGATCTCTTCGA | | – | + |
| SEQ ID NO: 64 | r26rv375n | AGCTTCTCTAGTTTTGGGTCTTCCAGGCAT | | – | |

Figure 15:
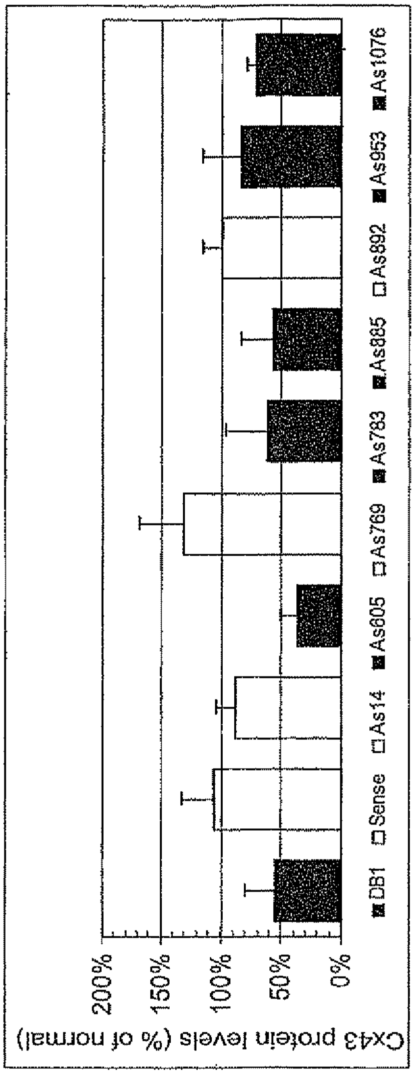
FIG. 15 shows that connexin43 antisense oligomers selectively reduce connexin-43 proteins expression in rat corneas. Each spot represents a single cornea with different treatments. The solid spot (black colored, DB1, as605, as783, as885, as953 and as1076) showed an average of 36% to 85% reduction in connexin-43 expression when compared to white coloured spots (DB1 sense, as14, as769 and as892). All antisense oligomers predicted by deoxyribozyme tertiary prediction assay to have little or no effect, showed an average of 85% to 134% of normal connexin-43 expression. All experiments were normalised with the medium connexin-43 density treated with DB1 sense and as a result two negative oligomers (as769 and as892) showed greater connexin-43 density than DB1 sense control treatment.

The oligomer names have the prefix r43 where they are specific only to rat connexin43 only; the prefix a1 denotes specificity against both mouse and rat. All oligomer sequences are unmodified phosphodiester oligodeoxynucleotides. "ggctagctacaacga" SEQ ID NO: 66) represents the "10-23" catalytic core of the deoxyribozymes and "ggctaActacaacga" (SEQ ID NO: 67) is the defective mutant control. DB1 is a 30-mer version of as885 (marked in lower case) and DB1s is the sense control of DB1 sequence. In vitro effects were measured as percentage mRNA cleavage by individual deoxyribozymes. In vivo effects were measured by immunolabelling of connexin43 in corneal sections (refer to FIG. 15) or Real-Time PCR assessment of surviving mRNA levels (refer to FIG. 16). +++ means >75%, ++ means between 50% to 75%, + means between 25% to 50%, and – means between 0% to 25% in vitro cleavage of mRNA or in vivo reduction of protein and mRNA expressions. up means an increase in connexin43 protein expression when compared to DB1 sense or gel only control treatment.

Figure 12:
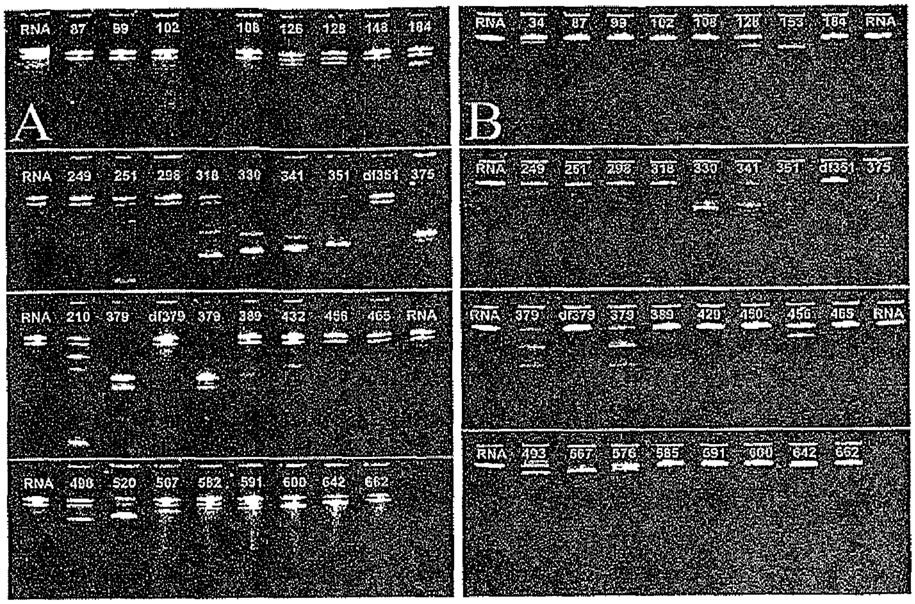
FIG. 12 illustrates that deoxyribozymes selectively cleave specific regions of target connexin-26 mRNA in vitro. A 0.7 kb rat (12A) and mouse (12B) connexin-43 mRNA was transcribed in vitro from plasmid and incubated with various deoxyribozymes for 1 hour. The cleavage results show that rodent connexin26 mRNA has at least two regions that are targeted by deoxyribozymes, in the 318-379 and 493-567 base regions. Defective control deoxyribozymes with single point mutation, df351 and df379, showed that such cleavages were specific.

We also tested forty four deoxyribozymes designed specifically against rodent connexin26 mRNA (Table 6), of which 17 deoxyribozymes match both mouse and rat connexin26 mRNA. The rat connexin26 mRNA appeared as a double band on the gel owing to the presence of two T7 RNA polymerase promotors on the cloning plasmid. The cleavage results show that connexin26 mRNA has at least two regions accessible to deoxyribozymes, in the 318-379 and 493-567 base regions (FIG. 12A, 12B). These figures show that most consistently cleaving deoxyribozyme is the cx26dz330, which cleaves both species of mRNA within one hour. The two defective deoxyribozymes (b2df351 and Table 6 shows those ribozyme and antisense sequences that consistently cleaved the mRNA in vitro, were selected on the basis of in vitro ribozyme cleavage studies for in vivo analysis (mRNA and/or protein levels), or where used as defective ribozyme controls. The oligomer names have the prefix m26 or r26 where they are specific only to mouse or rat connexin26 mRNA respectively, and the prefix b2 denotes specificity against both species. All oligomer sequences are unmodified phosphodiester oligodeoxynucleotides. "ggctagctacaacga" (SEQ ID NO: 66) represents the "10-23" catalytic core of the deoxyribozymes and "ggctaActacaacga" (SEQ ID NO: 67) is the defective mutant control. A reverse control (rv) was also used to control for any non-specific effects of antisense oligomers. In vivo effects were measured by immunolabelling of connexin26 in corneal sections and Real-Time PCR of the target mRNA expression (refer to FIG. 17). +++ means >75%, ++ means between 50% to 75%, + means between 25% to 50%, and – means between 0% to 25% in vitro cleavage of mRNA or in vivo reduction of protein and mRNA expressions.

Fluoresecently Labeled ODN in Pluronic Gel can Penetrate the Corneal Epithelium

Figure 13:
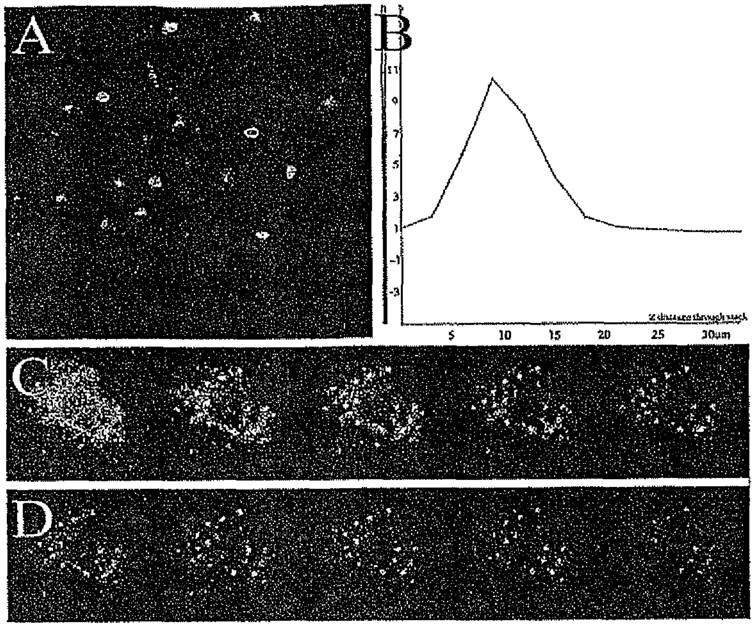
FIG. 13 shows antisense oligomer penetration and stability in cultured corneas for up to one hour. Cy3 labeled oligomers show punctate nuclear and cytoplasmic labeling one hour after delivery with Pluronic gel (13A). The rate of visible Cy3 penetration was 10-15 μm after one hour in corneal epithelium (13B). Taqman labeled oligomer probes was used to measure the stability of antisense oligomers inside epithelial cells using Lambda scan with each panel showing a 5 nm light emission spectrum towards the red colour (13B). Intact Taqman probe shows Fluorescence Resonance Energy Transfer with the red fluorescence light of TAMRA represented on gray-scale (13D) while breakdown products are represented as green fluorescence as expected from FAM (also shown on gray-scale (13C)). The effective antisense oligomer concentration in cells could be lower than that can be detected by fluorescence technique.

Rat corneas maintain expression of both connexin43 and connexin26 in organ culture and are easily accessible to the delivery of antisense oligomers by 30% Pluronic F-127 gel. The rat cornea organ culture was therefore selected as the model system to test the effectiveness of the antisense oligodeoxynucleotides designs derived from the in vitro model. We cultured rat corneas for 24 hours and found that the endothelium remains intact. However culture times longer than 48 hours appeared to affect the opacity of the corneas and were therefore not used. Cy3 labeled oligomers were used to determine the extent of penetration of the oligomer into the cultured cornea. Confocal optical slices down through the intact cornea show that fluorescent signal is present with CY3 labeled oligomers at FIG. 13A shows fluorescent signal 10 μm deep in the cultured cornea 1 hour after initial treatment. TaqMan probes conjugated to oligodeoxynucleotides were used to measure and demonstrate the delivery of intact oligodeoxynucleotide with 30% Pluronic gel into corneal epithelium. A significant proportion of oligomer remained intact one hour after treatment (FIG. 13B, 13C). The punctuate signal of intact oligomers (FRET occurring in FIG. 13C) can be seen as the red (represented on gray-scale) wavelength while signal from degraded oligomers (no FRET) appears in the green (represented on gray-scale) emission spectrum (FIG. 13B).

Deoxyribozyme Assay Predicts ODNs that can Knockdown Connexin43 Protein in Corneal Epithelium.

Figure 14:
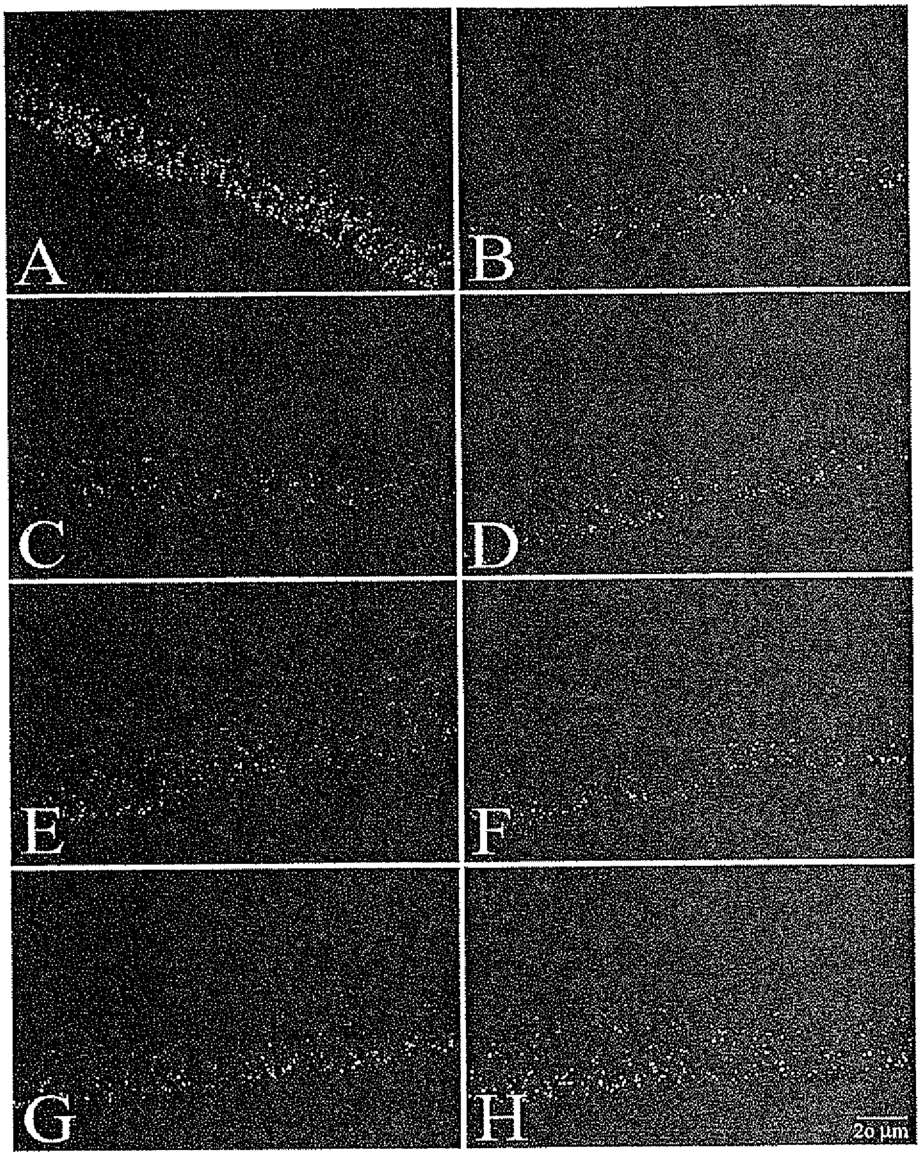
FIG. 14 illustrates the effects of different antisense oligomers on connexin-43 (light, gray-scale) and connexin-26 (dark, gray-scale) protein expression were shown by in vitro deoxyribozyme mRNA cleavage.

In a preliminary experiment, we treated rat corneas with a single application of our positive control, DB1, and found no significant changes in connexin43 protein expression after 8 hours. Clear protein knockdown at 24 hours was seen after three applications at eight hourly intervals. Based in part on results from the deoxyribozyme cleavage assay we tested certain antisense oligomers in vivo (DB1, r43as605, r43as783, r43as885, r43as953 and r43as1076), as well as antisense oligomers that were predicted to be non-functional (r43as14, r43as769 and r43as892), and a negative control (DB1 sense). We found knockdown of connexin43 protein levels after 24 hours of treatment compared to controls (FIG. 14A) with all of the antisense oligomers that we had determined should be positive (FIG. 14C, 14E, 14G). All three of those predicted to be negative, and the negative control oligomer, did not affect connexin43 expression (FIG. 14B, 14D, 4F, 4H). DB1, a 30-mer version of as885, showed a similar percentage knock down to the shorter as885 (just under 50% knockdown). One of the better antisense oligomers identified in this experiment appeared to be as605 with a 64% reduction in protein level. A summary of these results quantified is presented in FIG. 15.

To test the technique for other connexins, further oligodeoxynucleotides were designed and tested for connexin26. Two 30-mer antisense oligodeoxynucleotides designated as r26as330N and 375N, together with their appropriate reverse control oligodeoxynucleotides were designed against connexin26 based on regions within the cleavage areas of b2dz330 and b2dz375. We found that these antisense oligodeoxynucleotides (as330N and as375N) did not, however, lead to a significant difference in protein expression levels within the 12 hour time period for these experiments when antisense oligomers treated cultures were compared with the reverse control treated corneas.

Antisense ODNS Lead to Reduction in Connexin43 and Connexin 26 mRNA

Figure 16:
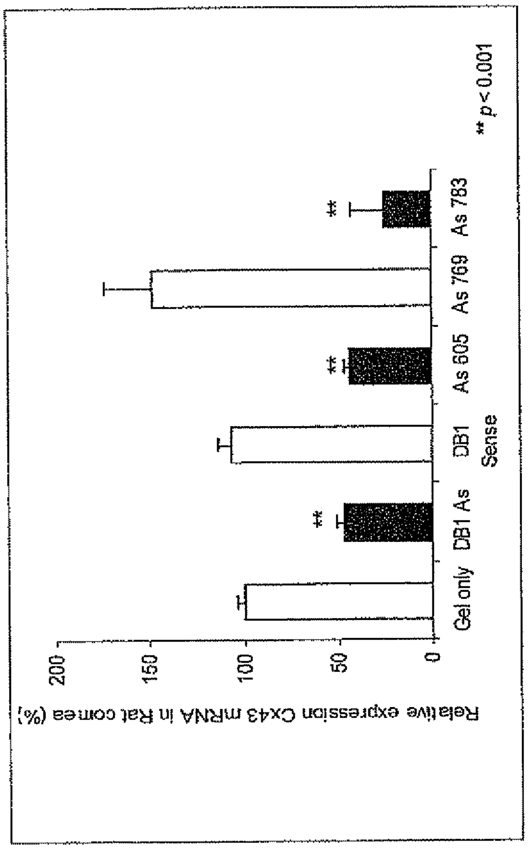
FIG. 16 illustrates a comparison of connexin43 mRNA levels in rat cornea treated with antisense or sense oligomers assessed using Real-Time PCR. The level is expressed as a percentage of Pluronic gel only treated cornea. Three antisense ligodeoxynucleotides predicted by in vitro assay to be functional, DB1As, As605 and As783 (black bars), reduced connexin43 mRNA expression to 46.8%, 44% and 25% of normal (gel only open bar) levels respectively (** $p<0.001$). No reduction was seen for the DB1 sense control oligomer (106%) (open bar DB1 sense). As769, which did not show any cleavage of Cx43 cRNA in the in vitro deoxyribozyme tertiary prediction assay, served as a negative control (148%) (open bar As769).

Real time PCR was used to determine the effect of antisense oligodeoxynucleotides on mRNA levels. It confirmed that antisense oligodeoxynucleotides that knock down connexin43 protein expression (as605, as885, DB1) also have lower connexin43 mRNA levels compared to control corneas within 8 hours after treatment (FIG. 16). The percentage reduction in relative levels of connexin43 mRNA correlated well with the level of reduction of connexin43 protein. The negative antisense oligomer (as769) and negative controls (DB1 sense, gel only) exhibited unchanged levels of connexin43 mRNA compared to control corneas.

Figure 17:
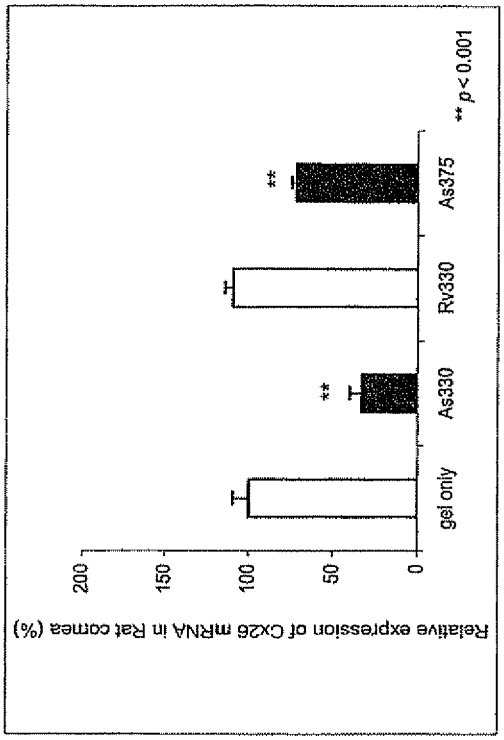
FIG. 17 illustrates a comparison of connexin26 mRNA levels in rat cornea treated with antisense or sense (control) oligomers and assessed using Real-Time PCR. The level is expressed as percentage of pluronic gel only treated cornea (gel only open bar). As330 and As375 reduced Cx26 mRNA expression to 33% and 71% respectively (** $p<0.001$) (black bars). No reduction was seen for Rv330 sense oligomer (109%) (Rv330 open bar).

Connexin26 mRNA expression was also significantly reduced by as330N and as 375N within 8 hours of antisense treatment (FIG. 17). The reverse sequence control for as330N and a gel only control exhibited no effect on mRNA levels.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treating an ophthalmic disorder affecting the posterior segment in a subject, the method comprising administering to the subject an anti-connexin 43 peptidomimetic compound capable of down-regulating connexin 43 biological activity.

2. The method of claim 1 wherein said connexin 43 biological activity is cell-cell communication.

3. The method of claim 1 wherein connexin 43 gap-junction-mediated-cell-cell communication is down-regulated.

4. The method of claim 1 wherein said ophthalmic disorder affecting the posterior segment is an ophthalmic disorder affecting the lens.

5. The method of claim 1 wherein said ophthalmic disorder affecting the posterior segment is an ophthalmic disorder affecting the retina.

6. The method of claim 1 wherein said ophthalmic disorder affecting the posterior segment is diabetic retinopathy.

7. The method of claim 1 wherein said ophthalmic disorder affecting the posterior segment is macular degeneration.

8. The method of claim 1 wherein said ophthalmic disorder affecting the posterior segment is vitreoretinopathy.

9. The method of claim 1 wherein said ophthalmic disorder affecting the posterior segment is selected from the group consisting of macular holes and retinal tears.

10. The method of claim 1 wherein said anti-connexin 43 peptidomimetic compound is administered by local administration.

11. The method of claim 1 wherein said anti-connexin 43 peptidomimetic compound is administered systemically.

12. The method of claim 1 wherein said anti-connexin 43 peptidomimetic compound is administered by intraocular injection.

13. The method of claim 1 wherein said anti-connexin 43 peptidomimetic compound is formulated for parenteral administration.

* * * * *